(12) United States Patent
Martynova et al.

(10) Patent No.: US 9,608,208 B2
(45) Date of Patent: Mar. 28, 2017

(54) COMPOUNDS FOR ELECTRONIC DEVICES

(75) Inventors: Irina Martynova, Griesheim (DE); Amir Hossain Parham, Frankfurt am Main (DE); Christof Pflumm, Darmstadt (DE)

(73) Assignee: Merck Patent GmbH (DE)

( * ) Notice: Subject to any disclaimer, the term of this patent is extended or adjusted under 35 U.S.C. 154(b) by 663 days.

(21) Appl. No.: 13/985,671

(22) PCT Filed: Jan. 18, 2012

(86) PCT No.: PCT/EP2012/000206
§ 371 (c)(1),
(2), (4) Date: Aug. 15, 2013

(87) PCT Pub. No.: WO2012/110182
PCT Pub. Date: Aug. 23, 2012

(65) Prior Publication Data
US 2013/0320262 A1 Dec. 5, 2013

(30) Foreign Application Priority Data
Feb. 17, 2011 (DE) .................. 10 2011 011 539

(51) Int. Cl.
| | | |
|---|---|---|
| H01L 51/00 | (2006.01) | |
| C09K 11/06 | (2006.01) | |
| H05B 33/14 | (2006.01) | |
| C07D 487/14 | (2006.01) | |
| C07D 471/22 | (2006.01) | |
| C07D 487/04 | (2006.01) | |
| C07D 491/14 | (2006.01) | |
| C07D 495/14 | (2006.01) | |
| C07D 498/14 | (2006.01) | |
| C07D 513/14 | (2006.01) | |
| C07D 519/00 | (2006.01) | |
| C07F 9/6561 | (2006.01) | |
| H01L 51/05 | (2006.01) | |
| H01L 51/42 | (2006.01) | |
| H01L 51/50 | (2006.01) | |

(52) U.S. Cl.
CPC ........ *H01L 51/0072* (2013.01); *C07D 471/22* (2013.01); *C07D 487/04* (2013.01); *C07D 487/14* (2013.01); *C07D 491/14* (2013.01); *C07D 495/14* (2013.01); *C07D 498/14* (2013.01); *C07D 513/14* (2013.01); *C07D 519/00* (2013.01); *C07F 9/6561* (2013.01); *C09K 11/06* (2013.01); *H01L 51/0035* (2013.01); *H01L 51/0036* (2013.01); *H01L 51/0067* (2013.01); *H01L 51/0071* (2013.01); *H01L 51/0073* (2013.01); *H01L 51/0074* (2013.01); *H05B 33/14* (2013.01); *C09K 2211/1007* (2013.01); *C09K 2211/1011* (2013.01); *C09K 2211/1014* (2013.01); *C09K 2211/1029* (2013.01); *C09K 2211/1033* (2013.01); *C09K 2211/1037* (2013.01); *C09K 2211/1044* (2013.01); *C09K 2211/1059* (2013.01); *C09K 2211/1088* (2013.01); *C09K 2211/1092* (2013.01); *H01L 51/006* (2013.01); *H01L 51/0077* (2013.01); *H01L 51/0508* (2013.01); *H01L 51/42* (2013.01); *H01L 51/5012* (2013.01); *H01L 51/5056* (2013.01); *H01L 51/5072* (2013.01); *H01L 51/5096* (2013.01); *Y02E 10/549* (2013.01)

(58) Field of Classification Search
None
See application file for complete search history.

(56) References Cited

U.S. PATENT DOCUMENTS

2013/0092879 A1   4/2013   Fortte et al.

FOREIGN PATENT DOCUMENTS

| | | |
|---|---|---|
| JP | 2000268962 A | 9/2000 |
| WO | WO-2011157346 A1 | 12/2011 |

OTHER PUBLICATIONS

Miller, W.V., et al., "Zur Synthese von Indenderivaten", Berichte der Deutschen Chemischen Gesellschaft, Vo. 23, (1890), pp. 1881-1886.
International Search Report for PCT/EP2012/000206 mailed Jul. 10, 2012.

*Primary Examiner* — J. L. Yang
(74) *Attorney, Agent, or Firm* — Drinker Biddle & Reath LLP

(57) ABSTRACT

The present invention relates to a compound of a formula (I), (II) or (III), to the use of this compound in an electronic device, and to an electronic device comprising one or more compounds of the formula (I), (II) or (III). The invention furthermore relates to a process for the preparation of a compound of the formula (I), (II) or (III) and to a formulation comprising one or more compounds of the formula (I), (II) or (III).

18 Claims, No Drawings

COMPOUNDS FOR ELECTRONIC DEVICES

CROSS-REFERENCE TO RELATED APPLICATIONS

This application is a national stage application (under 35 U.S.C. §371) of PCT/EP2012/000206, filed Jan. 18, 2012, which claims benefit of German application 10 2011 011 539.0, filed Feb. 17, 2011 which are both incorporated by reference.

The present invention relates to a compound of a formula (I), (II) or (III), to the use of this compound in an electronic device, and to an electronic device comprising one or more compounds of the formula (I), (II) or (III). The invention furthermore relates to a process for the preparation of a compound of the formula (I), (II) or (III) and to a formulation comprising one or more compounds of the formula (I), (II) or (III).

Organic semiconductor materials, such as the compounds according to the invention, are being developed for a number of different applications in electronic devices. The structure of organic electroluminescent devices (OLEDs) in which the compounds according to the invention can be employed as functional materials is described, for example, in U.S. Pat. No. 4,539,507, U.S. Pat. No. 5,151,629, EP 0676461 and WO 1998/27136.

Further improvements are still necessary with respect to the performance data of the organic electroluminescent devices, in particular with a view to broad commercial use. Of particular importance in this connection are the lifetime, the efficiency and the operating voltage of the organic electroluminescent devices and the colour values achieved. In particular in the case of blue-emitting electroluminescent devices, there is potential for improvement with respect to the lifetime of the devices.

In addition, it is desirable for the compounds for use as organic semiconductor materials to have high thermal stability and a high glass-transition temperature and to be sublimable without decomposition.

Furthermore, there is, inter alia, a demand for alternative matrix materials for use in electronic devices. In particular, there is a demand for matrix materials for phosphorescent emitters which simultaneously result in good efficiency, a long lifetime and a low operating voltage. It is precisely the properties of the matrix materials that are frequently limiting for the lifetime and efficiency of the organic electroluminescent device.

In accordance with the prior art, carbazole derivatives, for example bis(carbazolyl)biphenyl, are frequently used as matrix materials. There is still potential for improvement here, in particular with respect to the lifetime and glass-transition temperature of the materials.

Furthermore, ketone compounds, for example as described in WO 2005/084081, WO 2004/093207 and WO 2004/013080, are employed in accordance with the prior art as matrix materials in OLEDs. Again furthermore, triazine compounds are used in accordance with the prior art as matrix materials, for example as disclosed in WO 2010/015306, WO 2007/063754 or WO 2008/056746. However, there continues to be a demand for alternative compounds having a different chemical structure, in particular those which effect an improvement with respect to lifetime, efficiency and operating voltage.

Also of particular interest is the provision of alternative materials as matrix components of mixed-matrix systems. A mixed-matrix system in the sense of this application is taken to mean a system in which two or more different matrix compounds are used mixed together with one (or more) dopant compounds as the emitting layer. These systems are, in particular, of interest in the case of phosphorescent organic electroluminescent devices. For more detailed information, reference is made to the application WO 2010/108579. Compounds known from the prior art which may be mentioned as matrix components in mixed-matrix systems are, inter alia, CBP (biscarbazolylbiphenyl) and TCTA (tris-carbazolyltriphenylamine). However, there continues to be a demand for alternative compounds for use as matrix components in mixed-matrix systems. In particular, there is a demand for compounds which effect an improvement in the operating voltage and lifetime of the electronic devices.

Furthermore, the provision of novel electron-transport materials is desirable, since it is precisely also the properties of the electron-transport material that have a significant influence on the above-mentioned properties of the organic electroluminescent device. In particular, there is a demand for electron-transport materials which simultaneously result in good efficiency, a long lifetime and low operating voltage.

The applications WO 2010/136109 and WO 2011/000455 disclose indenocarbazole and indolocarbazole derivatives having different linking geometry of the indene or indole and carbazole units. The compounds are very highly suitable for use as functional materials in organic electroluminescent devices, in particular as matrix materials for phosphorescent emitters and as electron-transport materials. However, there continues to be a demand for alternative compounds, in particular those by means of which a reduction in the operating voltage, an increase in the power efficiency and an increase in the lifetime can be achieved.

The application JP 2006/066580 discloses carbazole derivatives containing condensed aromatic rings, inter alia for use as host materials in an organic electroluminescent device.

The application JP 2007/088016 discloses organic semiconductor materials which have a plurality of pyrrole rings condensed with one another, inter alia for use in OLEDs.

The as yet unpublished application DE 102010033548.7 discloses organic semiconductor materials which have a plurality of heteroaromatic five-membered rings condensed with one another. According to the said application, the materials are preferably used in OLEDs.

The present invention relates to compounds of the formula (I), (II) and (III), which exhibit advantageous properties on use in an electronic device, preferably an organic electroluminescent device. The advantageous properties are described in detail in one of the following sections and in the experimental examples.

The invention thus relates to a compound of a formula (I), (II) or (III)

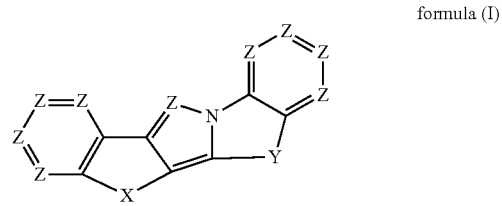

formula (I)

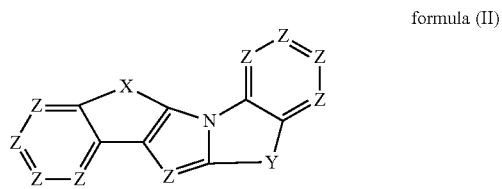

formula (II)

formula (III)

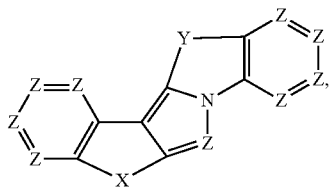

where the following applies to the symbols occurring:
Z is selected on each occurrence, identically or differently, from $CR^2$ and N;
X, Y are on each occurrence, identically or differently, a divalent group selected from $BR^2$, $C(R^2)_2$, C=O, C=$NR^2$, C=$C(R^2)_2$, C=S, $Si(R^2)_2$, $NR^1$, $PR^2$, P(=O)$R^2$, O, S, S=O and $S(=O)_2$;
$R^1$ is on each occurrence, identically or differently, an aromatic or heteroaromatic ring system having 5 to 60 aromatic ring atoms, which may be substituted by one or more radicals $R^3$ and which may be linked to a substituent $R^2$ on the skeleton or an atom of the skeleton;
$R^2$ is on each occurrence, identically or differently, H, D, F, Cl, Br, I, $B(OR^3)_2$, CHO, C(=O)$R^3$, $CR^3$=$C(R^3)_2$, CN, C(=O)$OR^3$, C(=O)$N(R^3)_2$, $Si(R^3)_3$, $N(R^3)_2$, $N(Ar^1)_2$, $NO_2$, P(=O)$(R^3)_2$, $OSO_2R^3$, $OR^3$, $S(=O)R^3$, $S(=O)_2R^3$, a straight-chain alkyl, alkoxy or thioalkyl group having 1 to 20 C atoms or a branched or cyclic alkyl, alkoxy or thioalkyl group having 3 to 20 C atoms or an alkenyl or alkynyl group having 2 to 20 C atoms, where the above-mentioned groups may each be substituted by one or more radicals $R^3$ and where one or more adjacent or non-adjacent $CH_2$ groups in the above-mentioned groups may be replaced by —$R^3C$=$CR^3$—, —C≡C—, $Si(R^3)_2$, $Ge(R^3)_2$, $Sn(R^3)_2$, C=O, C=S, C=Se, C=$NR^3$, —C(=O)O—, —C(=O)$NR^3$—, $NR^3$, P(=O)($R^3$), —O—, —S—, SO or $SO_2$ and where one or more H atoms in the above-mentioned groups may be replaced by D, F, Cl, Br, I, CN or $NO_2$, or an aromatic or heteroaromatic ring system having 5 to 60 aromatic ring atoms, which may in each case be substituted by one or more radicals $R^3$, or an aryloxy or heteroaryloxy group having 5 to 60 aromatic ring atoms, which may be substituted by one or more radicals $R^3$, where two or more radicals $R^2$ may be linked to one another and may form a ring or a ring system;
$R^3$ is on each occurrence, identically or differently, H, D, F, Cl, Br, I, $B(OR^4)_2$, CHO, C(=O)$R^4$, $CR^4$=$C(R^4)_2$, CN, C(=O)$OR^4$, C(=O)$N(R^4)_2$, $Si(R^4)_3$, $N(R^4)_2$, $NO_2$, P(=O)$(R^4)_2$, $OSO_2R^4$, $OR^4$, $S(=O)R^4$, $S(=O)_2R^4$, a straight-chain alkyl, alkoxy or thioalkyl group having 1 to 20 C atoms or a branched or cyclic alkyl, alkoxy or thioalkyl group having 3 to 20 C atoms or an alkenyl or alkynyl group having 2 to 20 C atoms, where the above-mentioned groups may each be substituted by one or more radicals $R^4$ and where one or more adjacent or non-adjacent $CH_2$ groups in the above-mentioned groups may be replaced by —$R^4C$=$CR^4$—, —C≡C—, $Si(R^4)_2$, $Ge(R^4)_2$, $Sn(R^4)_2$, C=O, C=S, C=Se, C=$NR^4$, —C(=O)O—, —C(=O)$NR^4$—, $NR^4$, P(=O)($R^4$), —O—, —S—, SO or $SO_2$ and where one or more H atoms in the above-mentioned groups may be replaced by D, F, Cl, Br, I, CN or $NO_2$, or an aromatic or heteroaromatic ring system having 5 to 60 aromatic ring atoms, which may in each case be substituted by one or more radicals $R^4$, or an aryloxy or heteroaryloxy group having 5 to 60 aromatic ring atoms, which may be substituted by one or more radicals $R^4$, where two or more radicals $R^3$ may be linked to one another and may form a ring or a ring system;
$R^4$ is, identically or differently on each occurrence, H, D, F or an aliphatic, aromatic and/or heteroaromatic organic radical having 1 to 20 C atoms, in which, in addition, one or more H atoms may be replaced by D or F; two or more substituents $R^4$ here may also be linked to one another and form a ring or a ring system;
$Ar^1$ is on each occurrence, identically or differently, an aromatic or heteroaromatic ring system having 5 to 30 aromatic ring atoms, which may be substituted by one or more radicals $R^3$.

In the compounds according to the invention, it is preferred for 0, 1, 2, 3, 4, 5 or 6 groups Z to be equal to N, and for the remaining groups Z to be equal to $CR^2$. Furthermore preferably, 0, 1 or 2 groups Z per aromatic six-membered ring in a compound of the formula (I), (II) or (III) are equal to N and the remaining groups Z are equal to $CR^2$.

According to a preferred embodiment of the invention, X is selected from $BR^2$, C=O, C=$C(R^2)_2$, $NR^1$, $PR^2$, P(=O)$R^2$, O, S, S=O and $S(=O)_2$. X is particularly preferably selected from C=O, $NR^1$, O, S, S=O and $S(=O)_2$. X is very particularly preferably equal to $NR^1$.

Furthermore, according to a preferred embodiment of the invention, Y is selected from $C(R^2)_2$, C=O, $NR^1$, $PR^2$, P(=O)$R^2$, O, S and $S(=O)_2$. Y is particularly preferably selected from $C(R^2)_2$, $NR^1$, O and S. Y is very particularly preferably equal to $C(R^2)_2$.

In a particularly preferred embodiment of the invention, the preferred embodiments of X and Y occur combined with one another. Preference is likewise given to the combined occurrence of the particularly preferred or very particularly preferred embodiments of X and Y.

In a preferred embodiment of the invention, $R^1$ is selected on each occurrence, identically or differently, from an aromatic or heteroaromatic ring system having 5 to 30 aromatic ring atoms, which may be substituted by one or more radicals $R^3$. The aromatic or heteroaromatic ring system particularly preferably includes one or more aryl or heteroaryl groups selected from benzene, naphthalene, anthracene, phenanthrene, pyrene, chrysene, benzanthracene, tetracene, pentacene, furan, benzofuran, thiophene, benzothiophene, pyrrole, indole, isoindole, carbazole, pyridine, quinoline, isoquinoline, pyrazole, imidazole, benzimidazole, pyridazine, pyrimidine, pyrazine, triazole, benzotriazole and triazine, each of which may be substituted by one or more radicals $R^3$. The aryl or heteroaryl groups are preferably connected to one another by single bonds and/or divalent groups selected from alkylene groups having 1 to 8 carbon atoms, alkenylene groups having 2 to 8 carbon atoms, C=O, $NR^3$, O or S.

In a further preferred embodiment of the invention, $R^2$ is selected on each occurrence, identically or differently, from H, D, F, CN, $Si(R^3)_3$, $N(R^3)_2$ or a straight-chain alkyl or alkoxy group having 1 to 20 C atoms or a branched or cyclic alkyl or alkoxy group having 3 to 20 C atoms, where the above-mentioned groups may each be substituted by one or more radicals $R^3$ and where one or more adjacent or non-adjacent $CH_2$ groups in the above-mentioned groups may be replaced by —C≡C—, —$R^3C$=$CR^3$—, $Si(R^3)_2$, C=O, C=$NR^3$, —$NR^3$—, —O—, —S—, —C(=O)O— or —C(=O)$NR^3$—, or an aromatic or heteroaromatic ring system having 5 to 20 aromatic ring atoms, which may in each case be substituted by one or more radicals $R^3$, where two or more radicals $R^2$ may be linked to one another and may form a ring or a ring system.

In a further preferred embodiment, $R^3$ is selected on each occurrence, identically or differently, from H, D, F, CN, $Si(R^4)_3$, $N(R^4)_2$ or a straight-chain alkyl or alkoxy group having 1 to 20 C atoms or a branched or cyclic alkyl or alkoxy group having 3 to 20 C atoms, where the above-mentioned groups may each be substituted by one or more radicals $R^4$ and where one or more adjacent or non-adjacent $CH_2$ groups in the above-mentioned groups may be replaced by —C≡C—, —$R^4$C=C$R^4$—, $Si(R^4)_2$, C=O, C=N$R^4$, —N$R^4$—, —O—, —S—, —C(=O)O— or —C(=O)N$R^4$—, or an aromatic or heteroaromatic ring system having 5 to 20 aromatic ring atoms, which may in each case be substituted by one or more radicals $R^4$, where two or more radicals $R^3$ may be linked to one another and may form a ring or a ring system.

It is furthermore preferred for the compounds according to the invention to carry as substituent $R^1$ or $R^2$ at least one group which is selected from heteroaryl groups having 1 to 20 C atoms, which may optionally be bonded via one or more divalent aryl groups bonded in between and which may be substituted by one or more radicals $R^3$, aromatic or heteroaromatic ring systems having 5 to 20 aromatic ring atoms, which may be substituted by one or more radicals $R^3$, and arylamine groups, which may be substituted by one or more radicals $R^3$, where the above-mentioned heteroaryl groups are preferably selected from pyridine, pyrimidine, pyridazine, pyrazine, triazine and benzimidazole, each of which may be substituted by one or more radicals $R^3$ and where the above-mentioned aromatic or heteroaromatic ring systems are preferably selected from naphthyl, anthracenyl, phenanthrenyl, benzanthracenyl, pyrenyl, biphenyl, terphenyl and quaterphenyl, each of which may be substituted by one or more radicals $R^3$.

The above-mentioned arylamine groups preferably represent groups of the following formula (A)

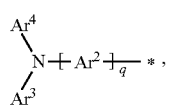

formula (A)

where the symbol * marks the bond to the remainder of the compound and furthermore $Ar^2$, $Ar^3$, $Ar^4$ represent, identically or differently, an aryl or heteroaryl group having 5 to 20 aromatic ring atoms, which may be substituted by one or more radicals $R^3$, where one or more combinations selected from $Ar^2$ and $Ar^2$, $Ar^2$ and $Ar^3$, $Ar^2$ and $Ar^4$ and $Ar^3$ and $Ar^4$ may in each case be linked to one another by a single bond or a divalent group selected from $BR^3$, $C(R^3)_2$, C=O, C=N$R^3$, C=C($R^3$)$_2$, C=S, $Si(R^3)_2$, N$R^3$, O, S, S=O and $S(=O)_2$; and q is equal to 0, 1, 2, 3, 4 or 5.

The above-mentioned heteroaryl groups, which may optionally be bonded via one or more divalent aryl groups bonded in between, preferably represent groups of the following formula (B)

$$HetAr^1 \text{---} (Ar^2)_k \text{---} *,$$ formula (B)

where the symbol * marks the bond to the remainder of the compound and furthermore $Ar^2$ is as defined above, k is equal to 0, 1, 2 or 3, and $HetAr^1$ represents a heteroaryl group having 1 to 20 C atoms, which may be substituted by one or more radicals $R^3$.

Preferred embodiments of the compounds of the formula (I), (II) and (III), in which the groups X and Y are defined as indicated, are shown in the following table (formulae (I-1) to (I-32), (II-1) to (II-32) and (III-1) to (III-32)).

| | X | Y |
|---|---|---|
| (I-1) | C=O | $C(R^2)_2$ |
| (I-2) | C=O | C=O |
| (I-3) | C=O | $NR^1$ |
| (I-4) | C=O | $PR^2$ |
| (I-5) | C=O | $PR^2(=O)$ |
| (I-6) | C=O | O |
| (I-7) | C=O | S |
| (I-8) | C=O | $S(=O)_2$ |
| (I-9) | $NR^1$ | $C(R^2)_2$ |
| (I-10) | $NR^1$ | C=O |
| (I-11) | $NR^1$ | $NR^1$ |
| (I-12) | $NR^1$ | $PR^2$ |
| (I-13) | $NR^1$ | $PR^2(=O)$ |
| (I-14) | $NR^1$ | O |
| (I-15) | $NR^1$ | S |
| (I-16) | $NR^1$ | $S(=O)_2$ |
| (I-17) | S | $C(R^2)_2$ |
| (I-18) | S | C=O |
| (I-19) | S | $NR^1$ |
| (I-20) | S | $PR^2$ |
| (I-21) | S | $PR^2(=O)$ |
| (I-22) | S | O |
| (I-23) | S | S |
| (I-24) | S | $S(=O)_2$ |
| (I-25) | $S(=O)_2$ | $C(R^2)_2$ |
| (I-26) | $S(=O)_2$ | C=O |
| (I-27) | $S(=O)_2$ | $NR^1$ |
| (I-28) | $S(=O)_2$ | $PR^2$ |
| (I-29) | $S(=O)_2$ | $PR^2(=O)$ |
| (I-30) | $S(=O)_2$ | O |
| (I-31) | $S(=O)_2$ | S |
| (I-32) | $S(=O)_2$ | $S(=O)_2$ |
| (II-1) | C=O | $C(R^2)_2$ |
| (II-2) | C=O | C=O |
| (II-3) | C=O | $NR^1$ |
| (II-4) | C=O | $PR^2$ |
| (II-5) | C=O | $PR^2(=O)$ |
| (II-6) | C=O | O |
| (II-7) | C=O | S |
| (II-8) | C=O | $S(=O)_2$ |
| (II-9) | $NR^1$ | $C(R^2)_2$ |
| (II-10) | $NR^1$ | C=O |
| (II-11) | $NR^1$ | $NR^1$ |
| (II-12) | $NR^1$ | $PR^2$ |
| (II-13) | $NR^1$ | $PR^2(=O)$ |
| (II-14) | $NR^1$ | O |
| (II-15) | $NR^1$ | S |
| (II-16) | $NR^1$ | $S(=O)_2$ |
| (II-17) | S | $C(R^2)_2$ |
| (II-18) | S | C=O |
| (II-19) | S | $NR^1$ |
| (II-20) | S | $PR^2$ |
| (II-21) | S | $PR^2(=O)$ |
| (II-22) | S | O |
| (II-23) | S | S |
| (II-24) | S | $S(=O)_2$ |
| (II-25) | $S(=O)_2$ | $C(R^2)_2$ |
| (II-26) | $S(=O)_2$ | C=O |
| (II-27) | $S(=O)_2$ | $NR^1$ |

| | X | Y |
|---|---|---|
| (II-28) | $S(=O)_2$ | $PR^2$ |
| (II-29) | $S(=O)_2$ | $PR^2(=O)$ |
| (II-30) | $S(=O)_2$ | O |
| (II-31) | $S(=O)_2$ | S |
| (II-32) | $S(=O)_2$ | $S(=O)_2$ |
| (III-1) | C=O | $C(R^2)_2$ |
| (III-2) | C=O | C=O |
| (III-3) | C=O | $NR^1$ |
| (III-4) | C=O | $PR^2$ |
| (III-5) | C=O | $PR^2(=O)$ |
| (III-6) | C=O | O |
| (III-7) | C=O | S |
| (III-8) | C=O | $S(=O)_2$ |
| (III-9) | $NR^1$ | $C(R^2)_2$ |
| (III-10) | $NR^1$ | C=O |
| (III-11) | $NR^1$ | $NR^1$ |
| (III-12) | $NR^1$ | $PR^2$ |
| (III-13) | $NR^1$ | $PR^2(=O)$ |
| (III-14) | $NR^1$ | O |
| (III-15) | $NR^1$ | S |
| (III-16) | $NR^1$ | $S(=O)_2$ |
| (III-17) | S | $C(R^2)_2$ |
| (III-18) | S | C=O |
| (III-19) | S | $NR^1$ |
| (III-20) | S | $PR^2$ |
| (III-21) | S | $PR^2(=O)$ |
| (III-22) | S | O |
| (III-23) | S | S |
| (III-24) | S | $S(=O)_2$ |
| (III-25) | $S(=O)_2$ | $C(R^2)_2$ |
| (III-26) | $S(=O)_2$ | C=O |
| (III-27) | $S(=O)_2$ | $NR^1$ |
| (III-28) | $S(=O)_2$ | $PR^2$ |
| (III-29) | $S(=O)_2$ | $PR^2(=O)$ |
| (III-30) | $S(=O)_2$ | O |
| (III-31) | $S(=O)_2$ | S |
| (III-32) | $S(=O)_2$ | $S(=O)_2$ |

According to a particularly preferred embodiment of the present invention, the preferred formulae shown in the table occur in combination with the preferred embodiments of the groups Z, $R^1$, $R^2$ and $R^3$ indicated above.

The following table shows examples of compounds in accordance with the present invention.

1

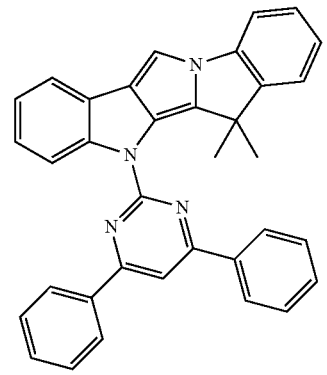

2

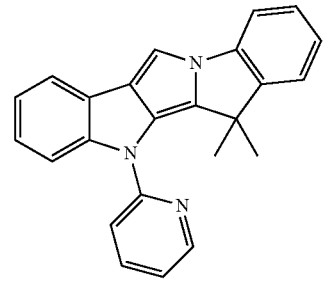

3

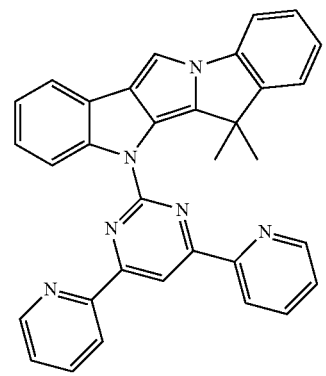

4

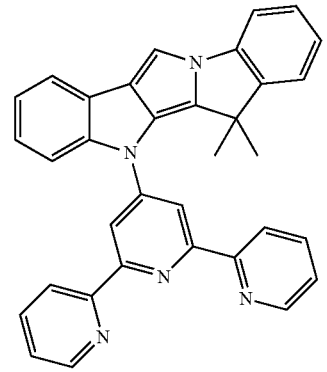

5

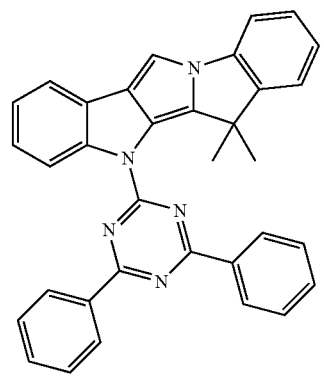

6
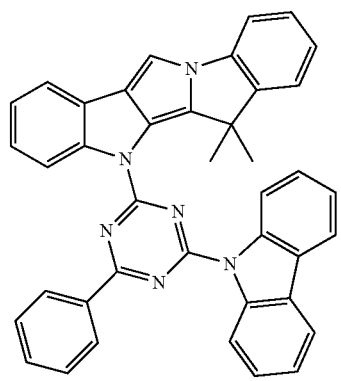
7
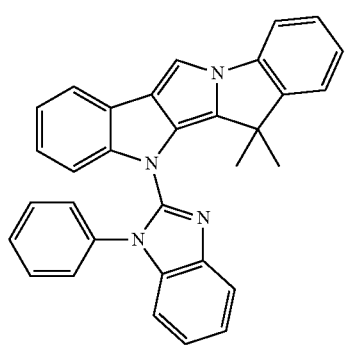
8
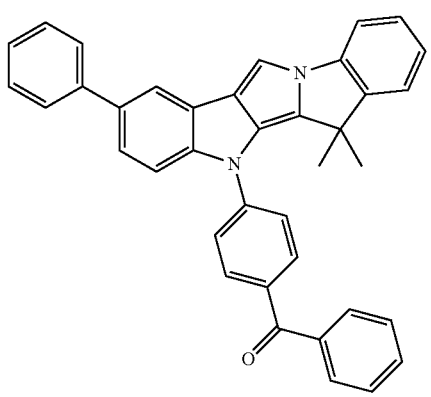
9
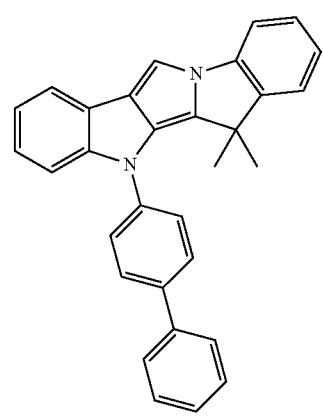
10
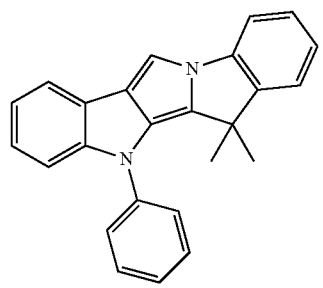
11
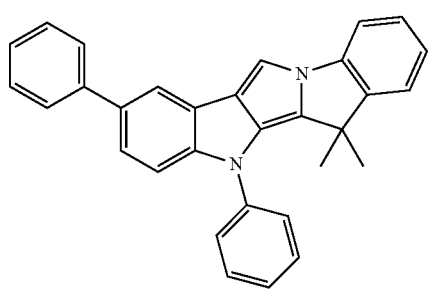
12
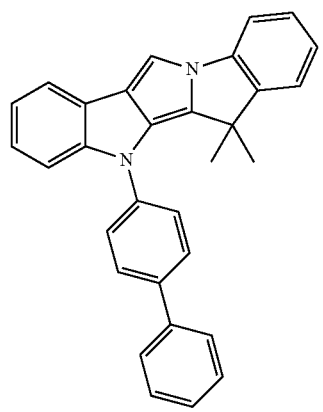
13
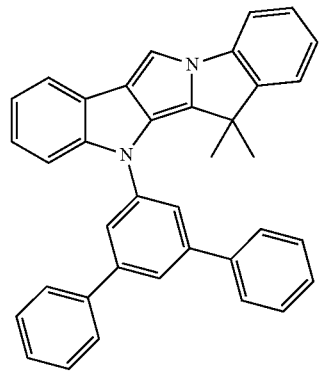

14
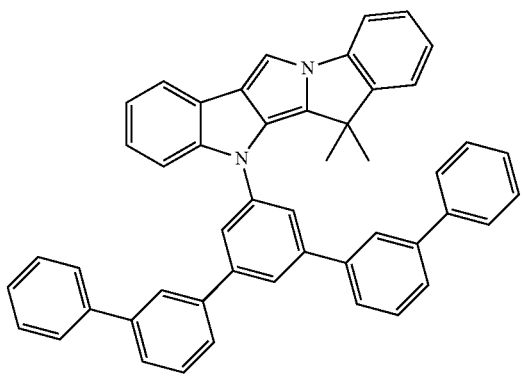
15
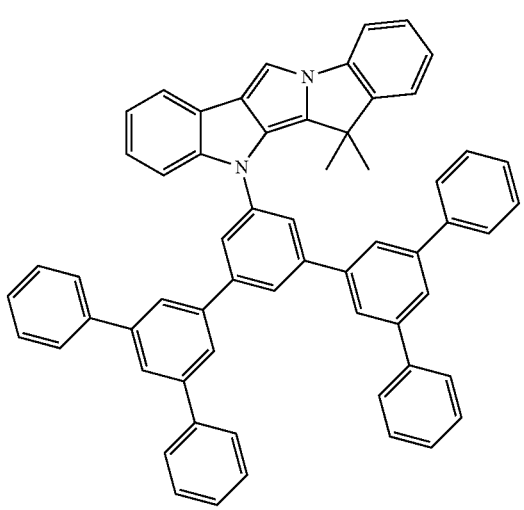
16
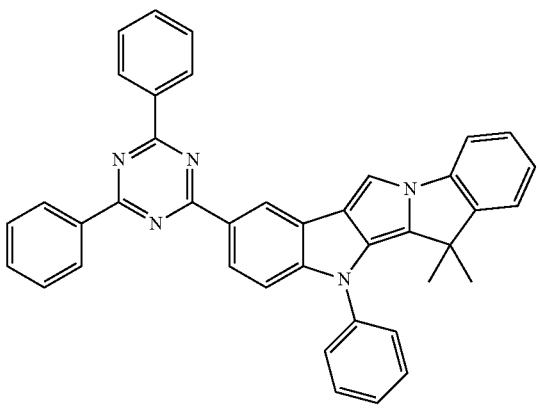
17
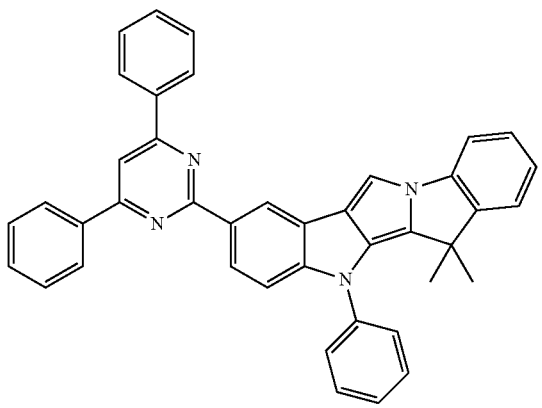
18
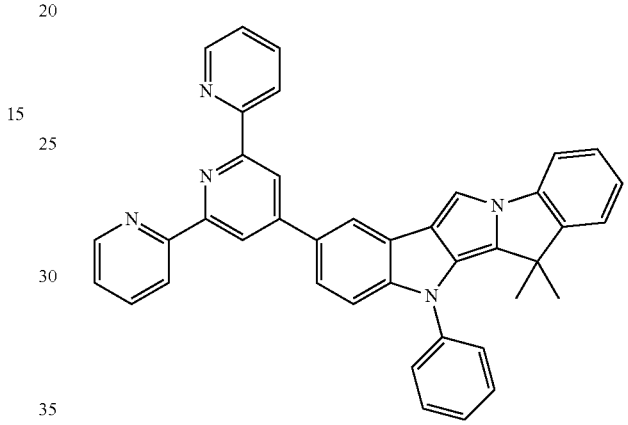
19
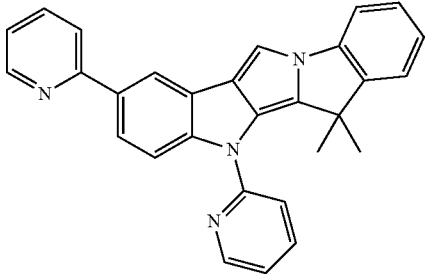
20
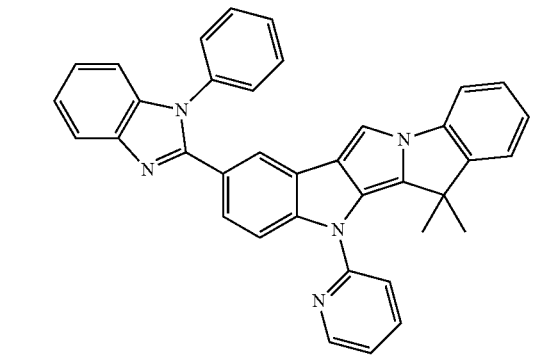

21
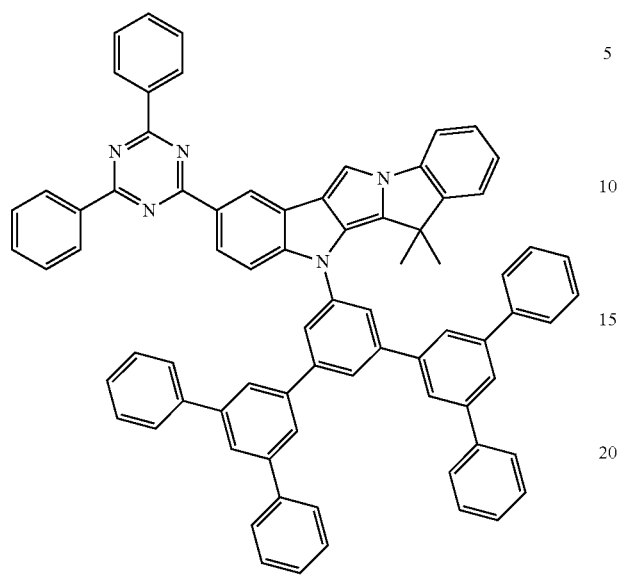
22
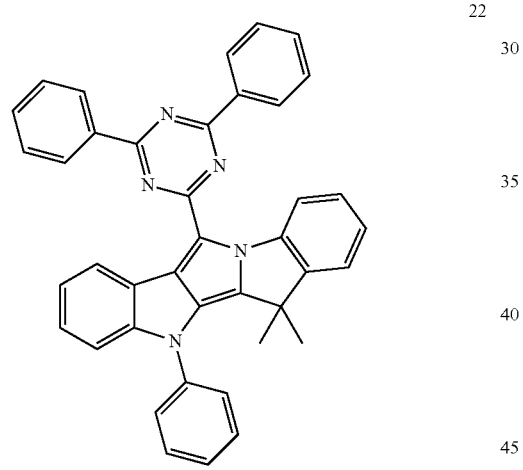
23
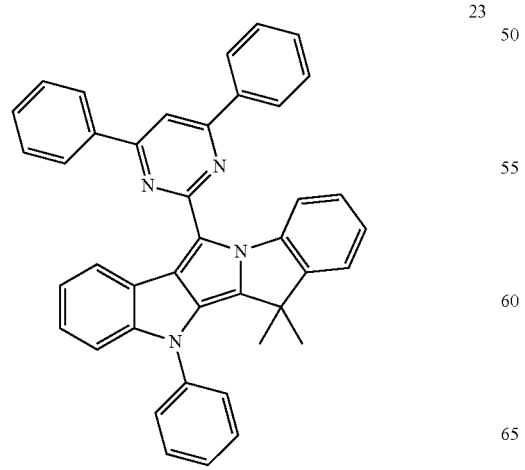
24
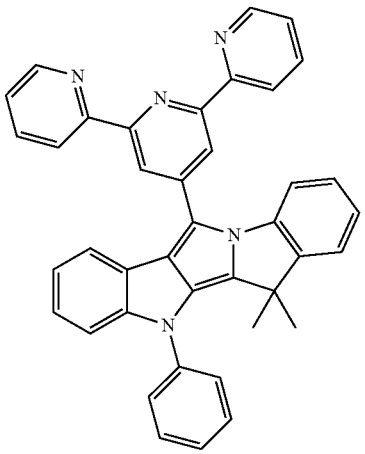
25
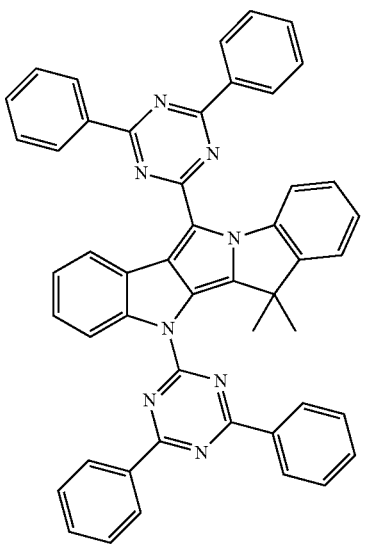
26

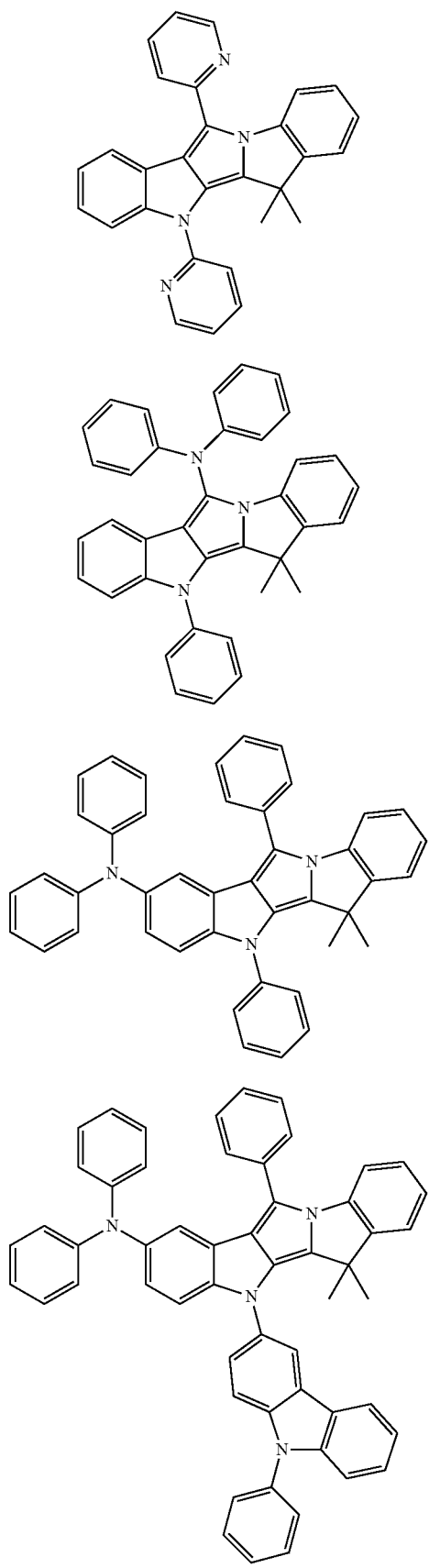
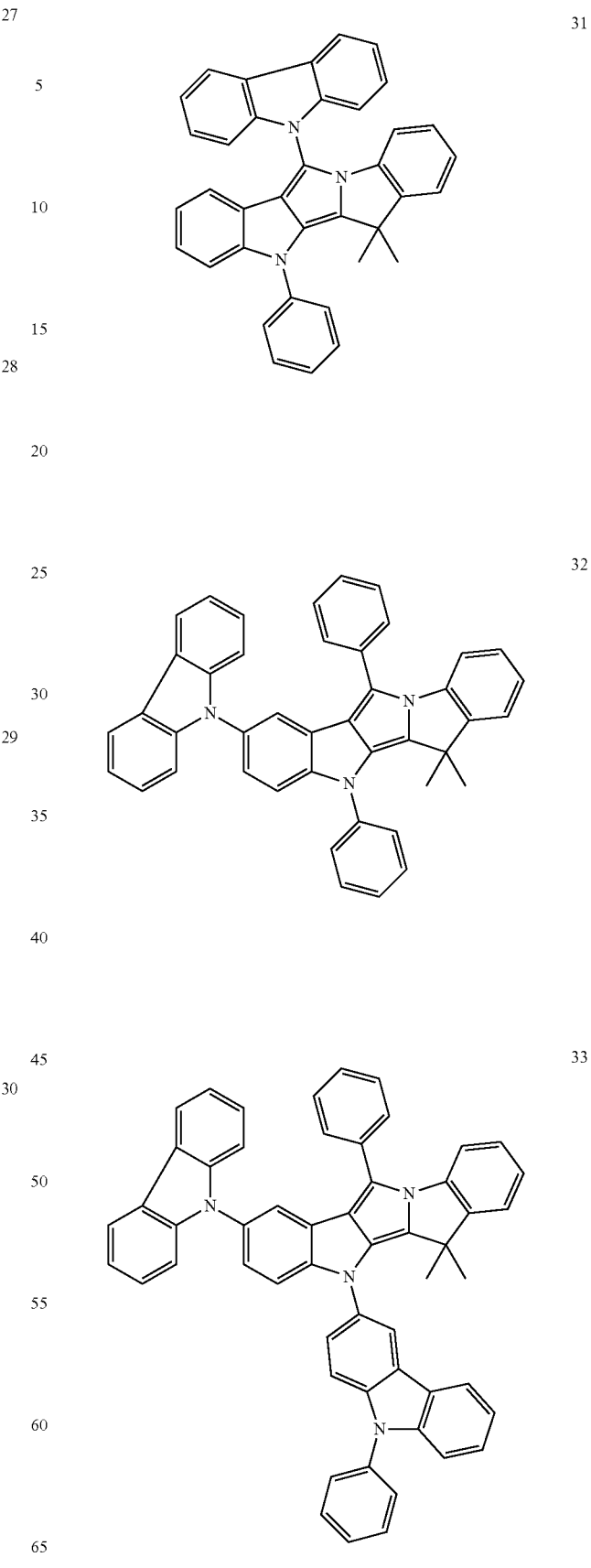

34
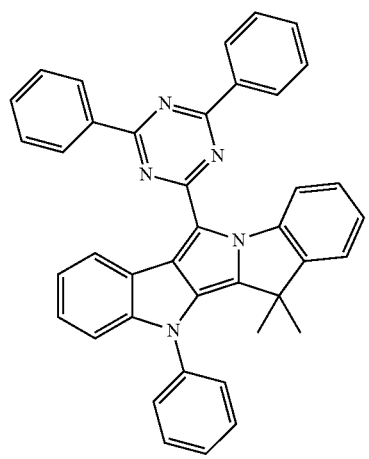
35
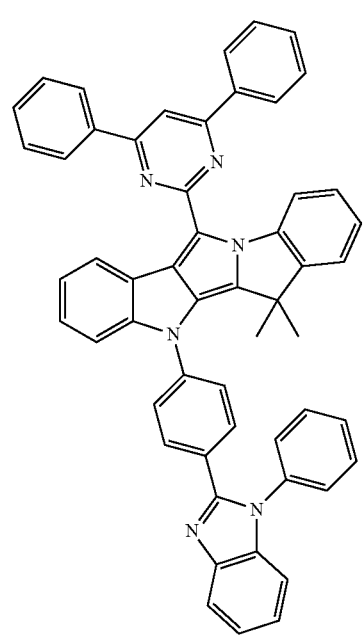
36
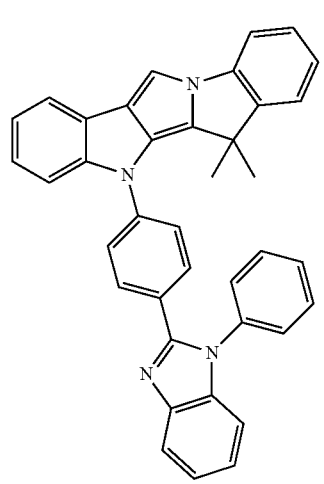
37
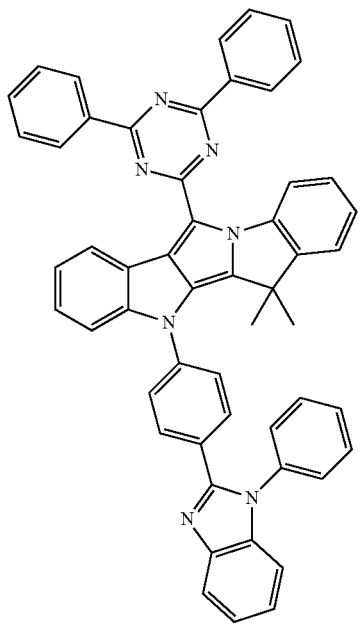
38
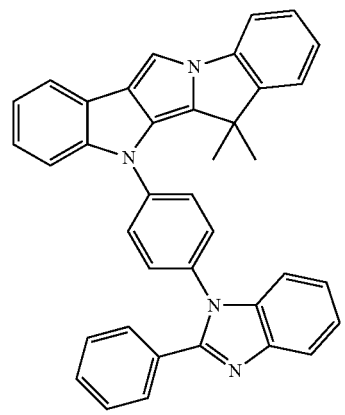
39
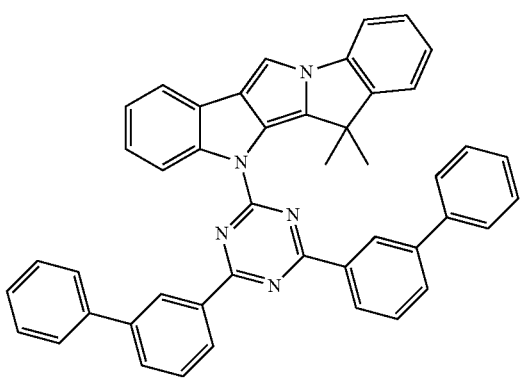

40
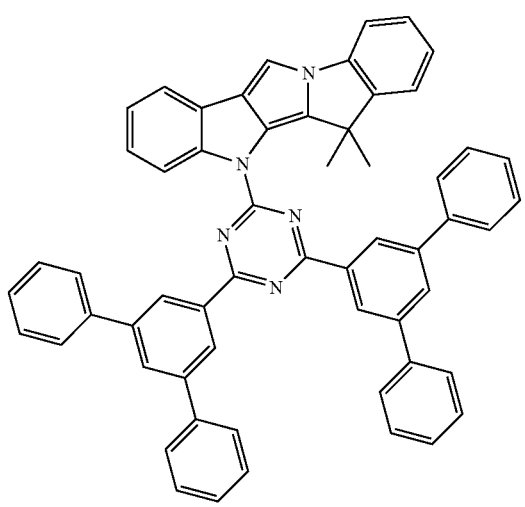
41
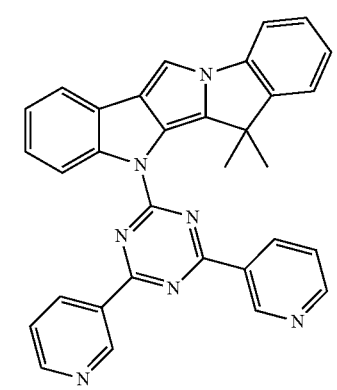
42
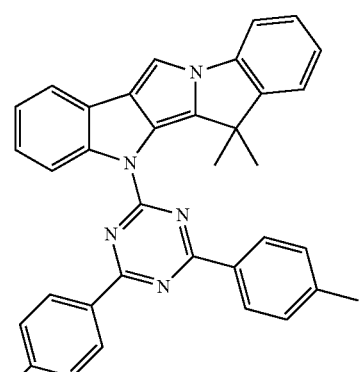
43
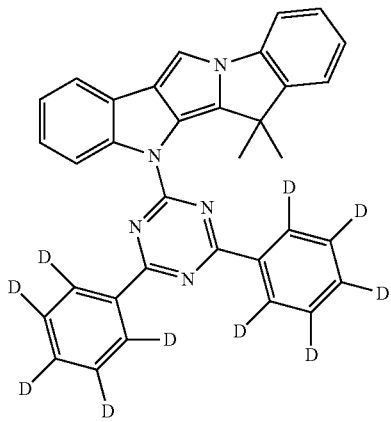
44
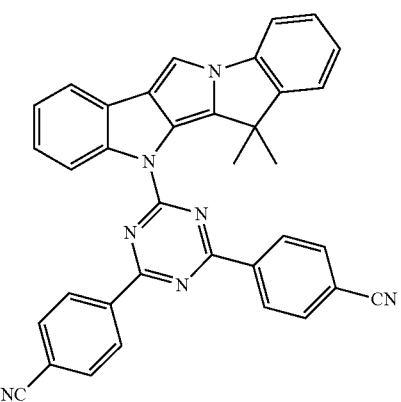
45
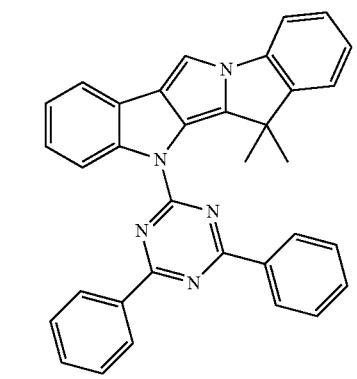
46
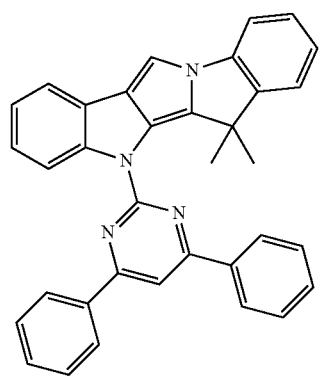

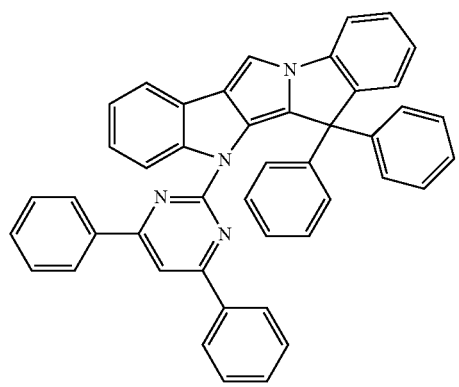
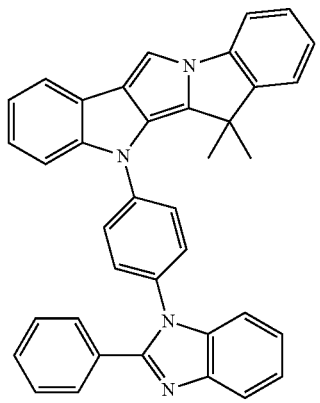
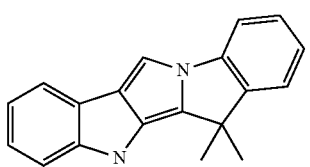
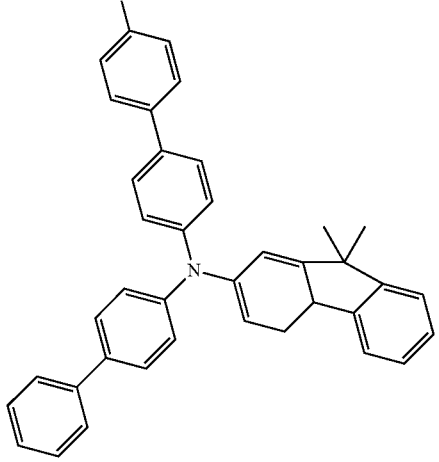
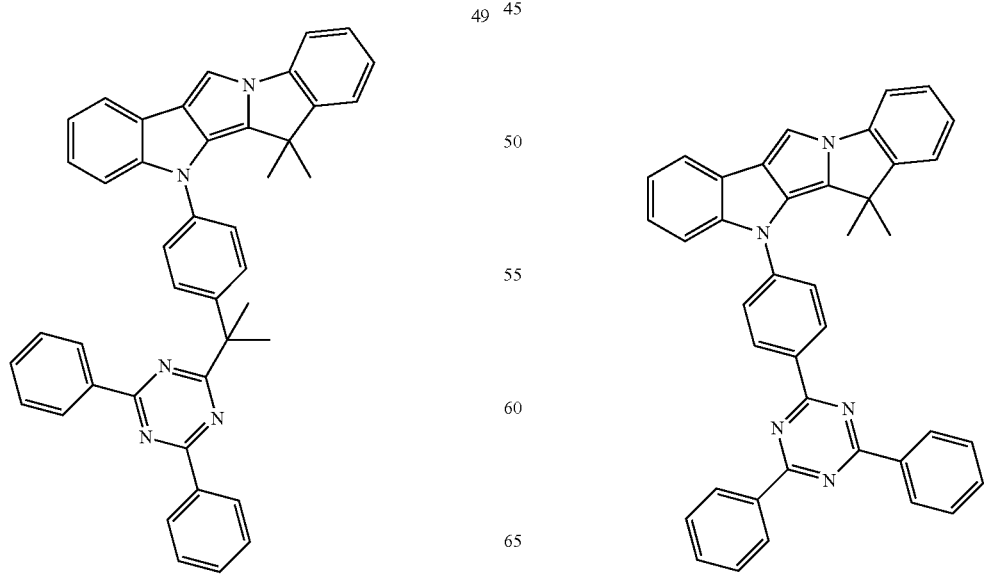

53
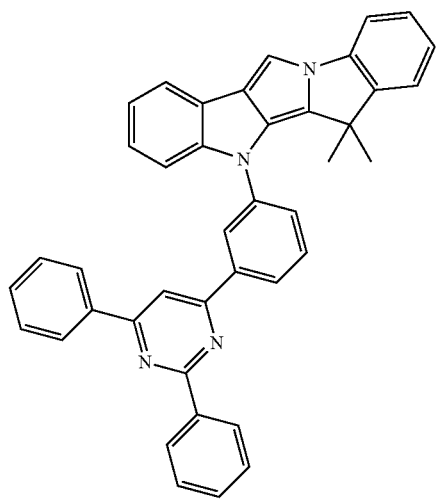
54
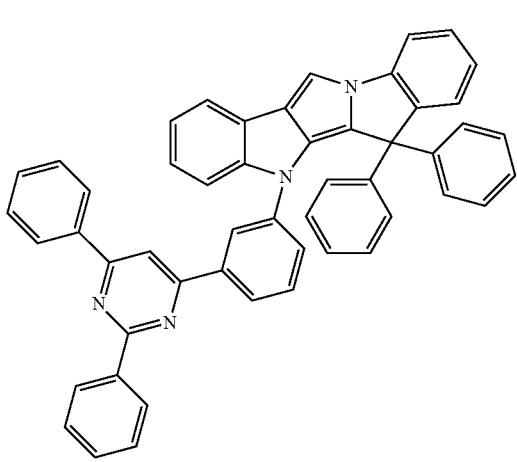
55
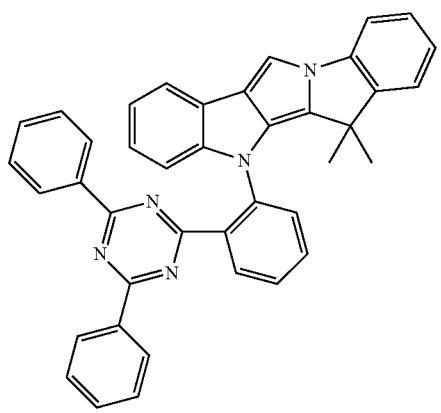
56
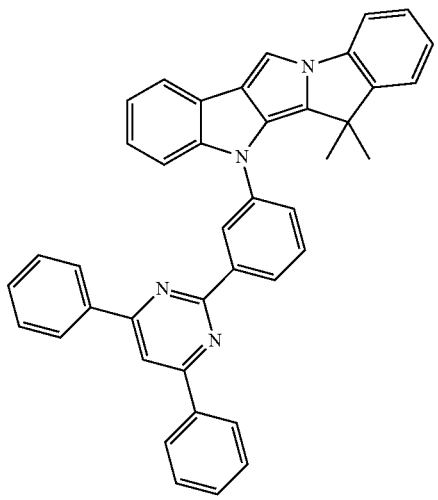
57
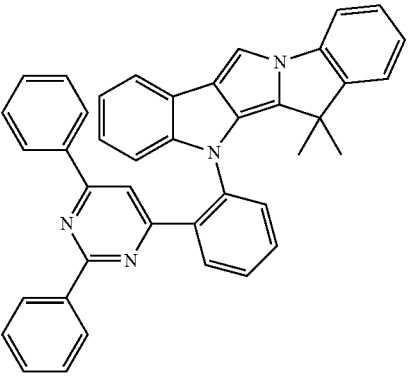
58
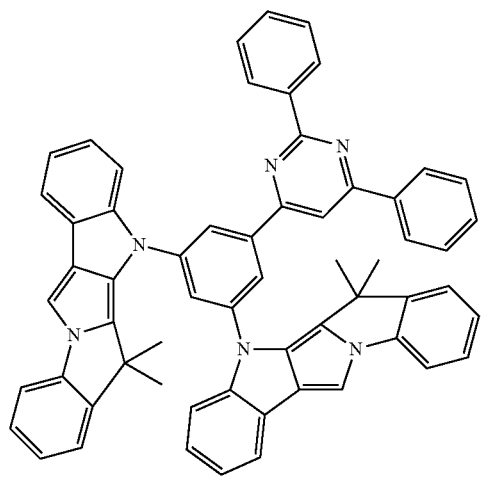

59
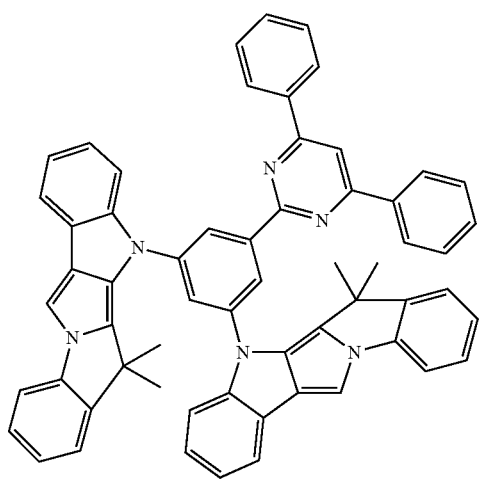
60
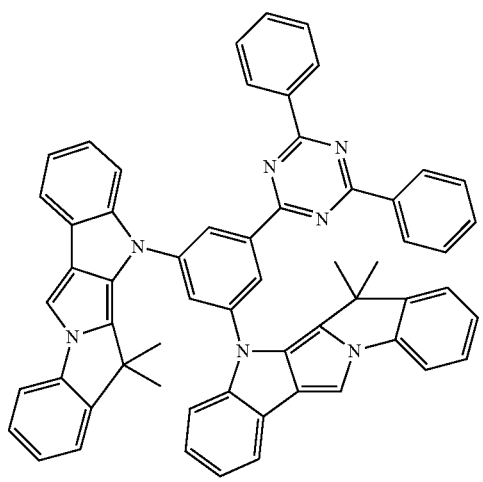
61
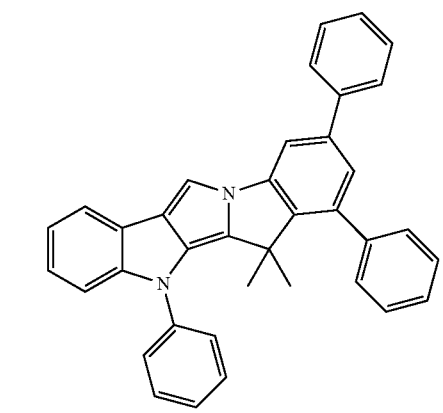
62
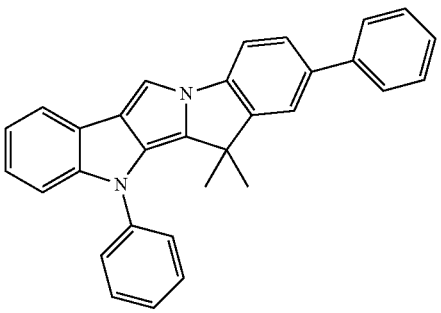
63
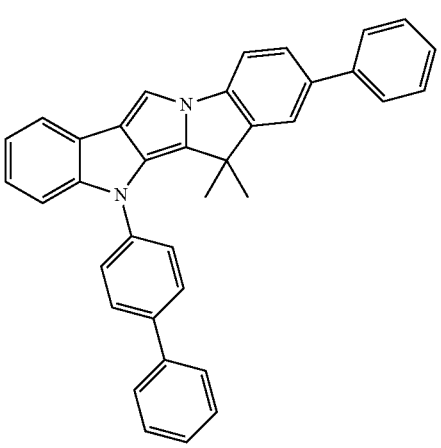
64
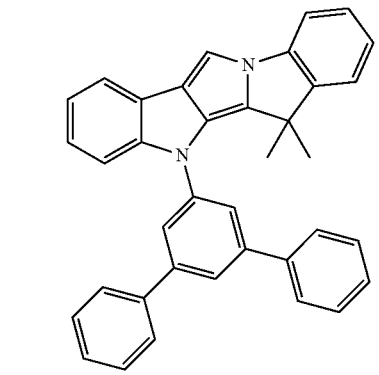
65
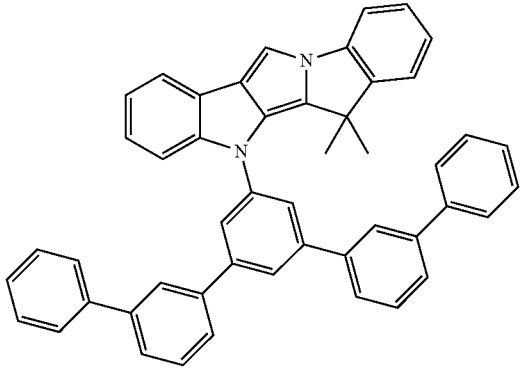

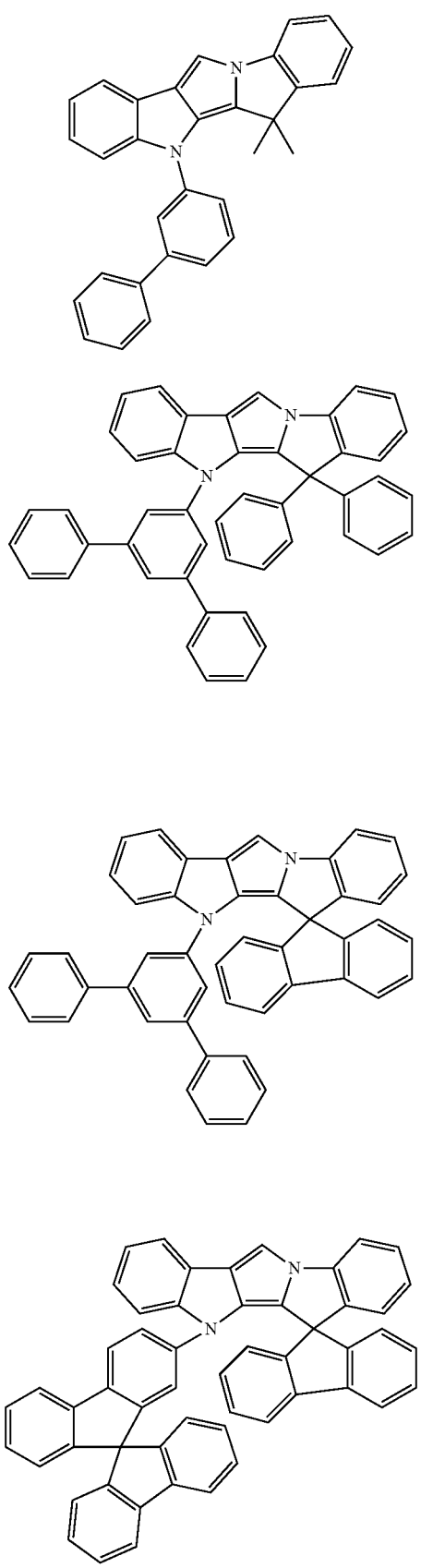
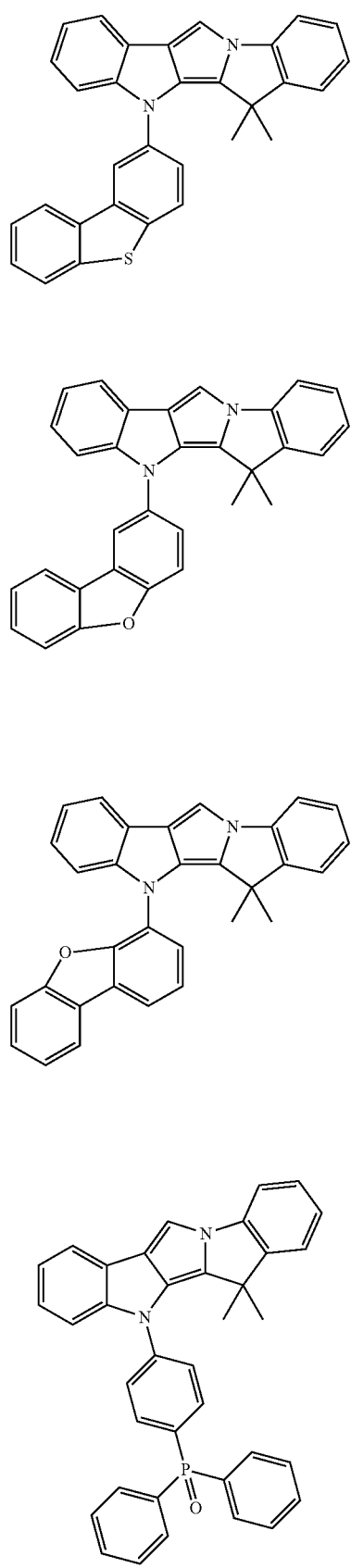

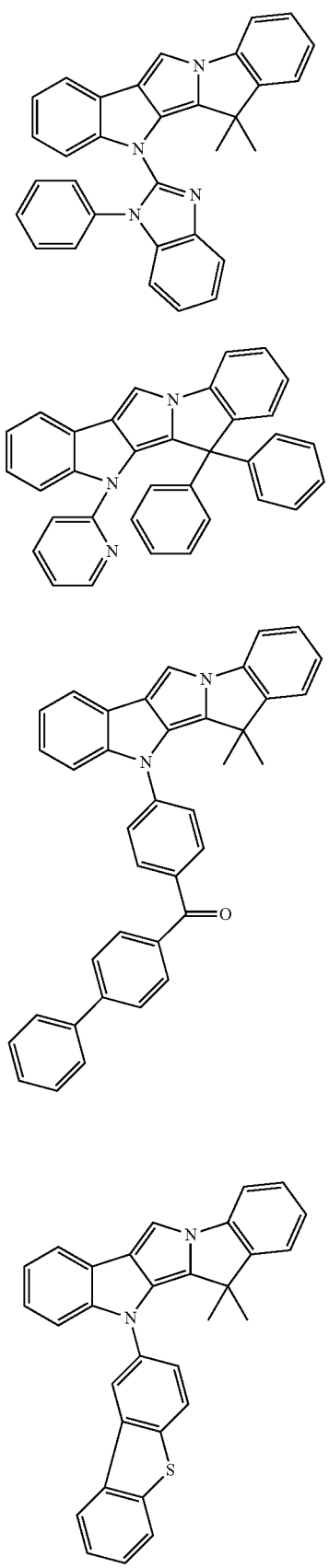
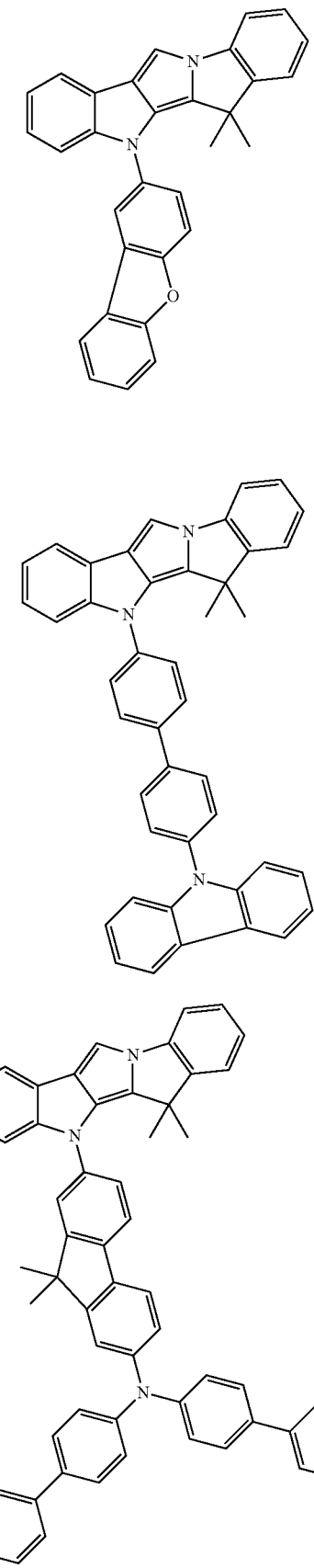

81
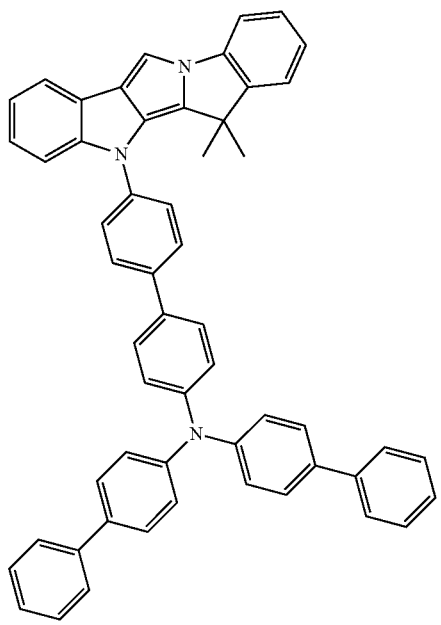
82
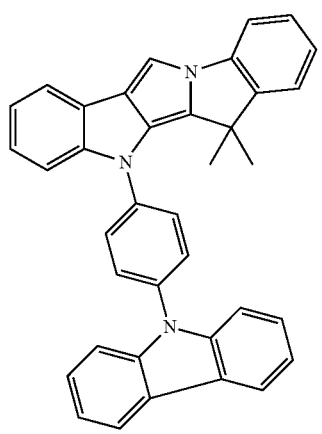
83
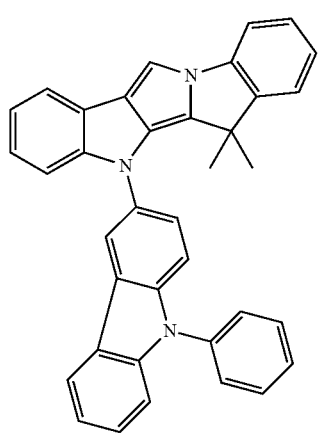
84
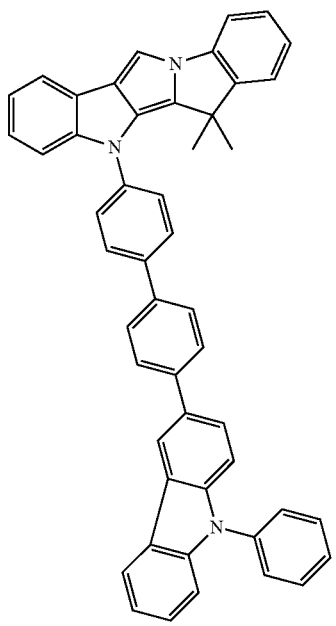
85
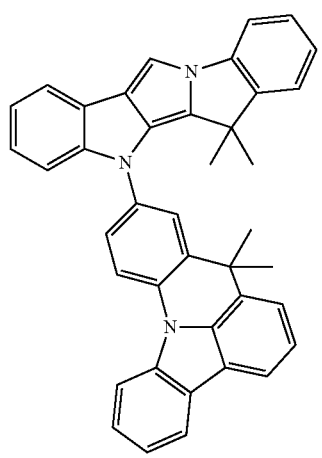
86
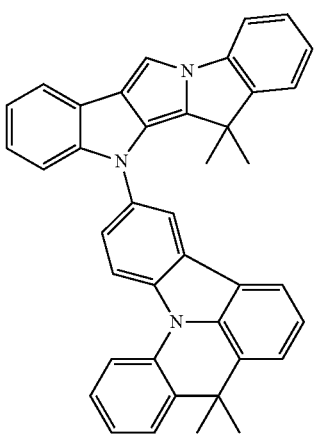

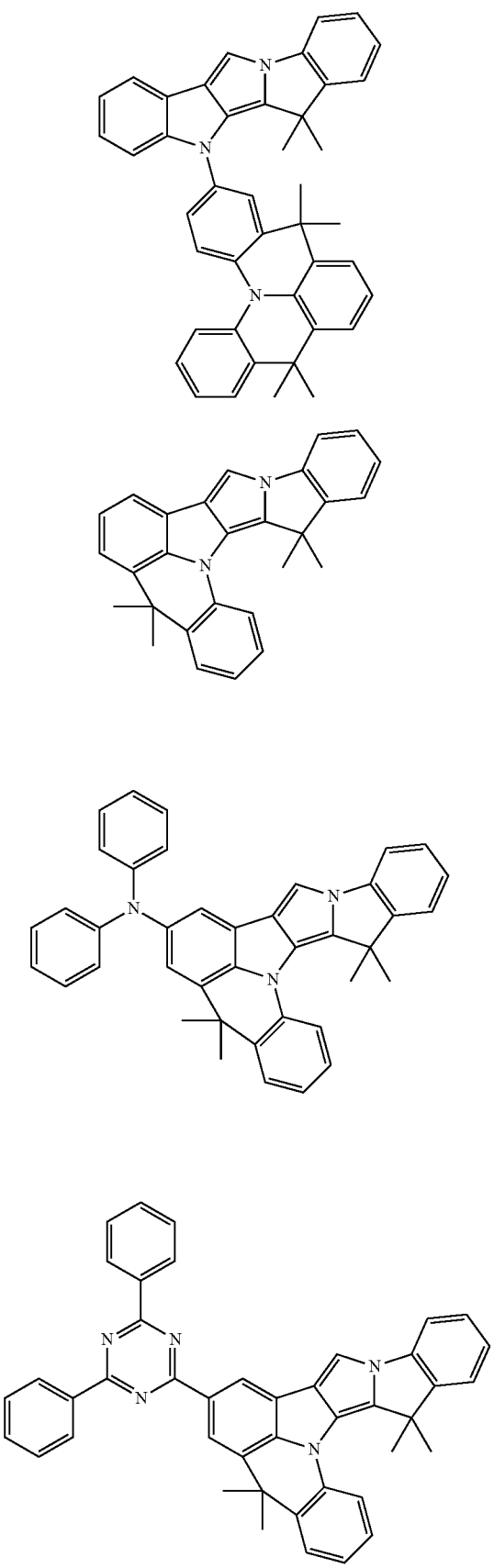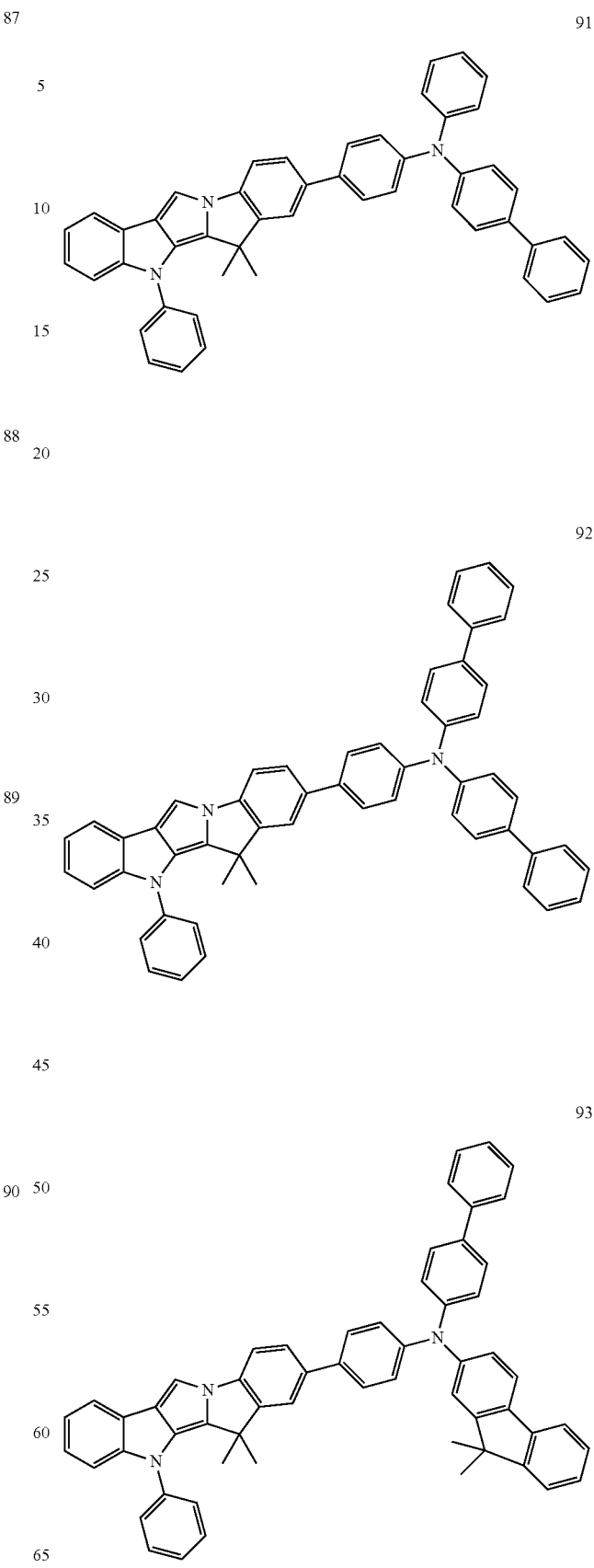

94
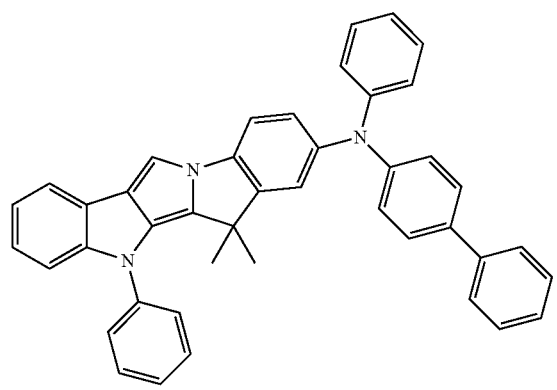
95
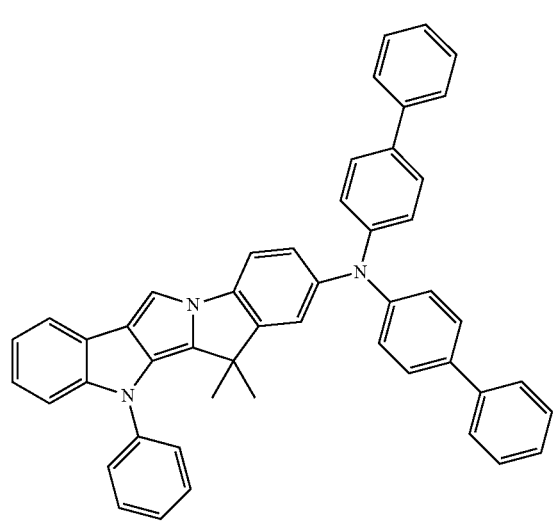
96
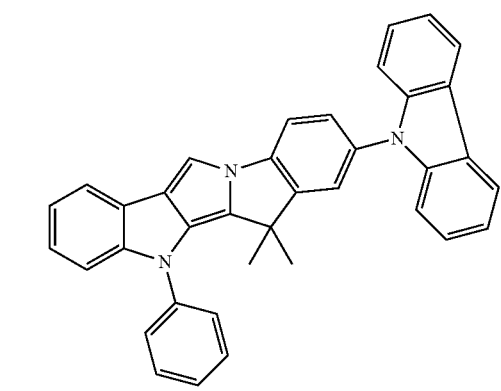
97
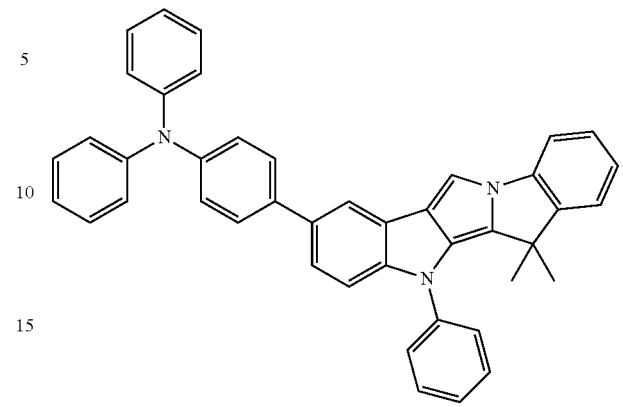
98
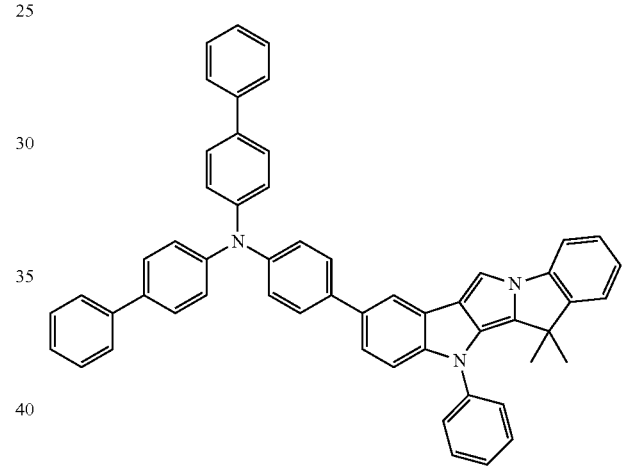
99
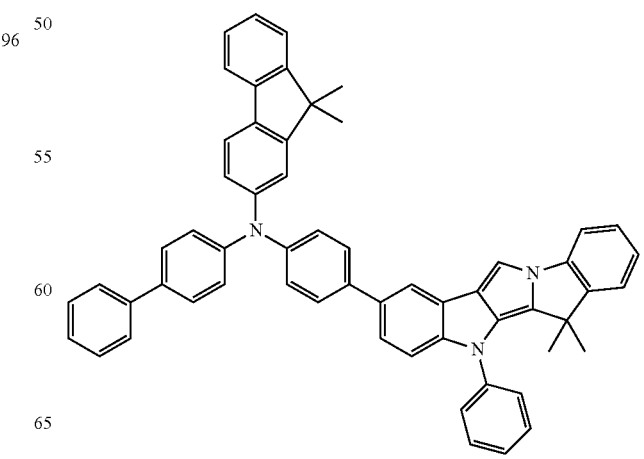

-continued
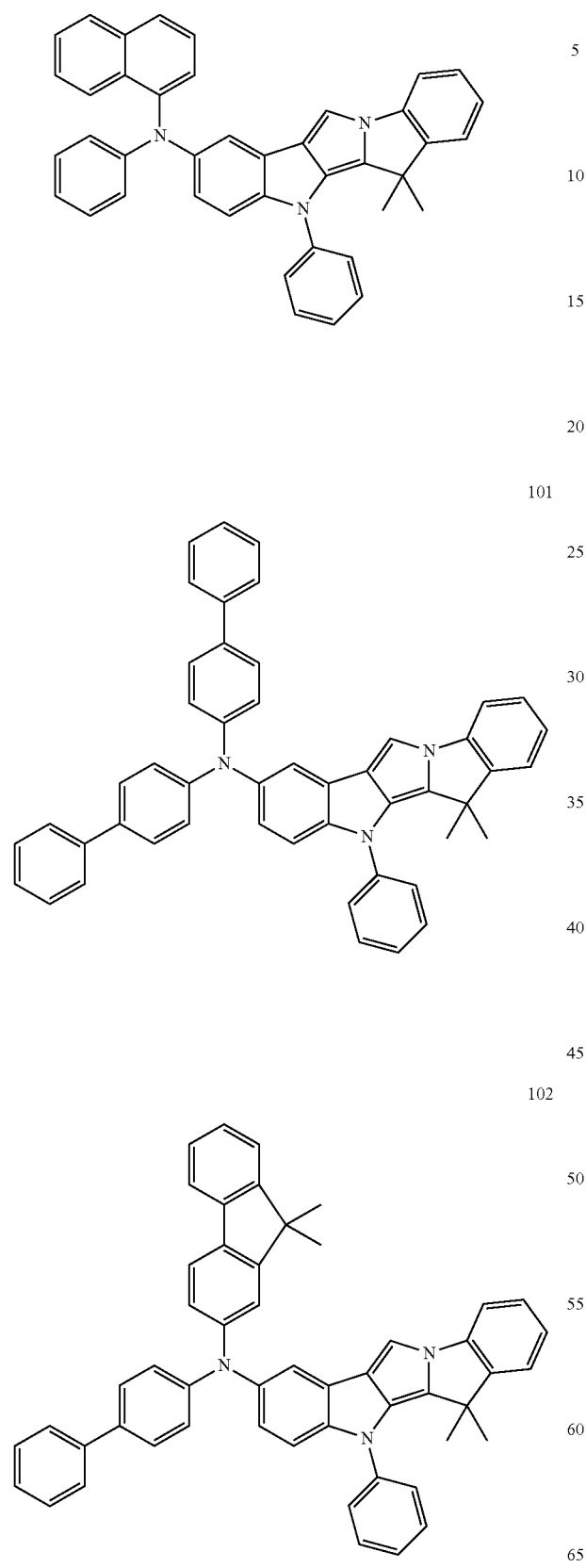
-continued
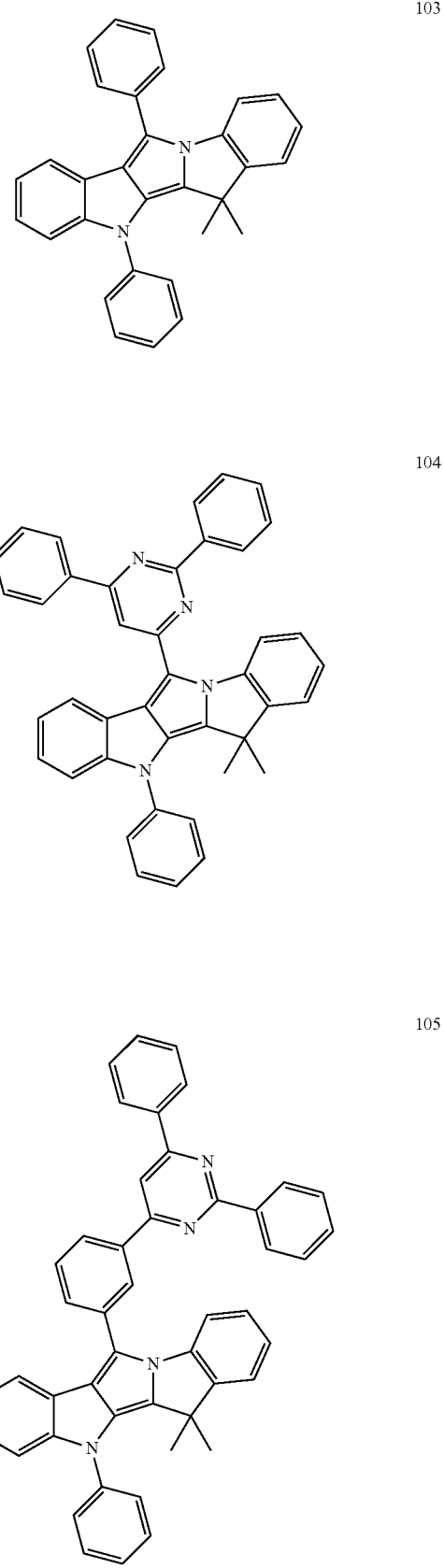

106
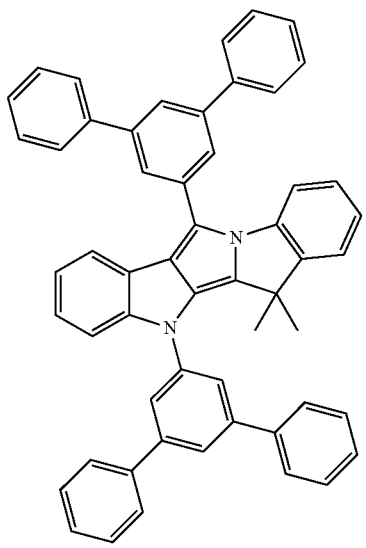
107
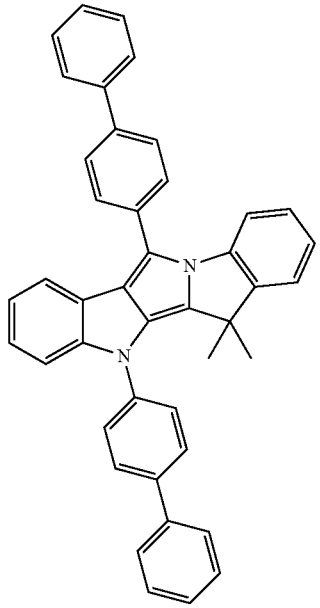
108
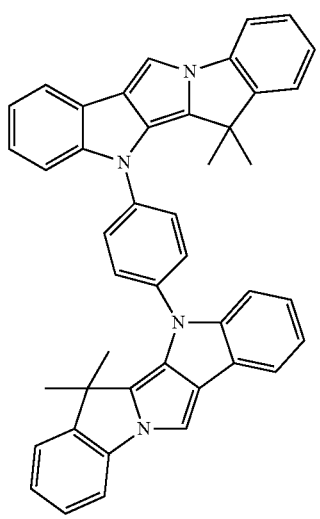
109
110
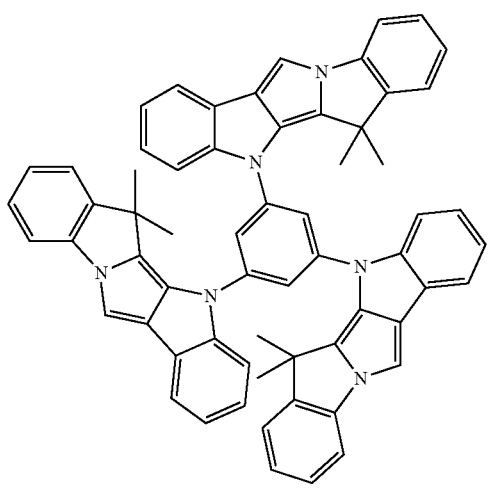

-continued
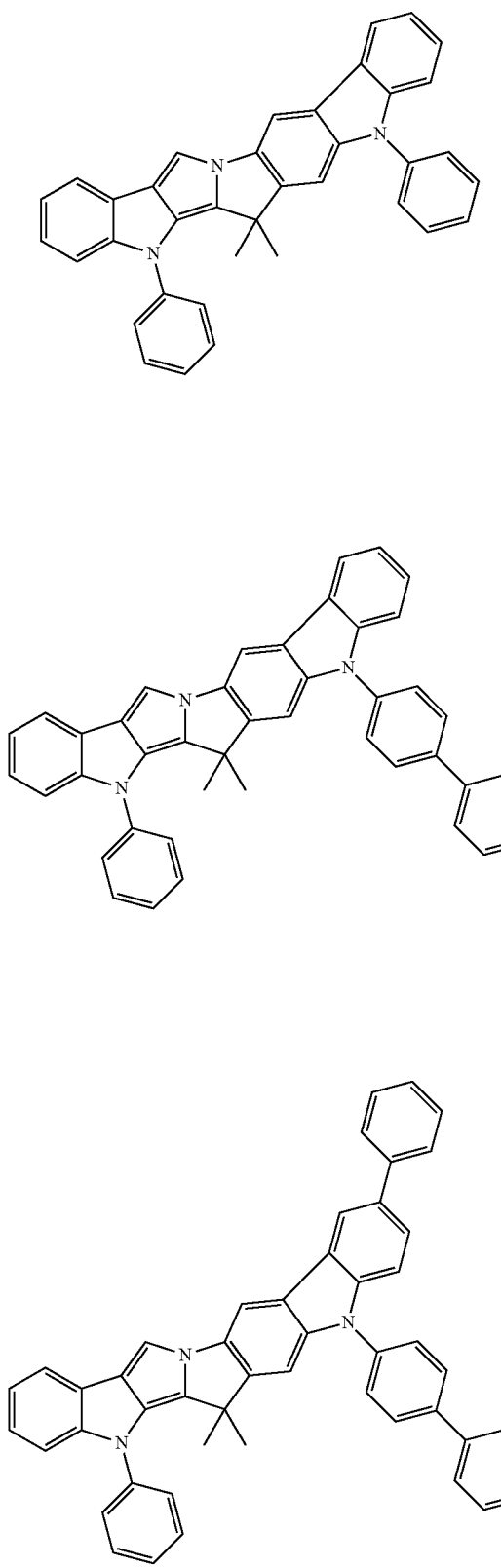
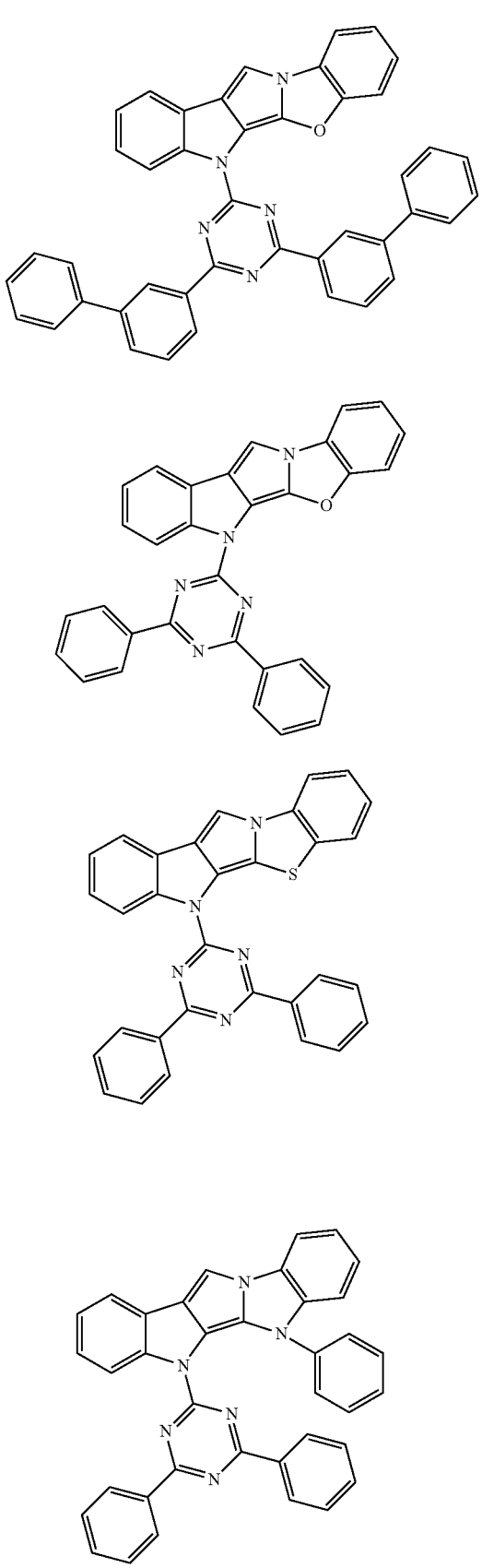

118
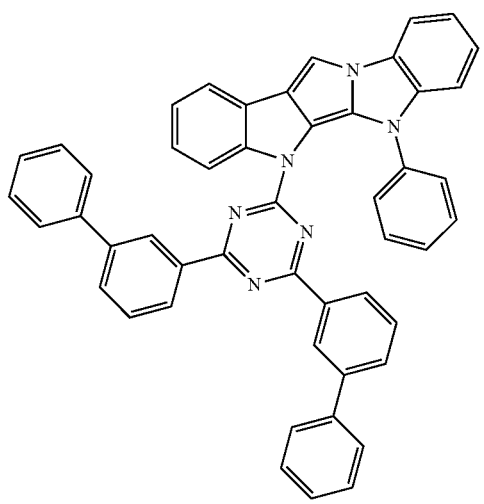
119
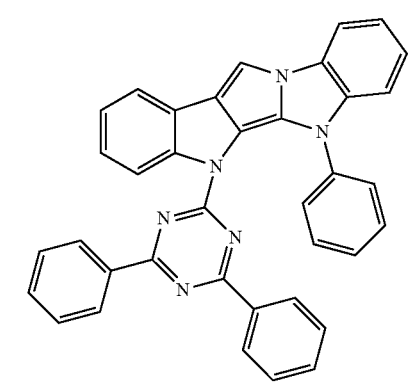
120
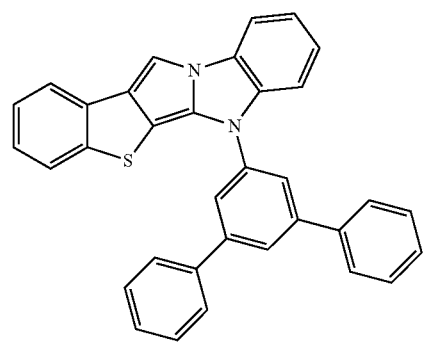
121
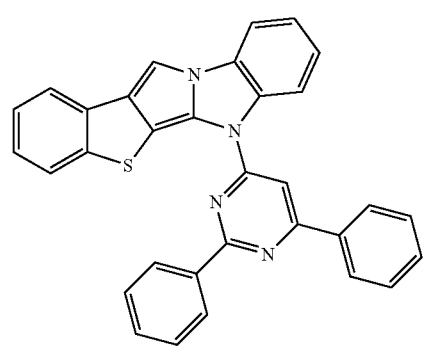
122
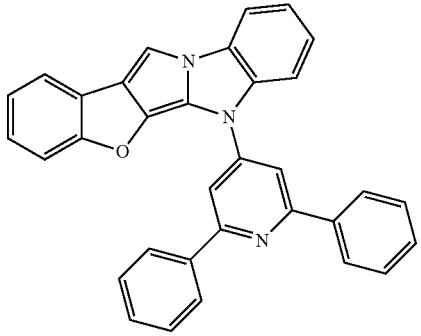
123
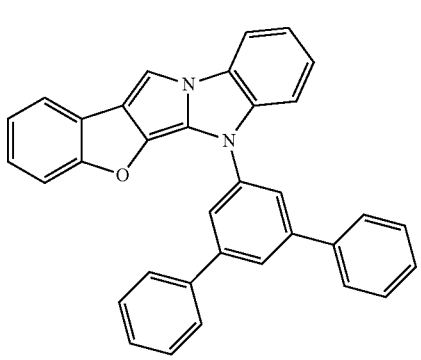
124
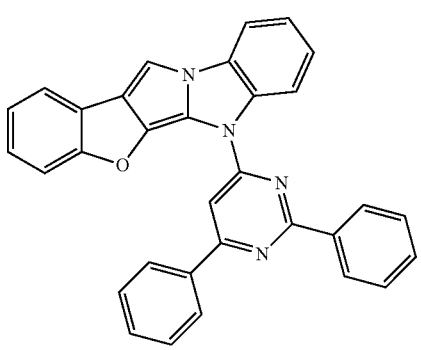
125
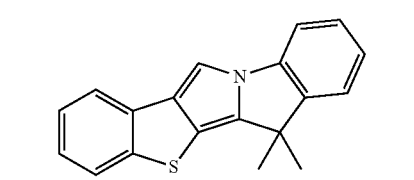
126
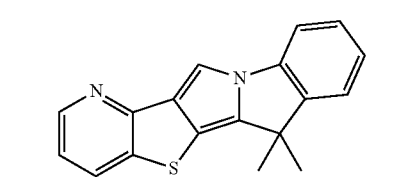
127
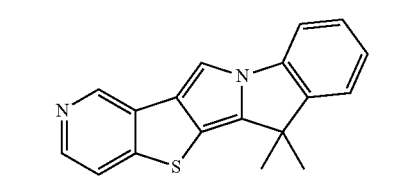

128 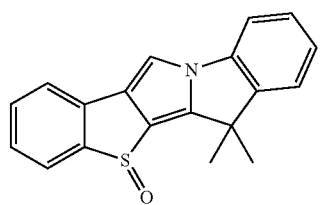
129 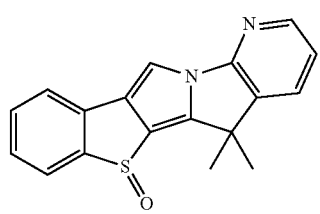
130 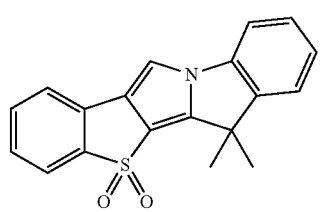
131 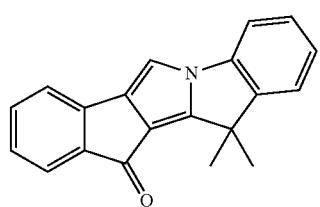
132 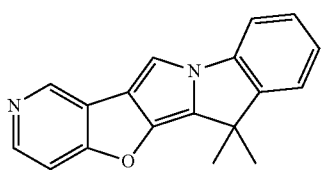
133 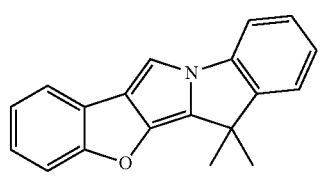
134 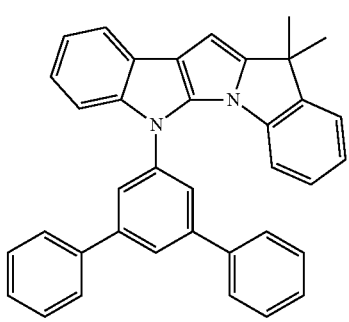
135 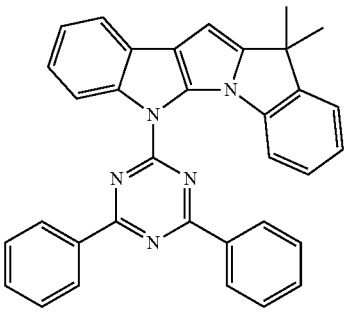
136 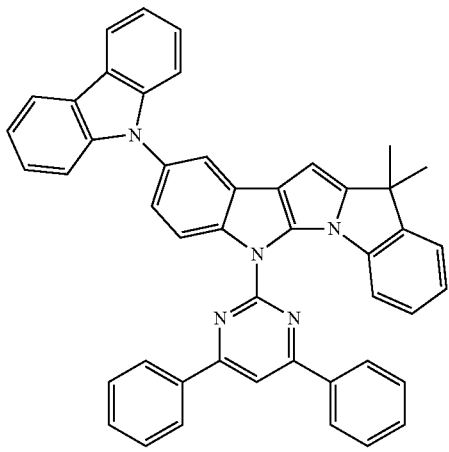
137 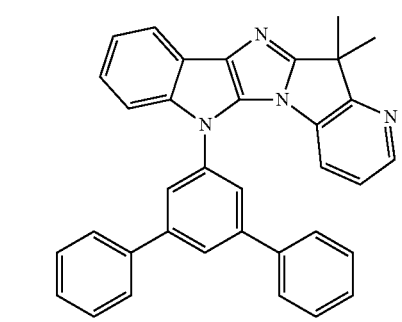
138 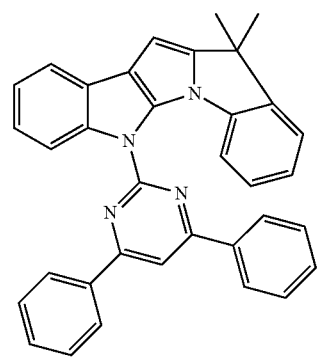

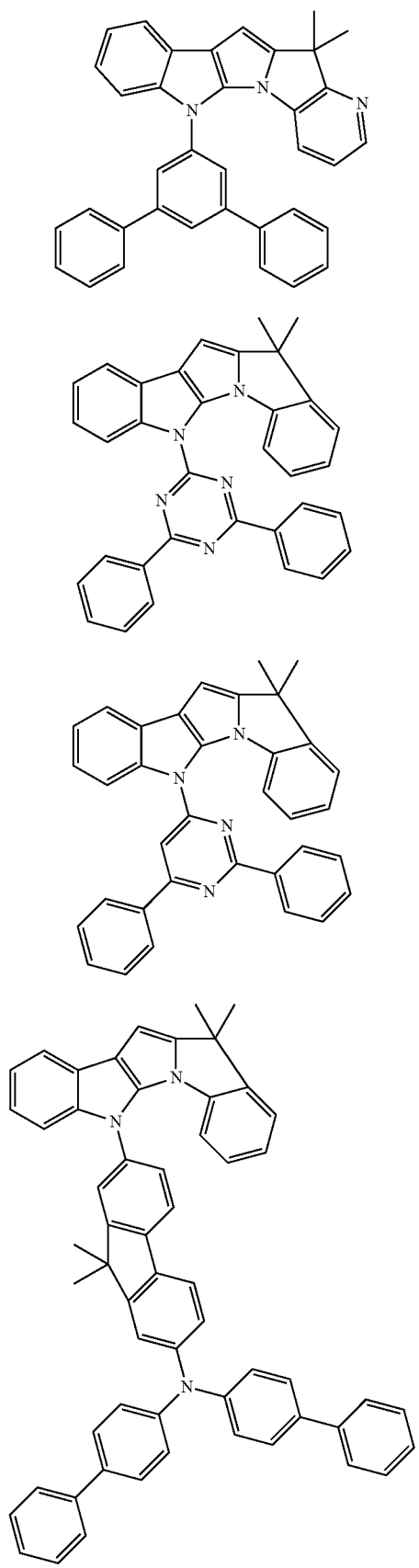
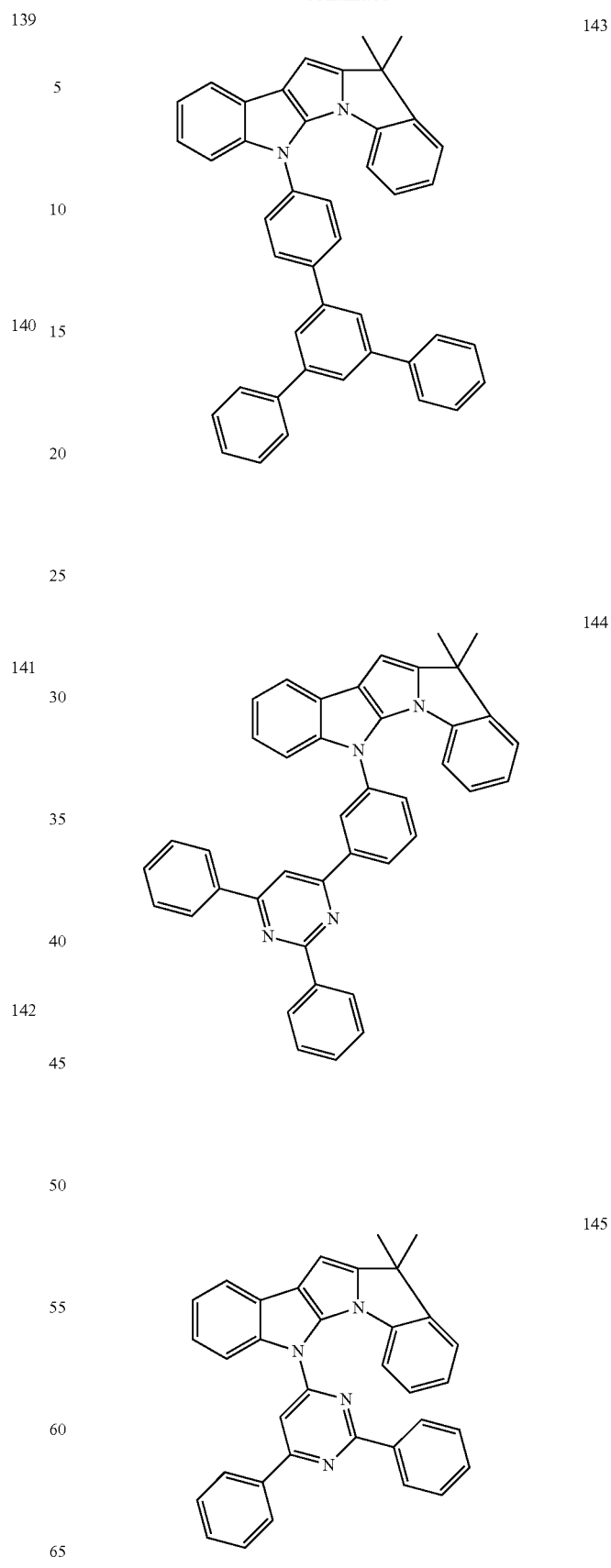

146
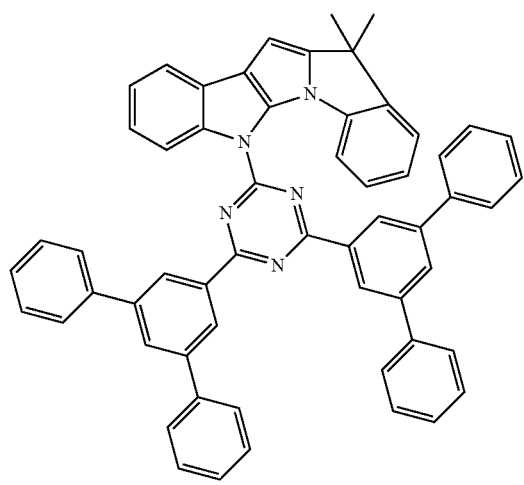
5
10
15
20
147
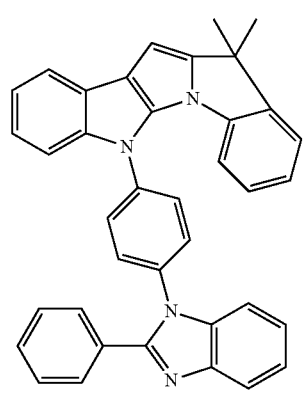
30
35
40
45
147
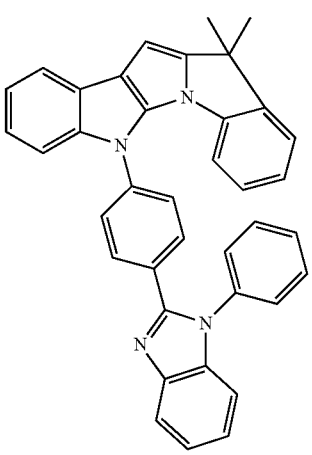
55
60
65
149
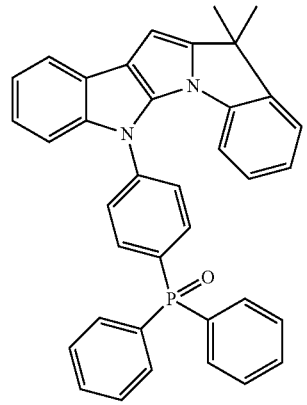
150
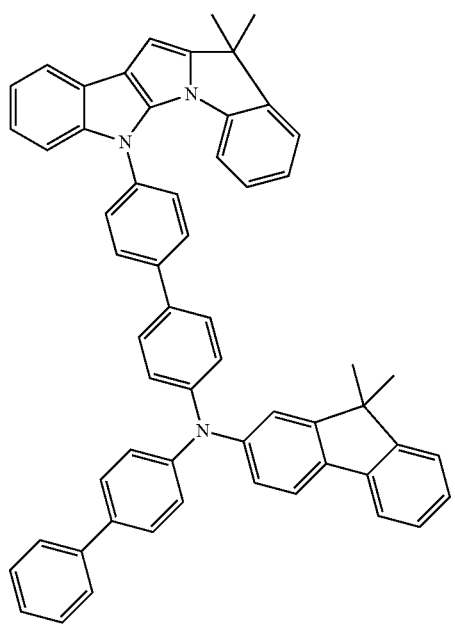
151
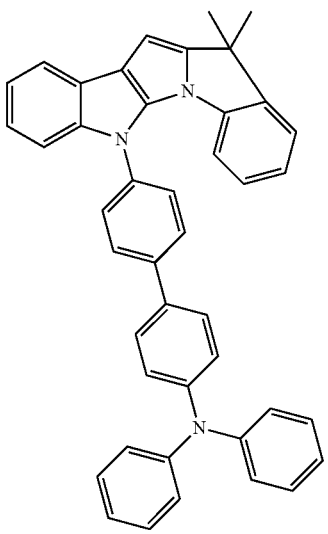

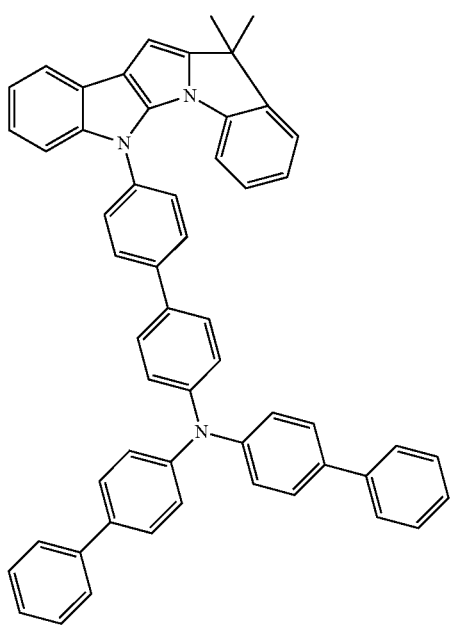
152
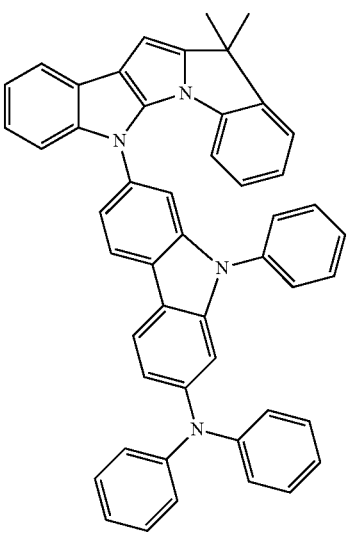
154
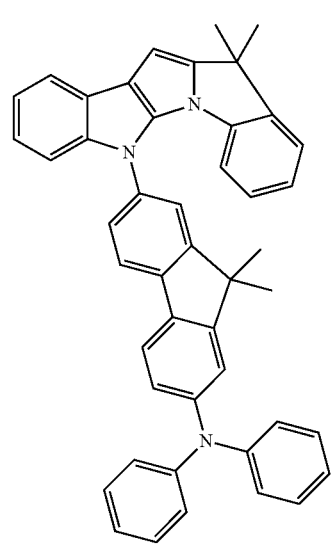
153
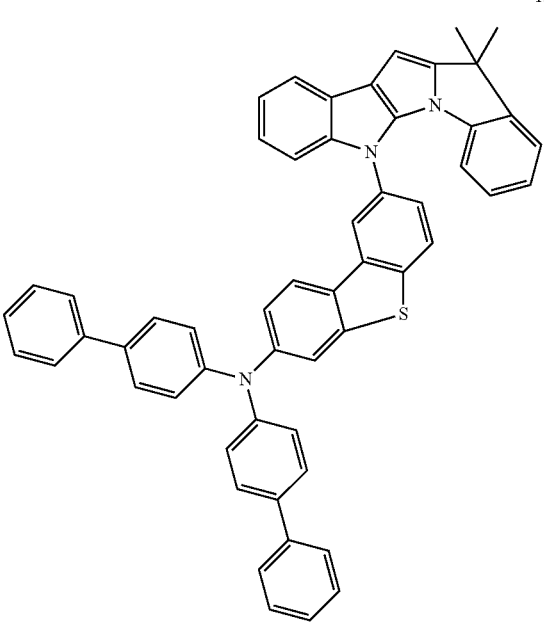
155

156
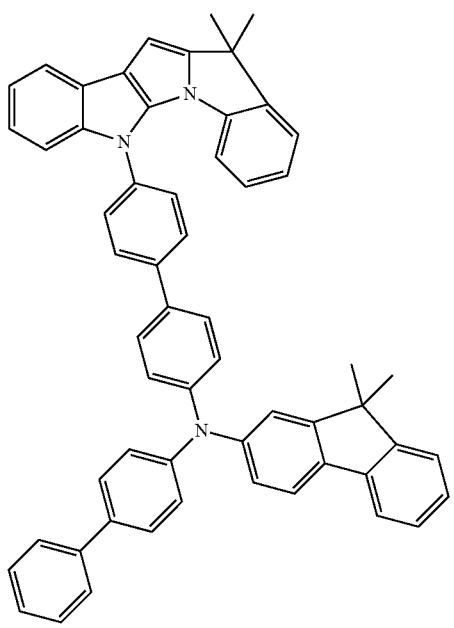
157
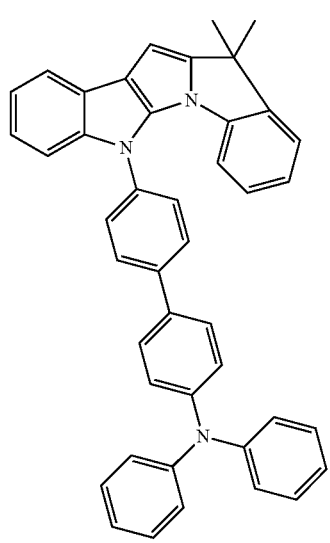
158
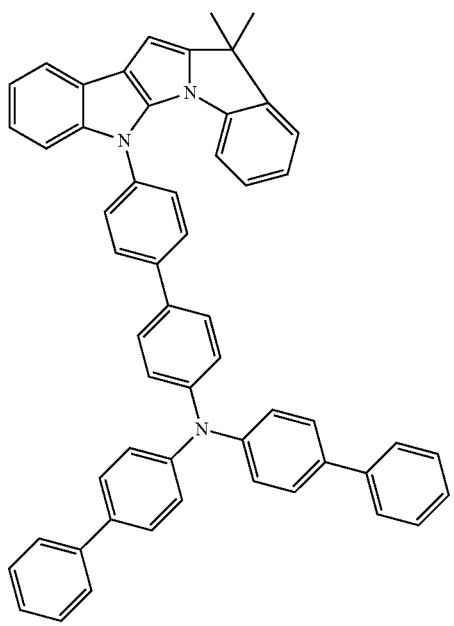
159
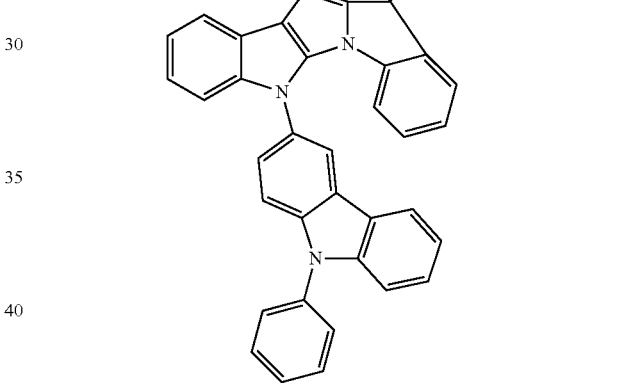
160
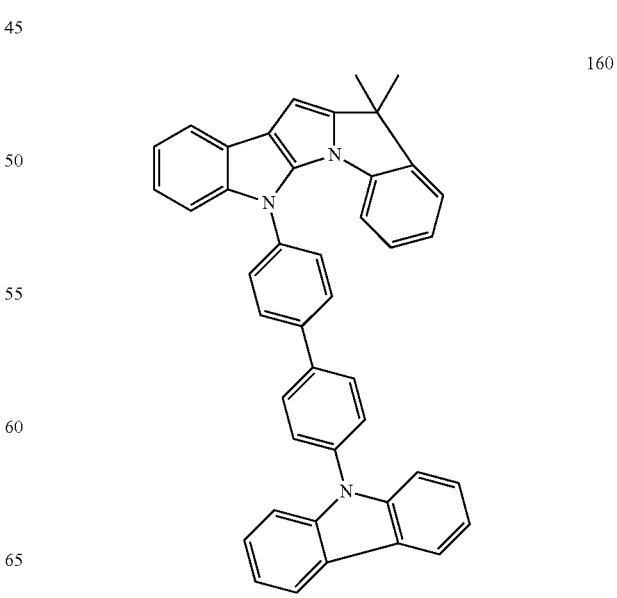

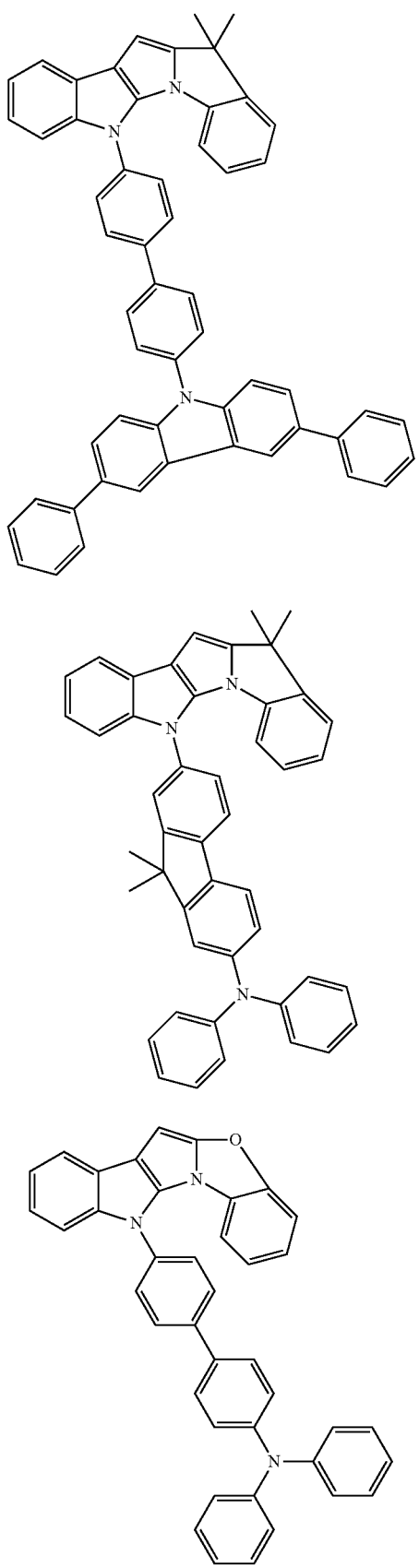
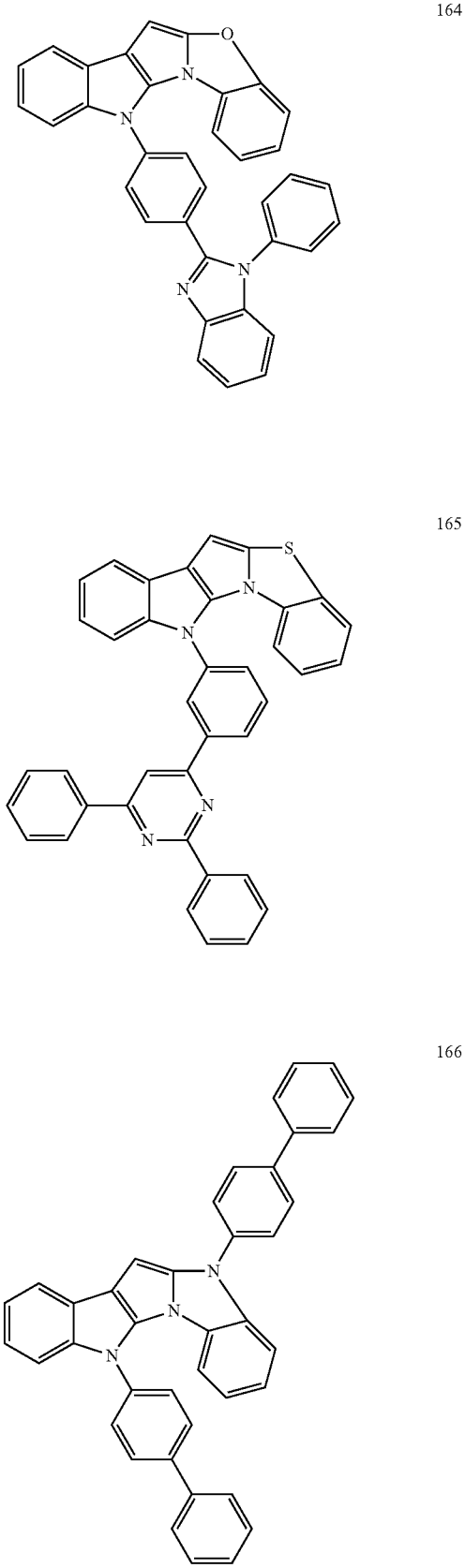

167

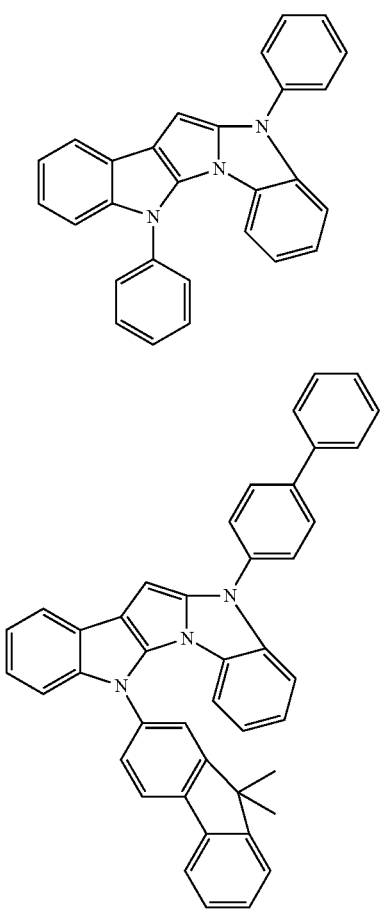

168

The compounds according to the invention can be synthesised by organic synthetic methods known to the person skilled in the art, such as, for example, Hartwig-Buchwald reaction and Friedel-Crafts alkylation.

Various synthetic routes by which compounds according to the invention can be prepared are shown below as examples. The compounds obtained may be substituted at any desired positions, in accordance with the definition of the compounds of the formula (I), (II) or (III). For clarity, the substituents are not depicted explicitly in the following schemes, i.e. only skeletons are shown. The way in which the desired substituents can be introduced, if necessary with the aid of protecting-group technique, is known to the person skilled in the art in the area of organic synthesis.

Scheme 1 shows a process for the synthesis of a compound of the formula (I) according to the invention which contains a group NAr as divalent group X and which contains a group $CR_2$ as divalent group Y. This process starts from the commercially available pyrroloindole compound shown, which is reacted with a phenylboronic acid derivative, so that coupling takes place between the pyrrole nitrogen atom and the phenyl group. The carboxylate radical present in the vicinal position to the pyrrole nitrogen atom is then reduced to the tertiary alcohol by the addition reaction of an organolithium compound, and a ring-closure reaction with the phenyl group is carried out under acidic conditions. An aryl or heteroaryl group can then be introduced on the nitrogen atom of the indole in a Hartwig-Buchwald coupling.

Scheme 1

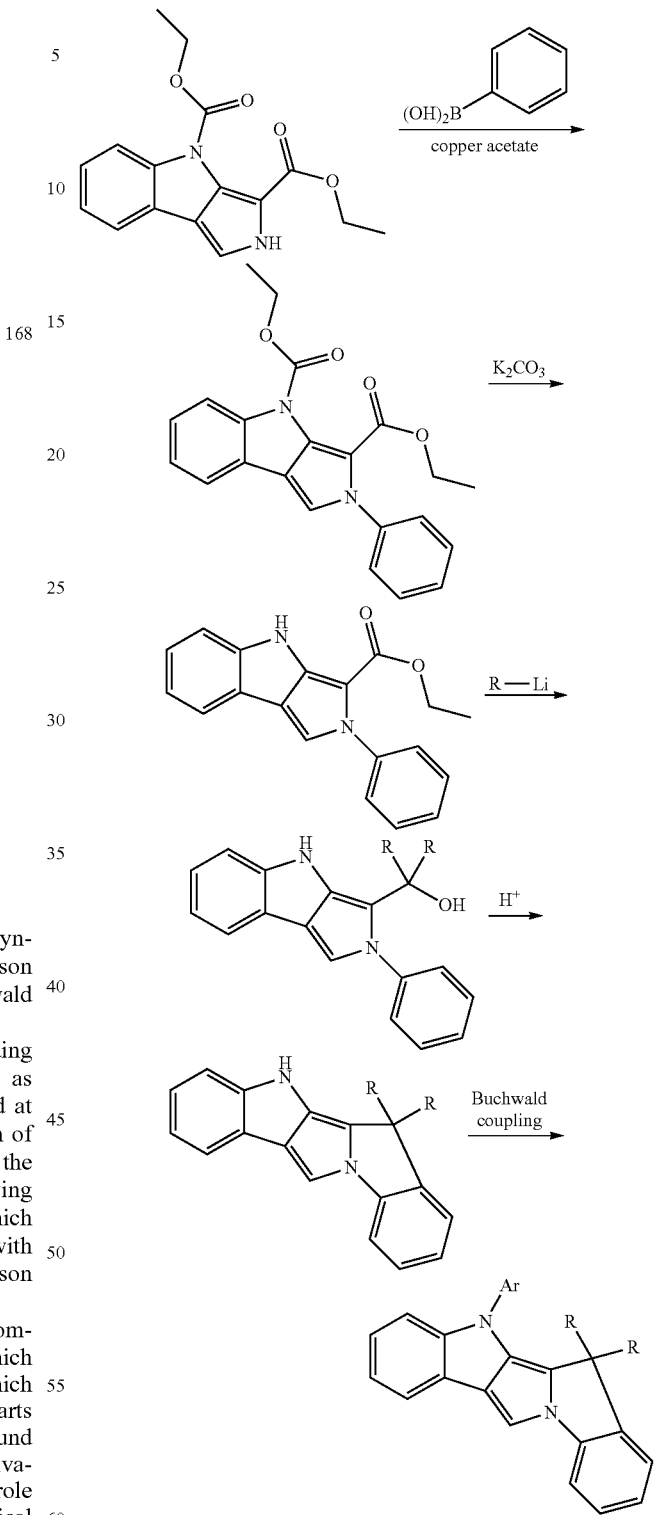

R = organic radical
Ar = optionally substituted aryl or heteroaryl group

Scheme 2 shows a process for the synthesis of a compound of the formula (I) according to the invention which contains a group NAr as divalent group X and which contains a group O or S as divalent group Y. The process differs from that shown in Scheme 1 essentially through the fact that a different ring-closure reaction is employed for the introduction of the group Y. The starting material employed is a pyrroloindole derivative which contains a fluorine atom in the vicinal position to the pyrrole nitrogen atom. A phenyl group which contains an —OH or —SH group in the corresponding position is coupled onto the pyrrole nitrogen atom. The ring-closure reaction now takes place between the —OH or —SH group and the fluorine-substituted carbon atom of the pyrrole ring under strongly basic conditions (NaH). The desired O or S bridge is produced in the process.

Scheme 3 shows a process for the synthesis of a compound of the formula (II) according to the invention. The synthetic route is substantially analogous to that shown in Scheme 1, with the difference that the starting material employed is an isomeric pyrroloindole derivative.

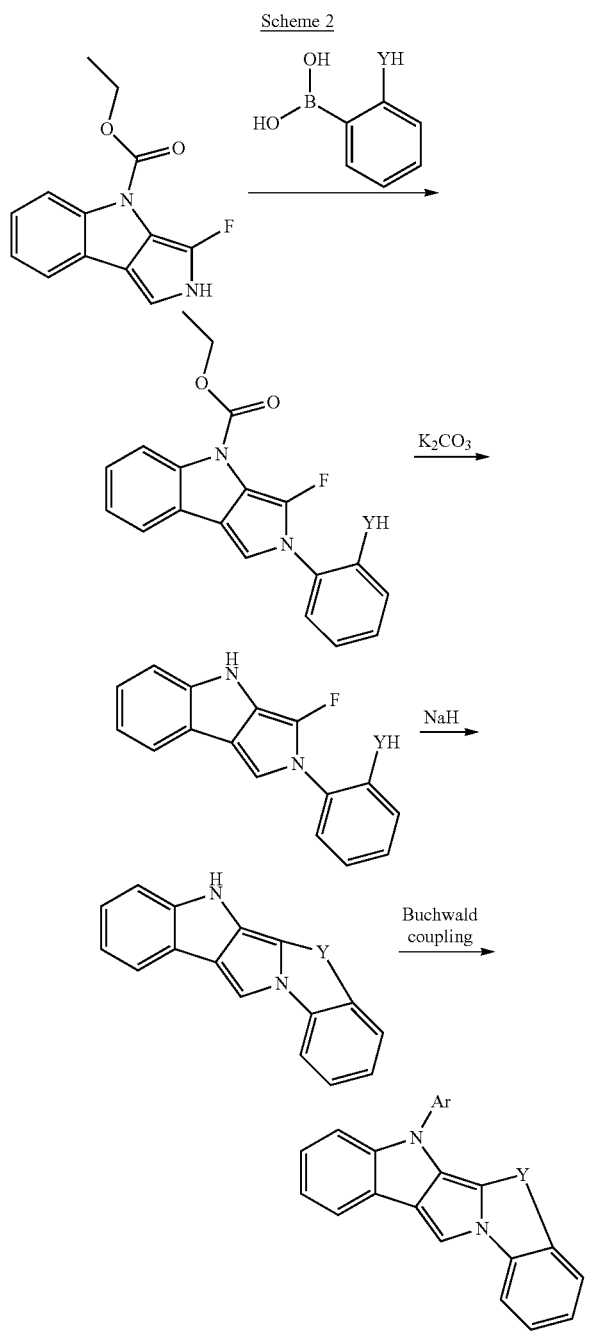

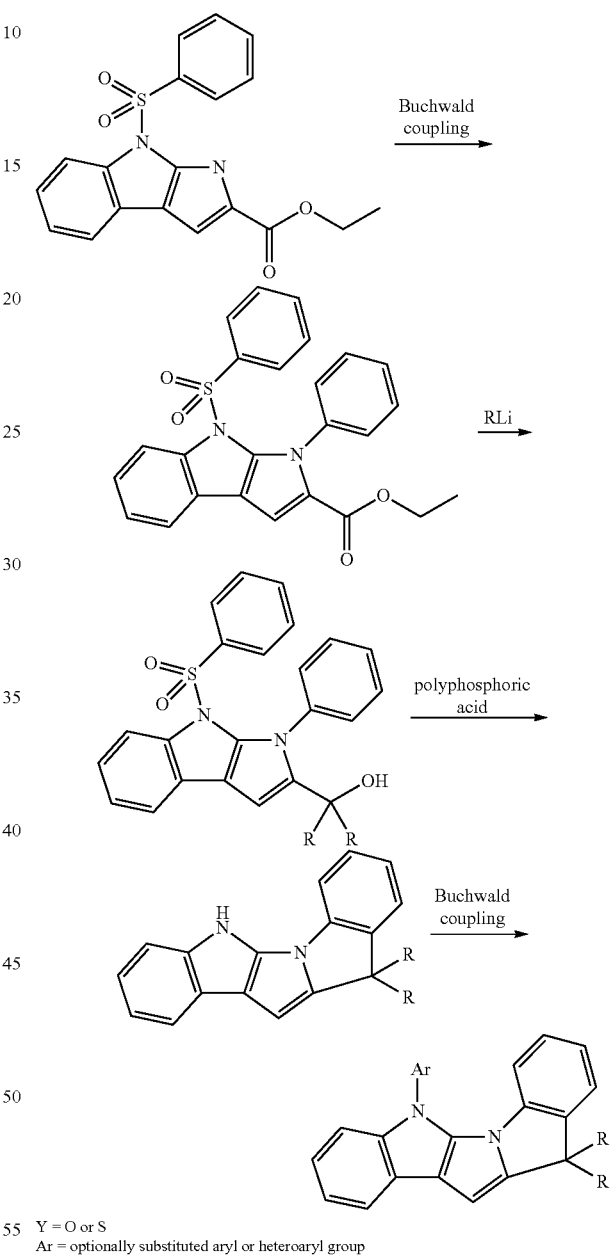

Y = O or S
Ar = optionally substituted aryl or heteroaryl group

The synthetic routes described above are merely intended to serve as examples. The person skilled in the art will be able to fall back on alternative synthetic processes for the synthesis of the compounds according to the invention if this appears advantageous to him under the given circumstances. Furthermore, he will be able to extend and/or modify the syntheses shown, utilising his general expert knowledge in the area of organic synthetic chemistry, in order to prepare compounds according to the invention.

The invention thus furthermore relates to a process for the preparation of a compound of the formula (I), (II) or (III), comprising at least the following steps:
(a) a coupling reaction between the pyrrole nitrogen atom and an aryl or heteroaryl group; and
(b) a ring-closure reaction between the pyrrole ring and the aryl or heteroaryl group coupled in step (a).

The compounds according to the invention described above, in particular compounds which are substituted by reactive leaving groups, such as bromine, iodine, chlorine, boronic acid or boronic acid ester, can be used as monomers for the production of corresponding oligomers, dendrimers or polymers. The oligomerisation or polymerisation here is preferably carried out via the halogen functionality or the boronic acid functionality.

The invention therefore furthermore relates to oligomers, polymers or dendrimers comprising one or more compounds of the formula (I), (II) or (III), where the bond(s) to the polymer, oligomer or dendrimer may be localised at any desired positions in formula (I), (II) or (III) substituted by $R^1$ or $R^2$. Depending on the linking of the compound of the formula (I), (II) or (III), the compound is part of a side chain of the oligomer or polymer or part of the main chain. An oligomer in the sense of this invention is taken to mean a compound which is built up from at least three monomer units. A polymer in the sense of the invention is taken to mean a compound which is built up from at least ten monomer units. The polymers, oligomers or dendrimers according to the invention may be conjugated, partially conjugated or non-conjugated. The oligomers or polymers according to the invention may be linear, branched or dendritic. In the structures linked in a linear manner, the units of the formula (I), (II) or (III) may be linked directly to one another or linked to one another via a divalent group, for example via a substituted or unsubstituted alkylene group, via a heteroatom or via a divalent aromatic or heteroaromatic group. In branched and dendritic structures, three or more units of the formula (I), (II) or (III) may, for example, be linked via a trivalent or polyvalent group, for example via a trivalent or polyvalent aromatic or heteroaromatic group, to give a branched or dendritic oligomer or polymer. The same preferences as described above for compounds of the formula (I), (II) or (III) apply to the recurring units of the formula (I), (II) or (III) in oligomers, dendrimers and polymers.

For the preparation of the oligomers or polymers, the monomers according to the invention are homopolymerised or copolymerised with further monomers. Suitable and preferred comonomers are selected from fluorenes (for example in accordance with EP 842208 or WO 00/22026), spirobifluorenes (for example in accordance with EP 707020, EP 894107 or WO 06/061181), para-phenylenes (for example in accordance with WO 92/18552), carbazoles (for example in accordance with WO 04/070772 or WO 04/113468), thiophenes (for example in accordance with EP 1028136), dihydrophenanthrenes (for example in accordance with WO 05/014689 or WO 07/006,383), cis- and trans-indenofluorenes (for example in accordance with WO 04/041901 or WO 04/113412), ketones (for example in accordance with WO 05/040302), phenanthrenes (for example in accordance with WO 05/104264 or WO 07/017,066) or also a plurality of these units. The polymers, oligomers and dendrimers usually also contain further units, for example emitting (fluorescent or phosphorescent) units, such as, for example, vinyltriarylamines (for example in accordance with WO 07/068,325) or phosphorescent metal complexes (for example in accordance with WO 06/003000), and/or charge-transport units, in particular those based on triarylamines.

The polymers, oligomers and dendrimers according to the invention have advantageous properties, in particular long lifetimes, high efficiencies and good colour coordinates.

The polymers and oligomers according to the invention are generally prepared by polymerisation of one or more types of monomer, at least one monomer of which results in recurring units of the formula (I), (II) or (III) in the polymer. Suitable polymerisation reactions are known to the person skilled in the art and are described in the literature. Particularly suitable and preferred polymerisation reactions which result in C—C or C—N links are the following:
(A) SUZUKI polymerisation;
(B) YAMAMOTO polymerisation;
(C) STILLE polymerisation; and
(D) HARTWIG-BUCHWALD polymerisation.

The way in which the polymerisation can be carried out by these methods and the way in which the polymers can then be separated off from the reaction medium and purified is known to the person skilled in the art and is described in detail in the literature, for example in WO 2003/048225, WO 2004/037887 and WO 2004/037887.

The present invention thus also relates to a process for the preparation of the polymers, oligomers and dendrimers according to the invention, which is characterised in that they are prepared by SUZUKI polymerisation, YAMAMOTO polymerisation, STILLE polymerisation or HARTWIG-BUCHWALD polymerisation. The dendrimers according to the invention can be prepared by processes known to the person skilled in the art or analogously thereto. Suitable processes are described in the literature, such as, for example, in Frechet, Jean M. J.; Hawker, Craig J., "Hyperbranched polyphenylene and hyperbranched polyesters: new soluble, three-dimensional, reactive polymers", Reactive & Functional Polymers (1995), 26(1-3), 127-36; Janssen, H. M.; Meijer, E. W., "The synthesis and characterization of dendritic molecules", Materials Science and Technology (1999), 20 (Synthesis of Polymers), 403-458; Tomalia, Donald A., "Dendrimer molecules", Scientific American (1995), 272(5), 62-6; WO 2002/067343 A1 and WO 2005/026144 A1.

For the processing of the compounds according to the invention from liquid phase, for example by spin coating or by printing processes, formulations of the compounds according to the invention are necessary. These formulations can be, for example, solutions, dispersions or mini-emulsions.

The invention therefore furthermore relates to a formulation, in particular a solution, dispersion or mini-emulsion, comprising at least one compound of the formula (I), (II) or (III) or at least one polymer, oligomer or dendrimer containing at least one unit of the formula (I), (II) or (III) and at least one solvent, preferably an organic solvent. The way in which solutions of this type can be prepared is known to the person skilled in the art and is described, for example, in the applications WO 2002/072714 and WO 2003/019694 and the literature cited therein.

The compounds of the formula (I), (II) or (III) according to the invention are suitable for use in electronic devices, in particular in organic electroluminescent devices (OLEDs). Depending on the substitution, the compounds are employed in different functions and/or layers.

For example, compounds according to the invention which contain electron-deficient groups, such as six-membered heteroaryl ring groups containing one or more nitrogen atoms or five-membered heteroaryl ring groups containing two or more heteroatoms, are particularly suitable for use as matrix material for phosphorescent dopants, as electron-transport material or as hole-blocking material.

Furthermore, compounds according to the invention which are substituted by aromatic or heteroaromatic ring systems having 5 to 20 aromatic ring atoms, in particular by aromatic ring systems having 12 to 20 aromatic ring atoms, and/or by one or more arylamino groups are particularly suitable for use as hole-transport materials or for use as fluorescent dopants.

The compounds according to the invention are preferably employed as matrix material in an emitting layer, as hole-transport material in a hole-transport layer or as electron-transport material in an electron-transport layer. The compounds according to the invention are furthermore preferably employed in a hole-injection layer. However, they can also be employed in other layers and/or functions, for example as fluorescent dopants in an emitting layer or as hole- or electron-blocking materials.

The invention therefore furthermore relates to the use of the compounds according to the invention in electronic devices. The electronic devices here are preferably selected from the group consisting of organic integrated circuits (O—ICs), organic field-effect transistors (O-FETs), organic thin-film transistors (O-TFTs), organic light-emitting transistors (O-LETs), organic solar cells (O—SCs), organic optical detectors, organic photoreceptors, organic field-quench devices (O-FQDs), light-emitting electrochemical cells (LECs), organic laser diodes (O-lasers) and particularly preferably selected from organic electroluminescent devices (OLEDs).

The invention again furthermore relates to electronic devices comprising at least one compound of the formula (I), (II) or (III). The electronic devices here are preferably selected from the devices mentioned above. Particular preference is given to organic electroluminescent devices comprising an anode, a cathode and at least one emitting layer, characterised in that at least one organic layer, which may be an emitting layer, an electron-transport layer or another layer, comprises at least one compound of the formula (I), (II) or (III).

Apart from the cathode, anode and emitting layer, the organic electroluminescent device may also comprise further layers. These are selected, for example, from in each case one or more hole-injection layers, hole-transport layers, hole-blocking layers, electron-transport layers, electron-injection layers, electron-blocking layers, exciton-blocking layers, charge-generation layers (IDMC 2003, Taiwan; Session 21 OLED (5), T. Matsumoto, T. Nakada, J. Endo, K. Mori, N. Kawamura, A. Yokoi, J. Kido, *Multiphoton Organic EL Device Having Charge Generation Layer*), coupling-out layers and/or organic or inorganic p/n junctions. However, it should be pointed out that each of these layers does not necessarily have to be present and the choice of layers is always dependent on the compounds used and in particular also on whether the electroluminescent device is fluorescent or phosphorescent. The compounds preferably employed in the respective layers and functions are explicitly disclosed in later sections.

It is preferred in accordance with the invention for the compound of the formula (I), (II) or (III) to be employed in an electronic device comprising one or more phosphorescent dopants. The compound can be used in various layers here, preferably in an electron-transport layer, a hole-transport layer, a hole-injection layer or in the emitting layer. However, the compound of the formula (I), (II) or (III) can also be employed in accordance with the invention in an electronic device comprising one or more fluorescent dopants and no phosphorescent dopants.

Suitable phosphorescent dopants (=triplet emitters) are, in particular, compounds which emit light, preferably in the visible region, on suitable excitation and in addition contain at least one atom having an atomic number greater than 20, preferably greater than 38 and less than 84, particularly preferably greater than 56 and less than 80. The phosphorescent dopants used are preferably compounds which contain copper, molybdenum, tungsten, rhenium, ruthenium, osmium, rhodium, iridium, palladium, platinum, silver, gold or europium, in particular compounds which contain iridium, platinum or copper.

For the purposes of the present invention, all luminescent iridium, platinum or copper complexes are regarded as phosphorescent compounds.

Examples of the phosphorescent dopants described above are revealed by the applications WO 2000/70655, WO 2001/41512, WO 2002/02714, WO 2002/15645, EP 1191613, EP 1191612, EP 1191614, WO 2005/033244, WO 2005/019373 and US 2005/0258742. In general, all phosphorescent complexes as used in accordance with the prior art for phosphorescent OLEDs and as are known to the person skilled in the art in the area of organic electroluminescent devices are suitable. The person skilled in the art will also be able to employ further phosphorescent complexes without inventive step in combination with the compounds according to the invention in organic electroluminescent devices.

Further examples of suitable phosphorescent dopants are revealed by the table following in a later section.

In a preferred embodiment of the present invention, the compounds of the formula (I), (II) or (III) are employed as matrix material in combination with one or more dopants, preferably phosphorescent dopants. The compounds are particularly suitable for use as matrix material if they contain one or more electron-deficient groups, such as, for example, six-membered heteroaryl ring groups containing one or more nitrogen atoms or five-membered heteroaryl ring groups containing two or more nitrogen atoms.

A dopant in a system comprising a matrix material and a dopant is taken to mean the component whose proportion in the mixture is the smaller. Correspondingly, a matrix material is taken to mean the component whose proportion in the mixture is the greater in a system comprising a matrix material and a dopant.

The proportion of the matrix material in the emitting layer is in this case between 50.0 and 99.9% by vol., preferably between 80.0 and 99.5% by vol. and particularly preferably between 92.0 and 99.5% by vol. for fluorescent emitting layers and between 85.0 and 97.0% by vol. for phosphorescent emitting layers.

Correspondingly, the proportion of the dopant is between 0.1 and 50.0% by vol., preferably between 0.5 and 20.0% by vol. and particularly preferably between 0.5 and 8.0% by vol. for fluorescent emitting layers and between 3.0 and 15.0% by vol. for phosphorescent emitting layers.

An emitting layer of an organic electroluminescent device may also comprise systems comprising a plurality of matrix materials (mixed-matrix systems) and/or a plurality of dopants. In this case too, the dopants are generally the materials whose proportion in the system is the smaller and the matrix materials are the materials whose proportion in the system is the greater. In individual cases, however, the proportion of an individual matrix material in the system may be smaller than the proportion of an individual dopant.

In a further preferred embodiment of the invention, the compounds of the formula (I), (II) or (III) are used as a component of mixed-matrix systems. The mixed-matrix systems preferably comprise two or three different matrix materials, particularly preferably two different matrix materials. One of the two materials here is preferably a material having hole-transporting properties and the other material is a material having electron-transporting properties. The two different matrix materials here may be present in a ratio of 1:50 to 1:1, preferably 1:20 to 1:1, particularly preferably 1:10 to 1:1 and very particularly preferably 1:6 to 1:1. Mixed-matrix systems are preferably employed in phosphorescent organic electroluminescent devices.

The mixed-matrix systems may comprise one or more dopants. The dopant compound or the dopant compounds together have, in accordance with the invention, a proportion of 0.1 to 50.0% by vol. in the mixture as a whole and preferably a proportion of 0.5 to 20.0% by vol. in the mixture as a whole. Correspondingly, the matrix components together have a proportion of 50.0 to 99.9% by vol. in the mixture as a whole and preferably a proportion of 80.0 to 99.5% by vol. in the mixture as a whole.

Mixed-matrix systems are preferably employed in phosphorescent organic electroluminescent devices.

Particularly suitable matrix materials, which can be employed in combination with the compounds according to the invention as matrix components of a mixed-matrix system, are aromatic ketones, aromatic phosphine oxides or aromatic sulfoxides or sulfones, for example in accordance with WO 2004/013080, WO 2004/093207, WO 2006/005627 or WO 2010/006680, triarylamines, carbazole derivatives, for example CBP (N,N-biscarbazolylbiphenyl) or the carbazole derivatives disclosed in WO 2005/039246, US 2005/0069729, JP 2004/288381, EP 1205527 or WO 2008/086851, indolocarbazole derivatives, for example in accordance with WO 2007/063754 or WO 2008/056746, azacarbazole derivatives, for example in accordance with EP 1617710, EP 1617711, EP 1731584, JP 2005/347160, bipolar matrix materials, for example in accordance with WO 2007/137725, silanes, for example in accordance with WO 2005/111172, azaboroles or boronic esters, for example in accordance with WO 2006/117052, triazine derivatives, for example in accordance with WO 2010/015306, WO 2007/063754 or WO 2008/056746, zinc complexes, for example in accordance with EP 652273 or WO 2009/062578, diazasilole or tetraazasilole derivatives, for example in accordance with WO 2010/054729, diazaphosphole derivatives, for example in accordance with WO 2010/054730, or indenocarbazole derivatives, for example in accordance with WO 10/136,109 and WO 2011/000455, or bridged carbazoles, for example in accordance with WO 2011/088877 and WO 2011/128017.

Preferred phosphorescent dopants for use in mixed-matrix systems comprising the compounds according to the invention are the phosphorescent dopants shown in a following table.

In a further preferred embodiment of the invention, the compounds of the formula (I), (II) or (III) are employed as hole-transport material. The compounds are then preferably employed in a hole-transport layer and/or in a hole-injection layer. A hole-injection layer in the sense of this invention is a layer which is directly adjacent to the anode. A hole-transport layer in the sense of this invention is a layer which is located between the hole-injection layer and the emission layer. The compounds are used as hole-transport material if, in particular, they are substituted by one or more aromatic ring systems having 12 to 20 aromatic ring atoms and/or by one or more arylamino groups.

If the compound of the formula (I), (II) or (III) is employed as hole-transport material in a hole-transport layer, the compound can be employed as pure material, i.e. in a proportion of 100%, in the hole-transport layer or it can be employed in combination with further compounds, in particular p-dopants, in the hole-transport layer.

In a further embodiment of the invention, the compounds of the formula (I), (II) or (III) are employed as fluorescent dopants in an emitting layer. In particular, the compounds are suitable as fluorescent dopants if they are substituted by one or more aromatic systems, preferably aromatic systems containing 12 to 20 aromatic ring atoms. The compounds according to the invention are preferably used as green or blue emitters.

The proportion of the compound of the formula (I), (II) or (III) as dopant in the mixture of the emitting layer is in this case between 0.1 and 50.0% by vol., preferably between 0.5 and 20.0% by vol., particularly preferably between 0.5 and 8.0% by vol. Correspondingly, the proportion of the matrix material is between 50.0 and 99.9% by vol., preferably between 80.0 and 99.5% by vol., particularly preferably between 92.0 and 99.5% by vol.

Preferred matrix materials for use in combination with the compounds according to the invention as fluorescent dopants are mentioned in one of the following sections. They correspond to the matrix materials for fluorescent dopants that are indicated as preferred.

In a further embodiment of the invention, the compounds are employed as electron-transport materials in an electron-transport layer of an organic electroluminescent device. In this case, it is preferred for the compounds according to the invention to have one or more electron-deficient groups, such as, for example, six-membered heteroaryl ring groups containing one or more, nitrogen atoms or five-membered heteroaryl ring groups containing two or more heteroatoms.

The organic electroluminescent device may also comprise a plurality of emitting layers. These emission layers in this case particularly preferably have in total a plurality of emission maxima between 380 nm and 750 nm, resulting overall in white emission, i.e. various emitting compounds which are able to fluoresce or phosphoresce and which emit blue or yellow or orange or red light are used in the emitting layers, where the various colours in this embodiment of the invention together give white light. Particular preference is given to three-layer systems, i.e. systems having three emitting layers, where one pr more of these layers comprises a compound of the formula (I), (II) or (III) and where the three layers exhibit blue, green and orange or red emission (for the basic structure see, for example, WO 2005/011013). Likewise, emitters which have broad-band emission bands and thus exhibit white emission are suitable for white emission in such systems. Alternatively and/or additionally, the compounds according to the invention may also be present in a hole-transport layer or electron-transport layer or in another layer in such systems.

The further functional materials preferably employed in the electronic devices comprising one or more compounds according to the invention are shown below.

Particularly suitable phosphorescent dopants are the compounds shown in the following table.

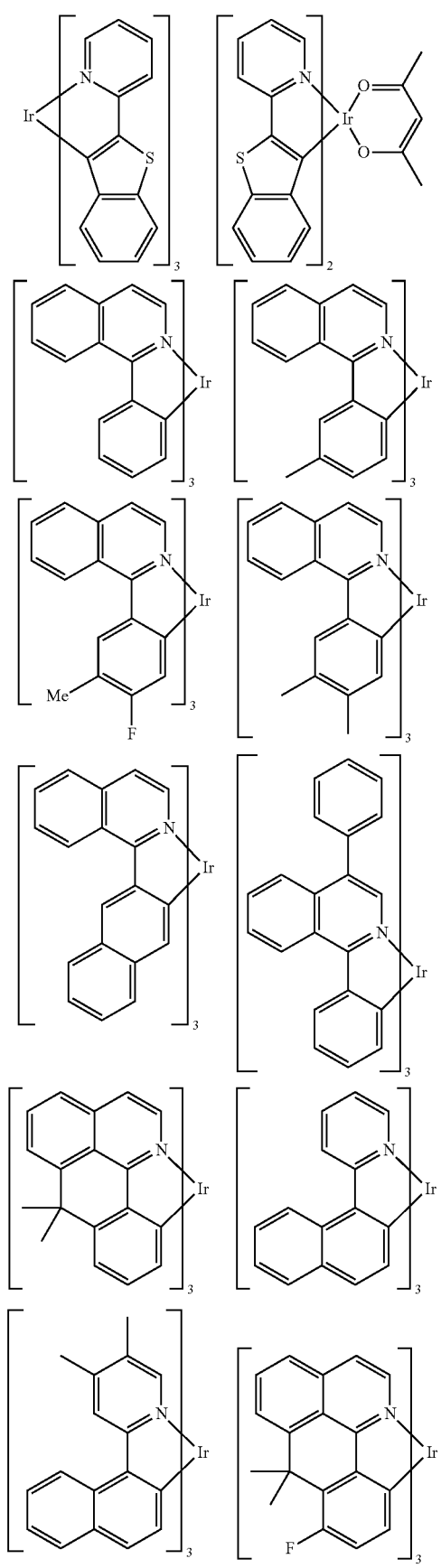
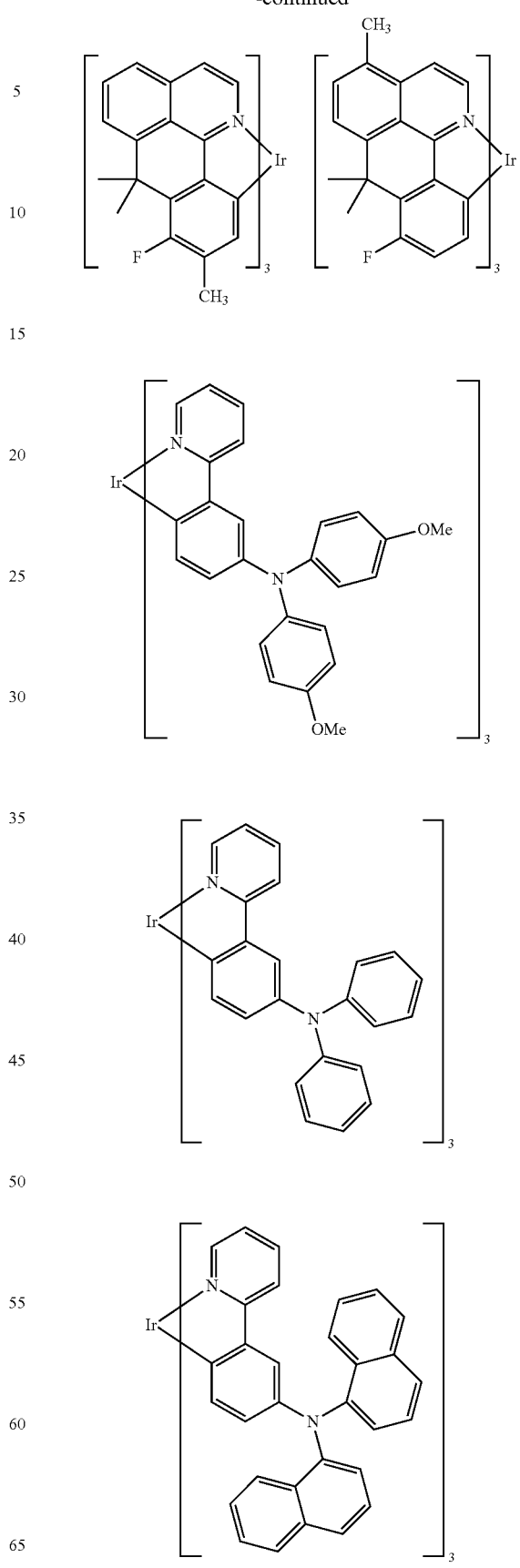

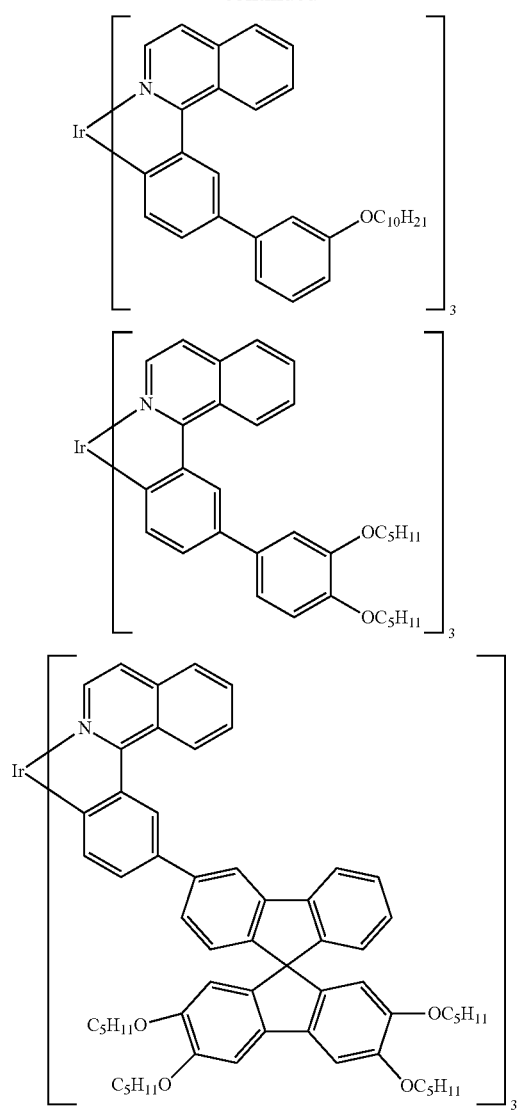
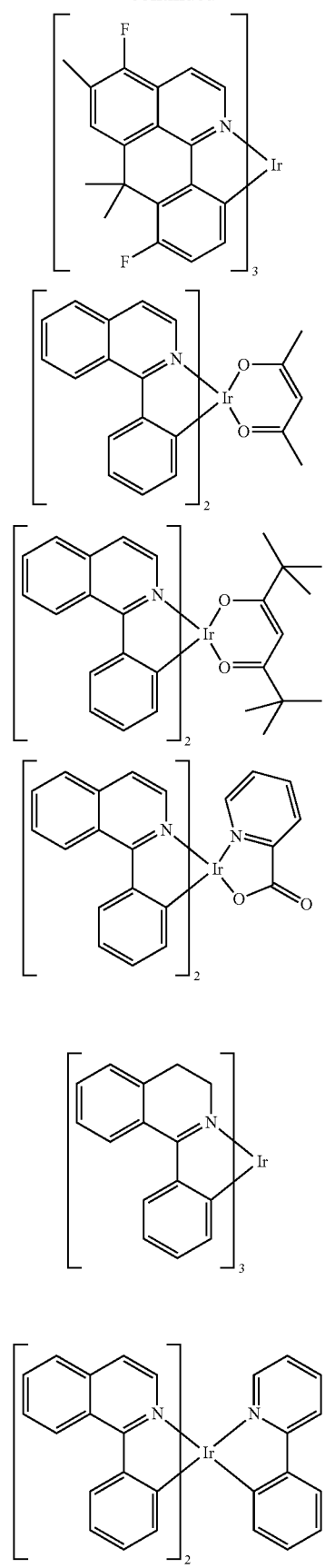

-continued
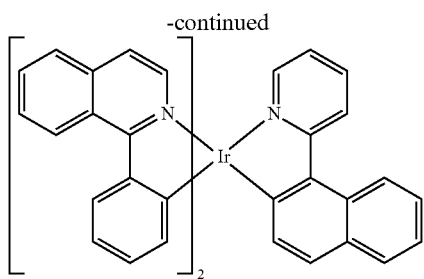
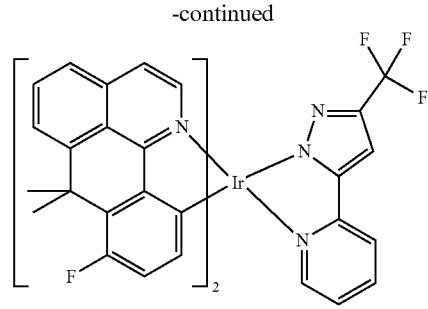
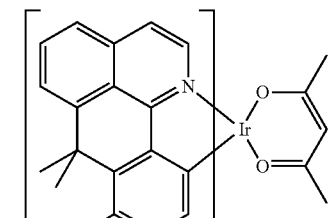
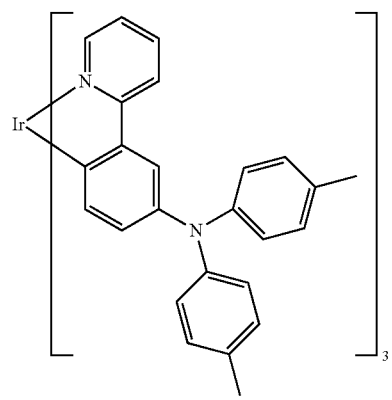
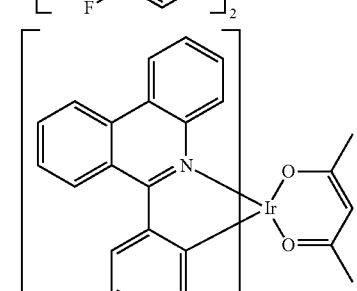
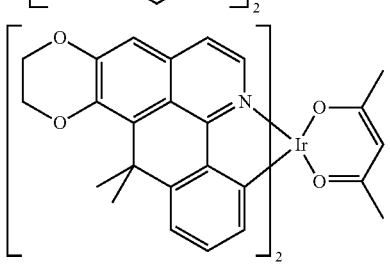
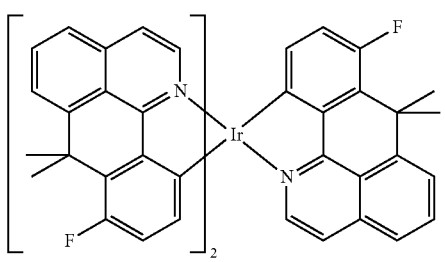
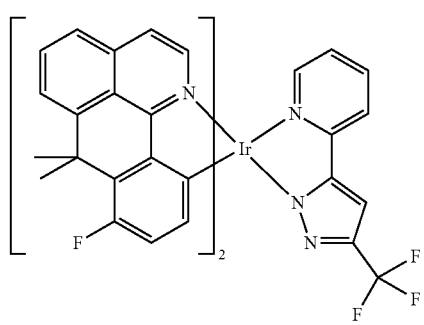
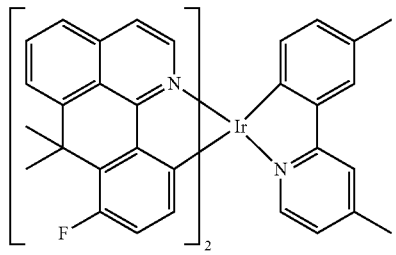
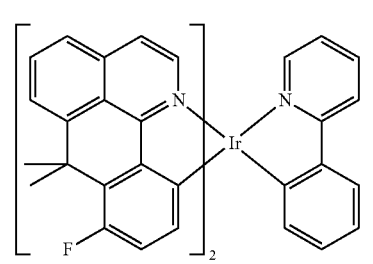
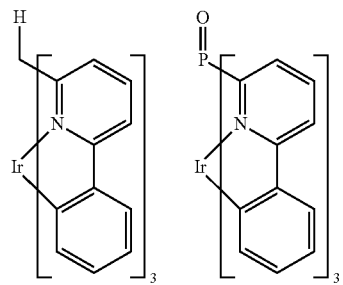

73
-continued
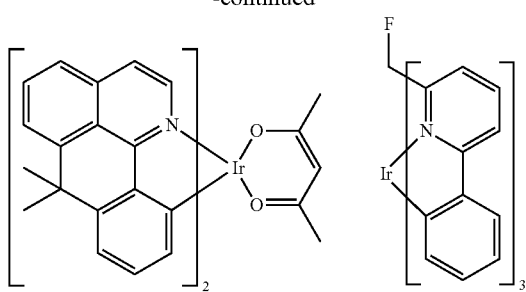
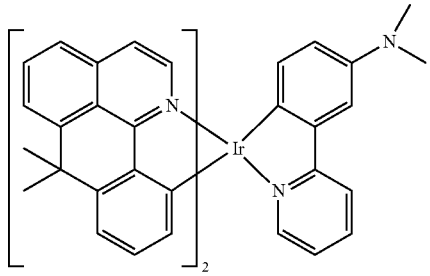
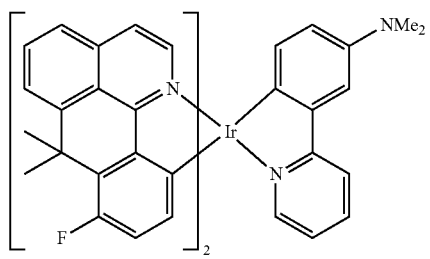
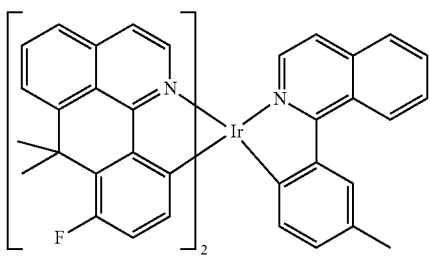
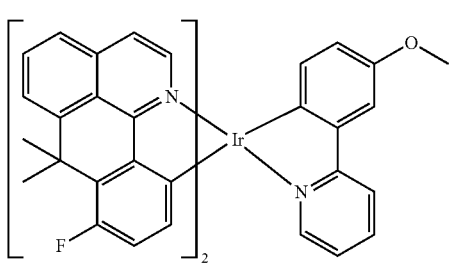
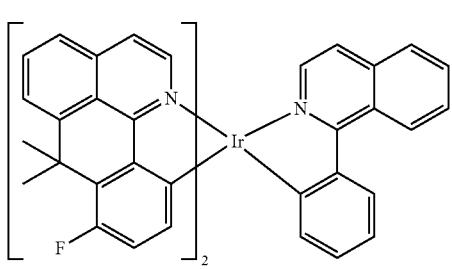
74
-continued
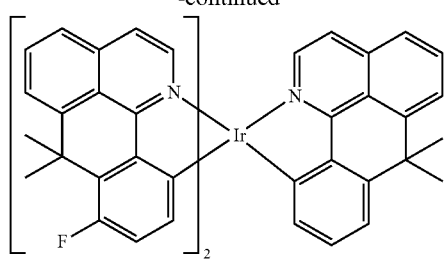
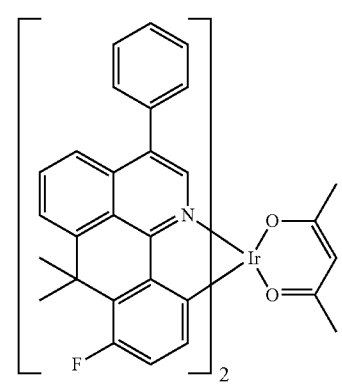
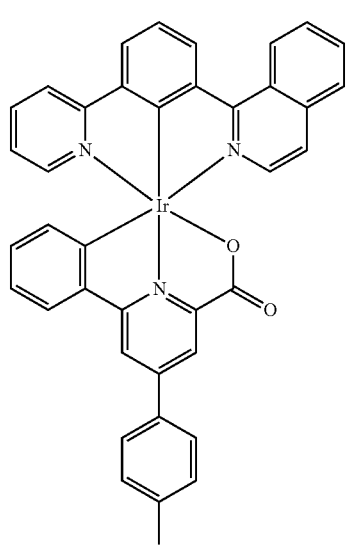
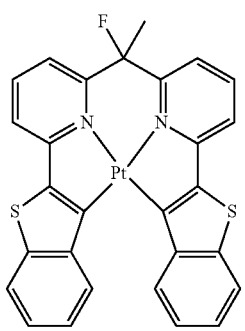

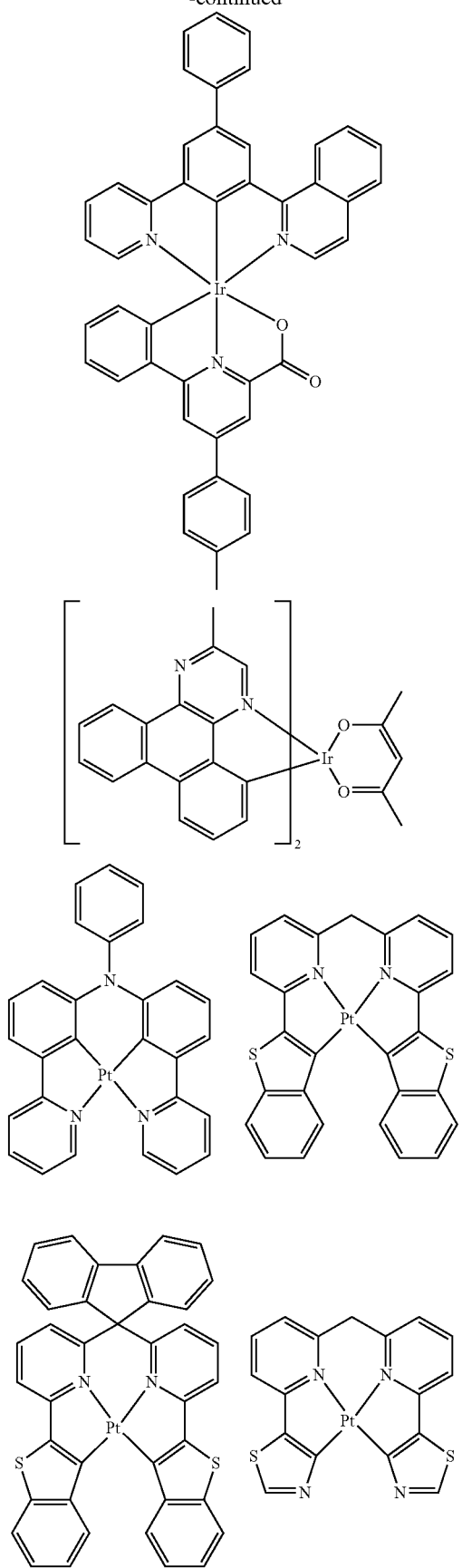
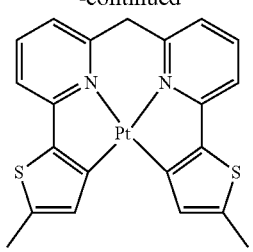
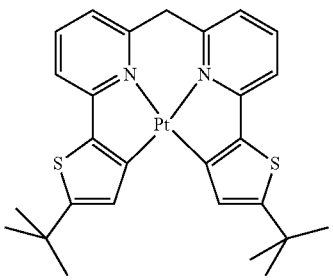
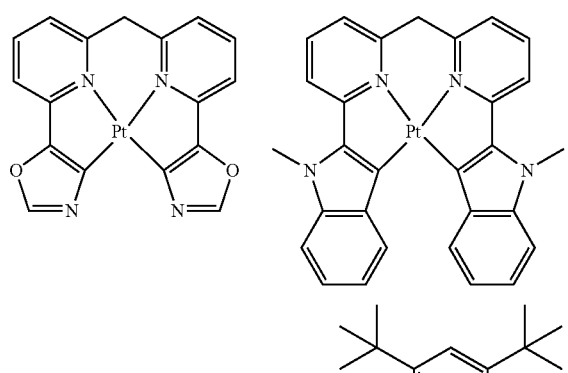
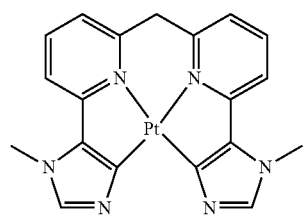
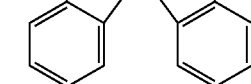
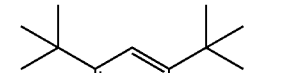
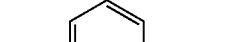

77
-continued
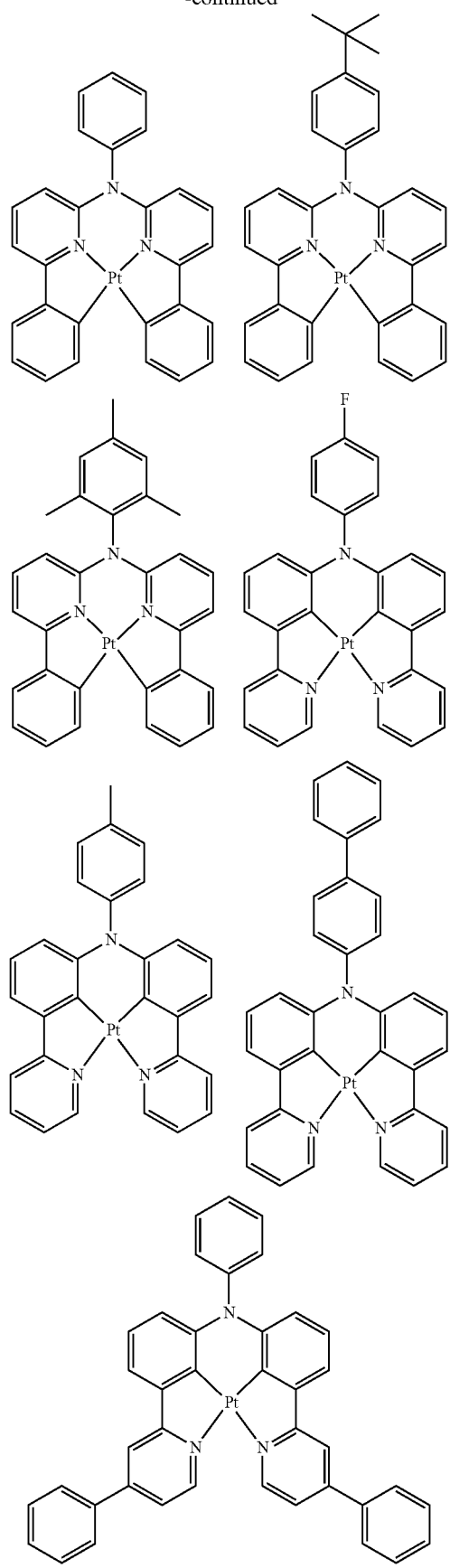
78
-continued
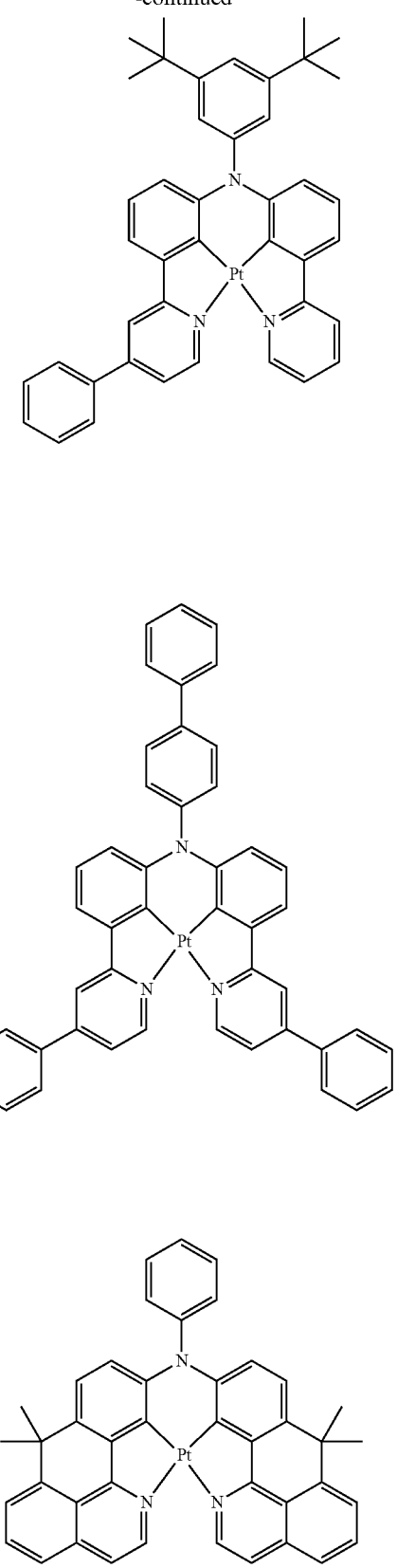

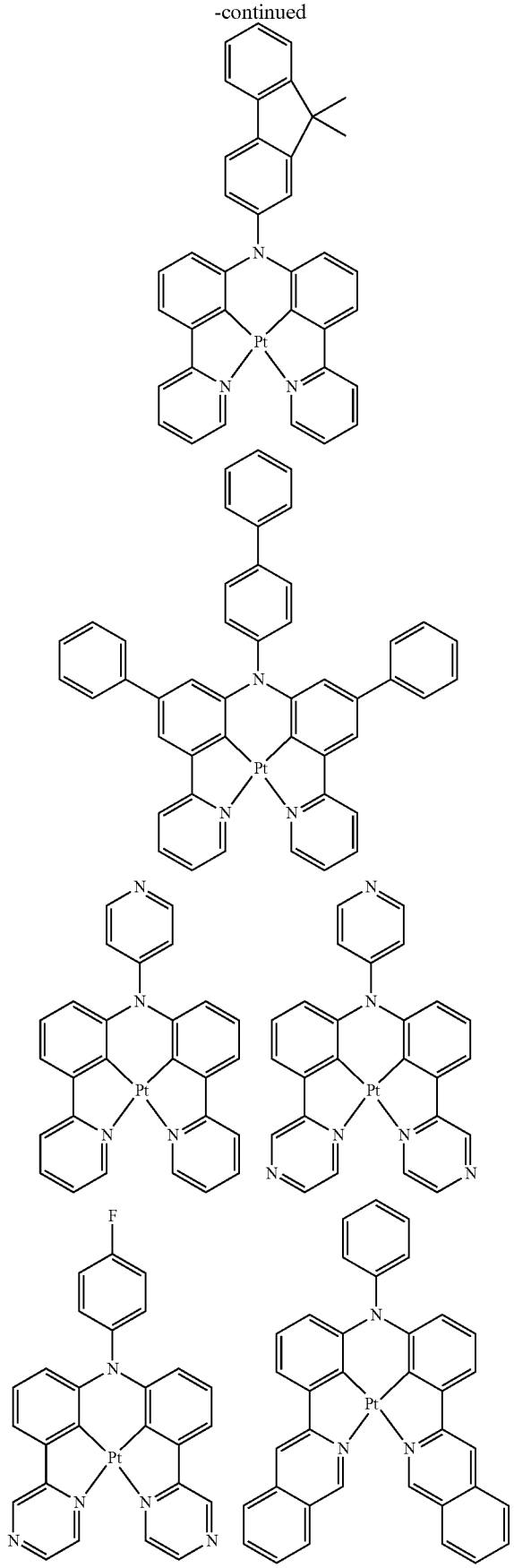
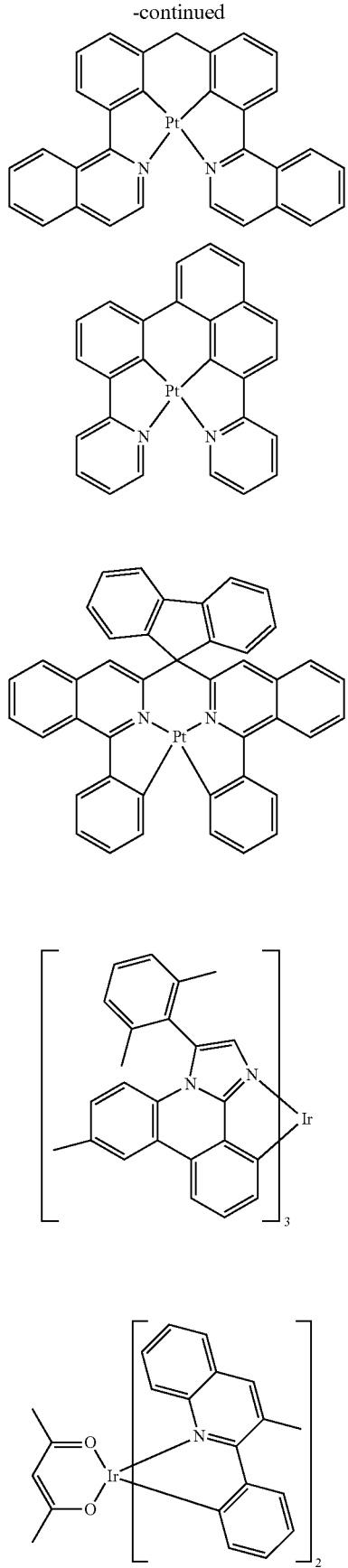

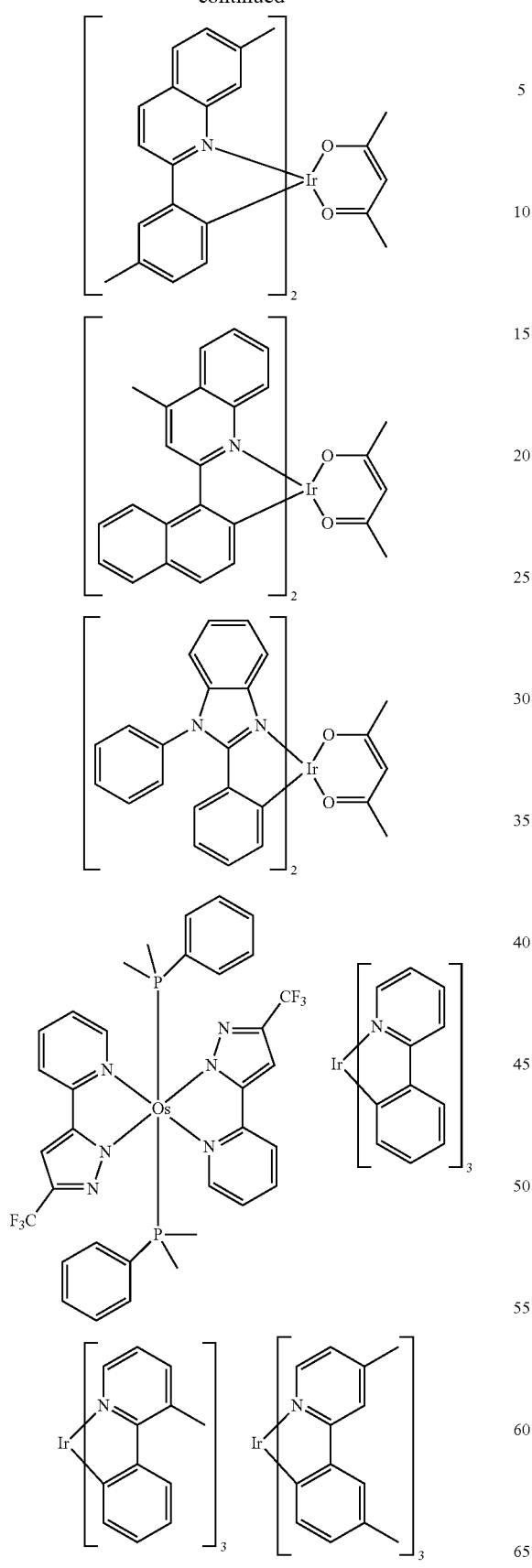
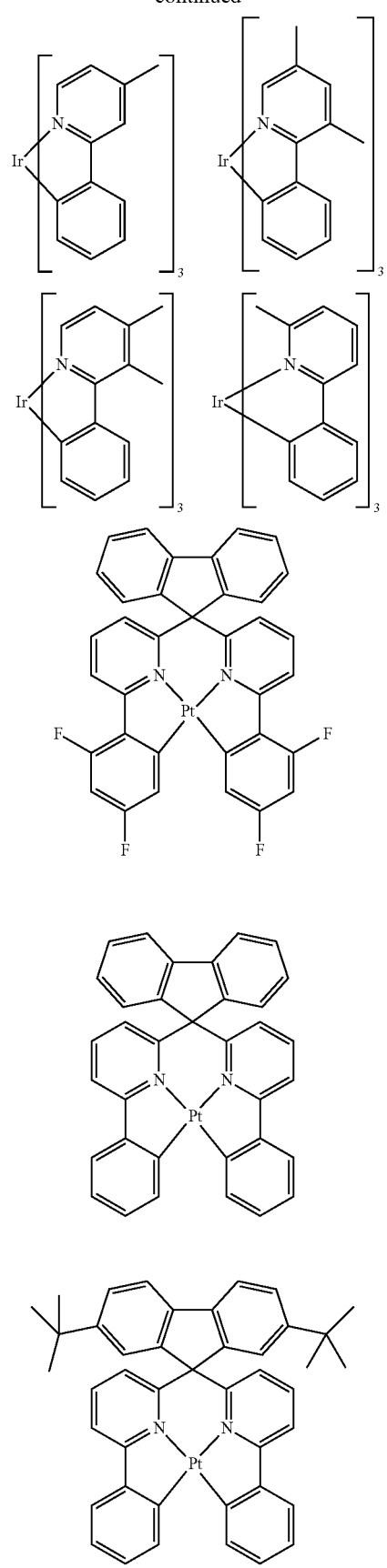

83
-continued
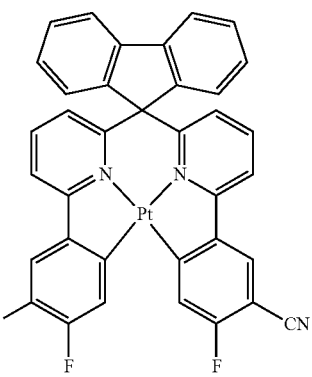
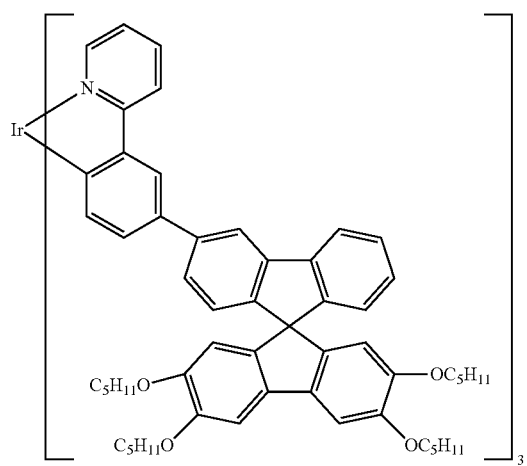
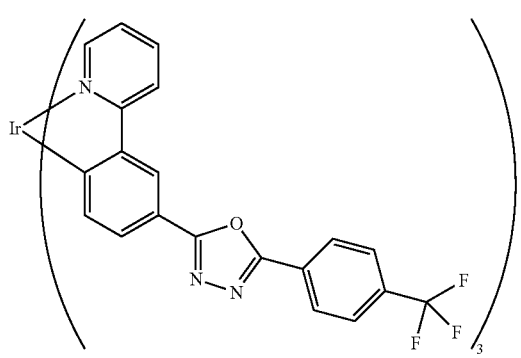
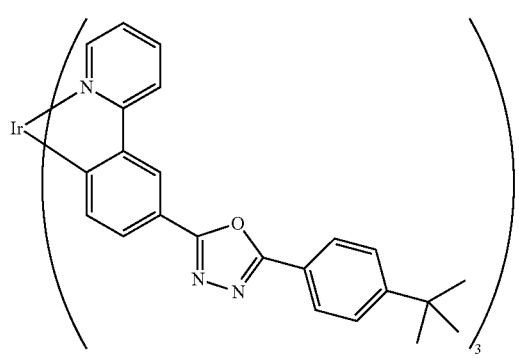
84
-continued
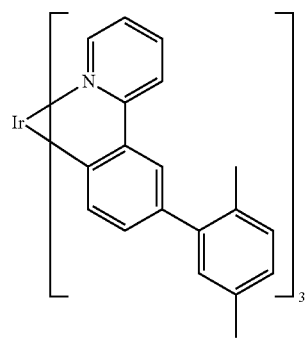
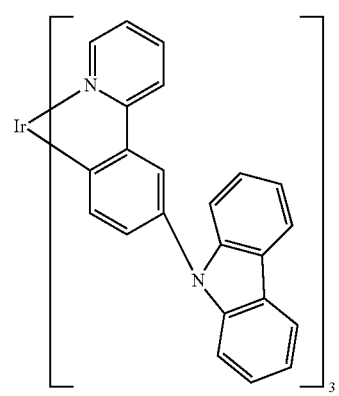
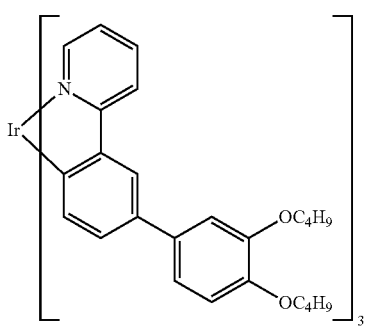
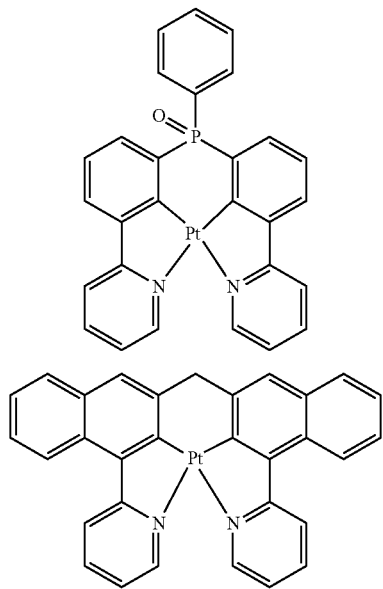

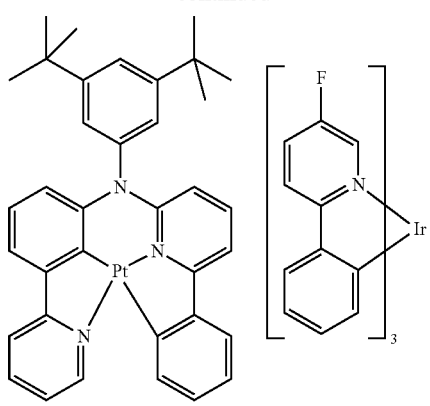
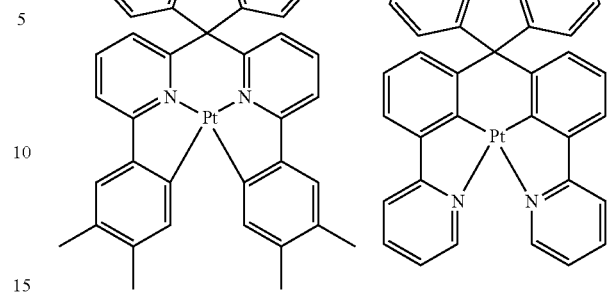
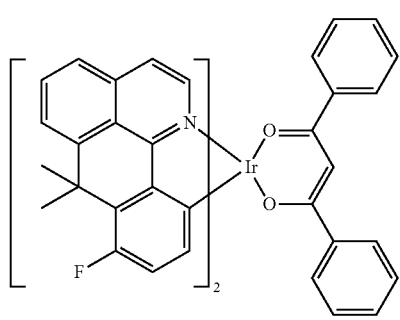
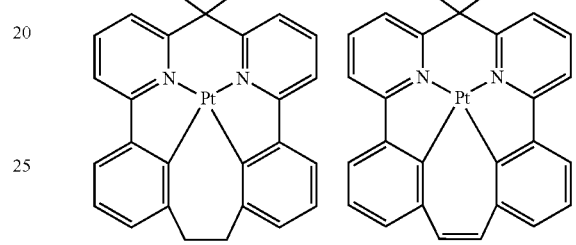
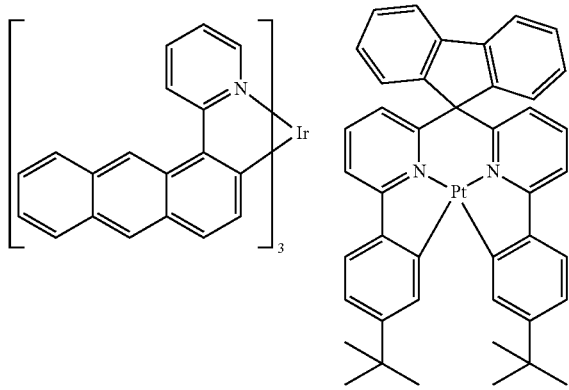
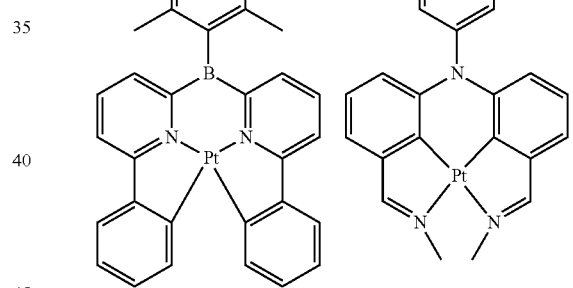
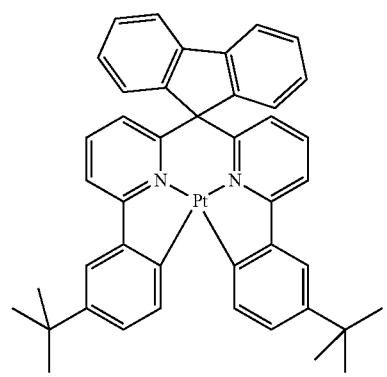
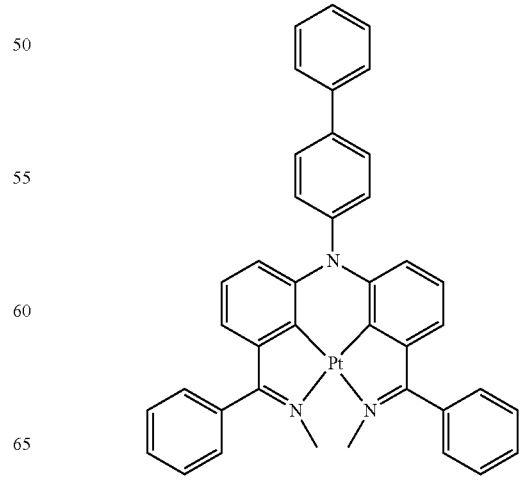

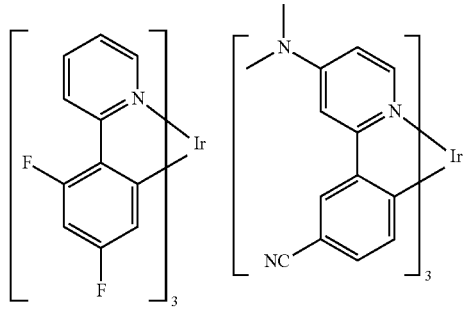
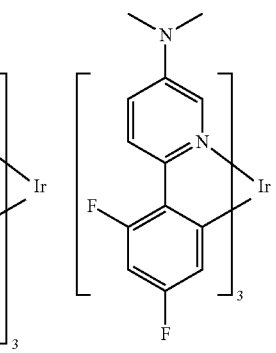
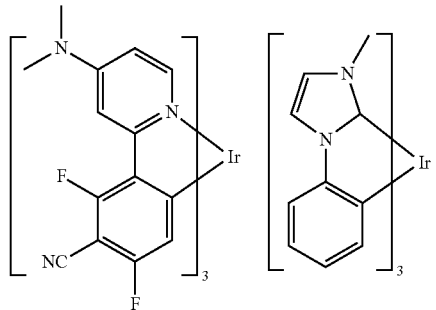
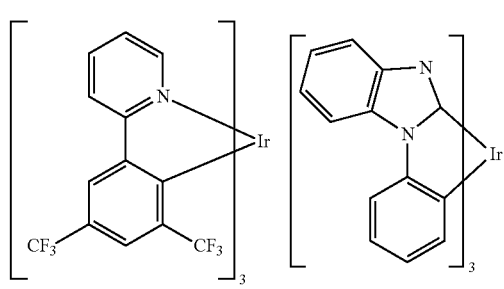
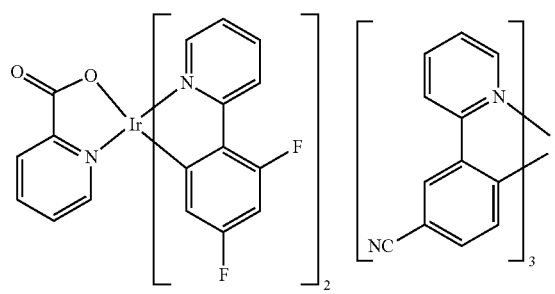
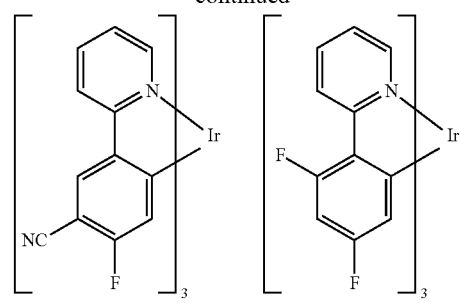
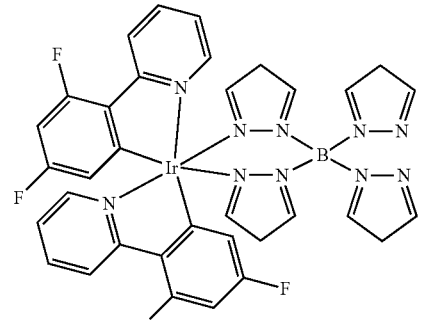
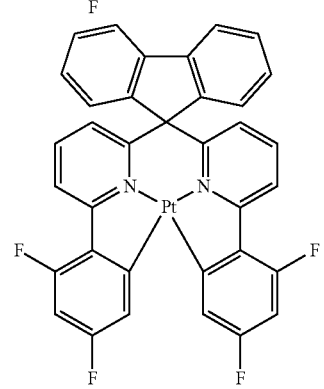
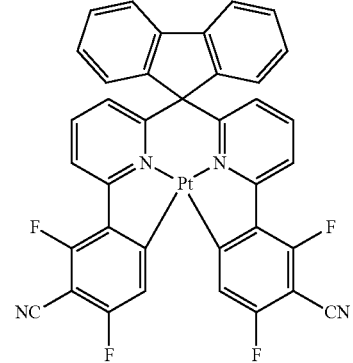
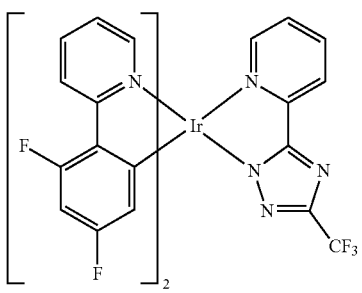

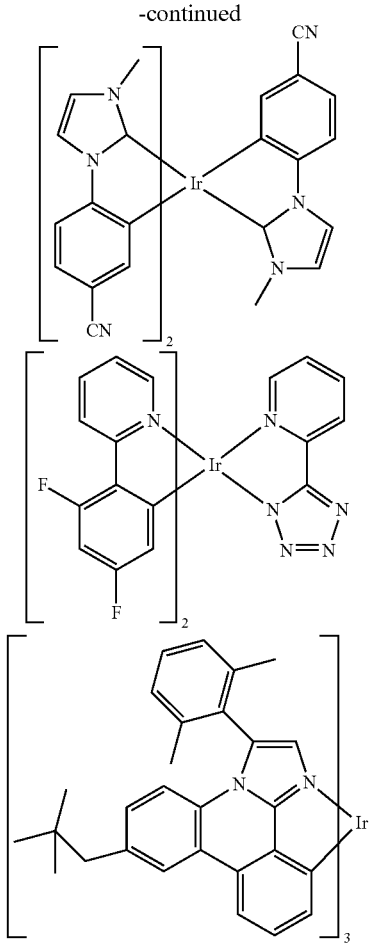

Preferred fluorescent dopants are selected from the class of the monostyrylamines, the distyrylamines, the tristyrylamines, the tetrastyrylamines, the styrylphosphines, the styryl ethers and the arylamines. A monostyrylamine is taken to mean a compound which contains one substituted or unsubstituted styryl group and at least one, preferably aromatic, amine. A distyrylamine is taken to mean a compound which contains two substituted or unsubstituted styryl groups and at least one, preferably aromatic, amine. A tristyrylamine is taken to mean a compound which contains three substituted or unsubstituted styryl groups and at least one, preferably aromatic, amine. A tetrastyrylamine is taken to mean a compound which contains four substituted or unsubstituted styryl groups and at least one, preferably aromatic, amine. The styryl groups are particularly preferably stilbenes, which may also be further substituted. Corresponding styrylphosphines and styryl ethers are defined analogously to the amines. An arylamine or aromatic amine in the sense of this invention is taken to mean a compound which contains three substituted or unsubstituted aromatic or heteroaromatic ring systems bonded directly to the nitrogen. At least one of these aromatic or heteroaromatic ring systems is preferably a condensed ring system, particularly preferably having at least 14 aromatic ring atoms. Preferred examples thereof are aromatic anthracenamines, aromatic anthracenediamines, aromatic pyrenamines, aromatic pyrenediamines, aromatic chrysenamines or aromatic chrysenediamines. An aromatic anthracenamine is taken to mean a compound in which one diarylamino group is bonded directly to an anthracene group, preferably in the 9-position. An aromatic anthracenediamine is taken to mean a compound in which two diarylamino groups are bonded directly to an anthracene group, preferably in the 9,10-position. Aromatic pyrenamines, pyrenediamines, chrysenamines and chrysenediamines are defined analogously thereto, where the diarylamino groups are preferably bonded to the pyrene in the 1-position or in the 1,6-position. Further preferred fluorescent dopants are selected from indenofluorenamines or indenofluorenediamines, for example in accordance with WO 2006/122630, benzoindenofluorenamines or benzoindenofluorenediamines, for example in accordance with WO 2008/006449, and dibenzoindenofluorenamines or dibenzoindenofluorenediamines, for example in accordance with WO 2007/140847. Examples of fluorescent dopants from the class of the styrylamines are substituted or unsubstituted tristilbenamines or the fluorescent dopants described in WO 2006/000388, WO 2006/058737, WO 2006/000389, WO 2007/065549 and WO 2007/115610. Preference is furthermore given to the condensed hydrocarbons disclosed in DE 102008035413. Furthermore, the compounds of the formula (I), (II) or (III) can be used as fluorescent dopants.

Suitable fluorescent dopants are furthermore the structures depicted in the following table, and the derivatives of these structures disclosed in JP 2006/001973, WO 2004/047499, WO 2006/098080, WO 2007/065678, US 2005/0260442 and WO 2004/092111.

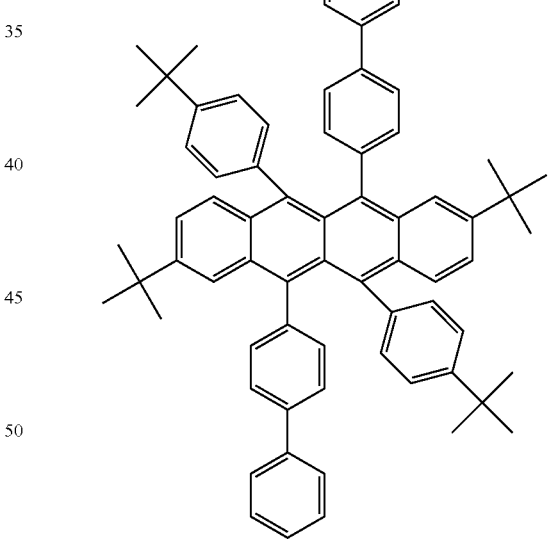

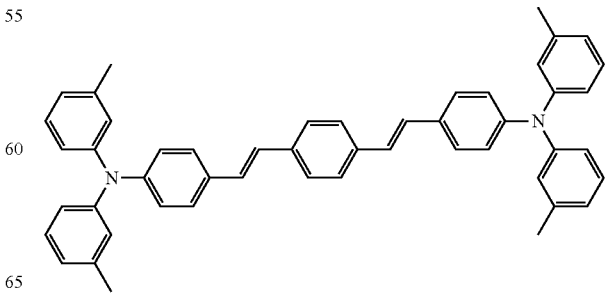

91
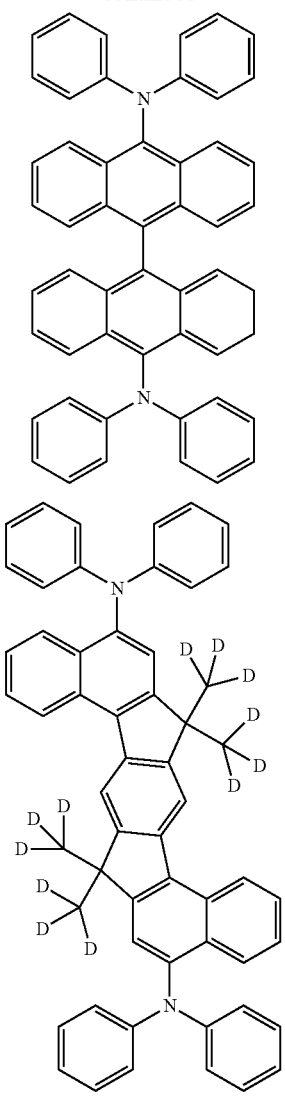
92
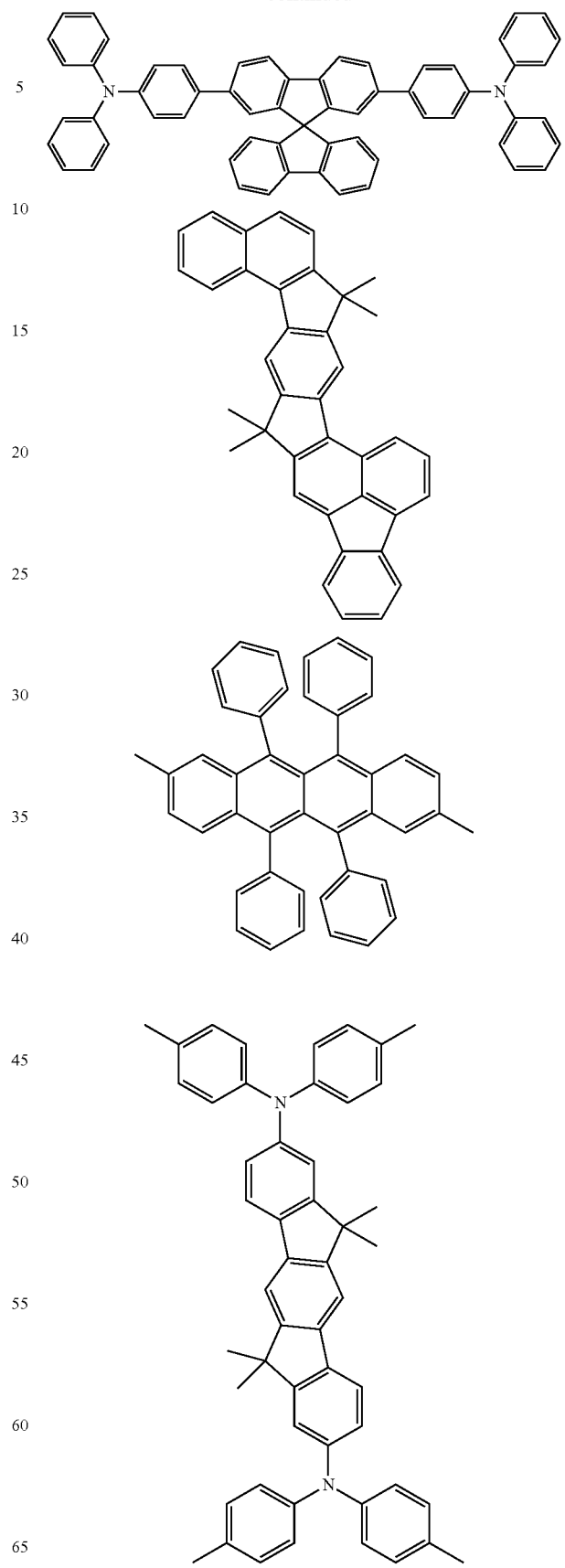

93
-continued
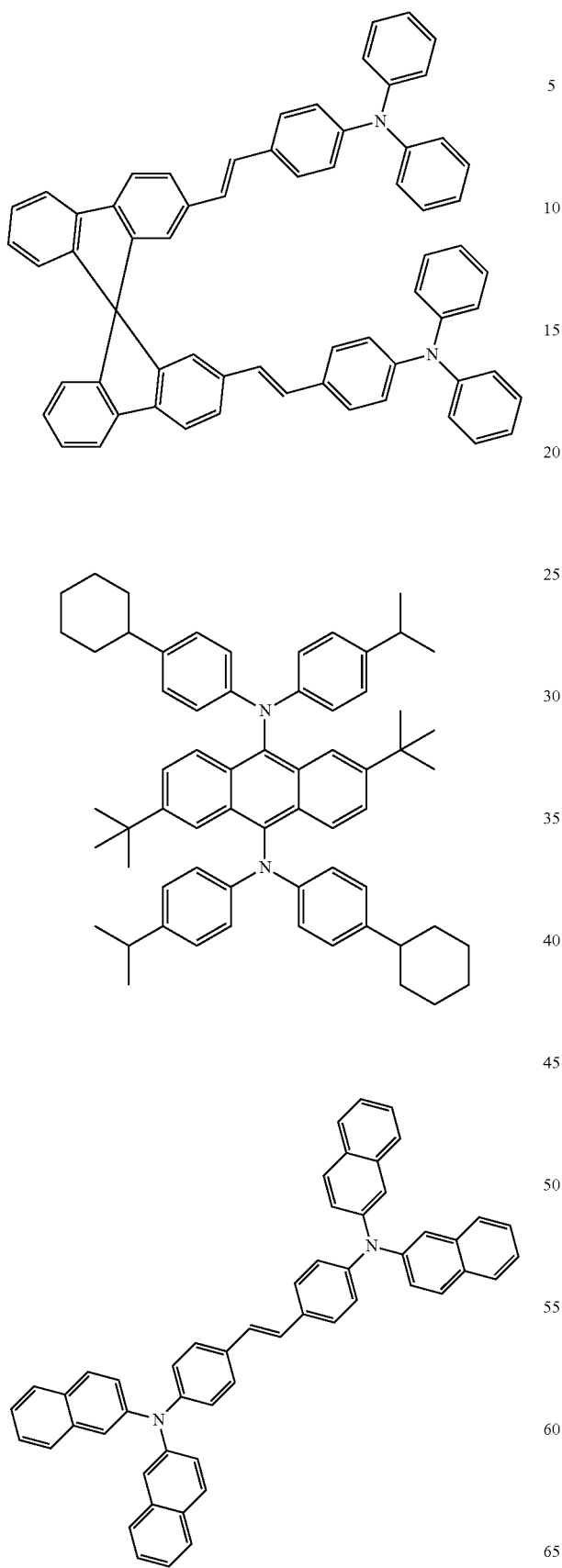
94
-continued
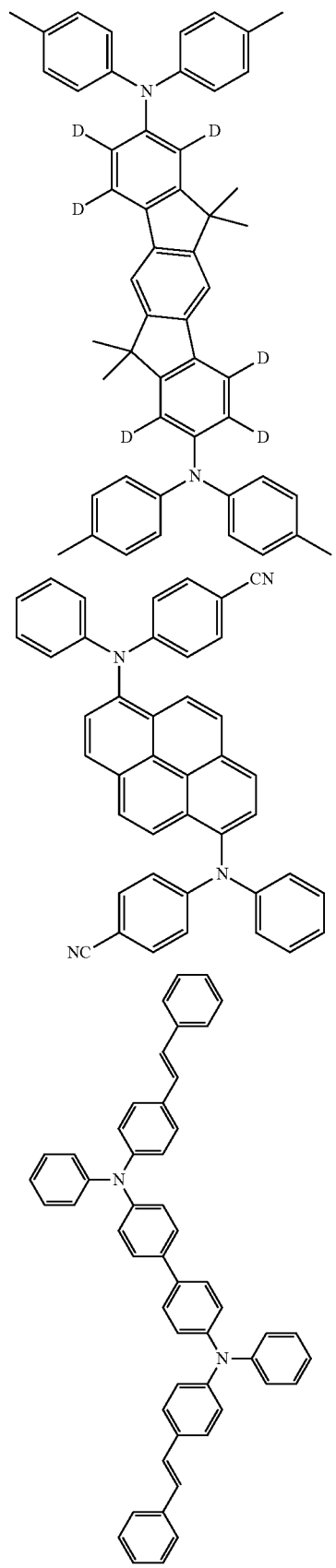

95
-continued
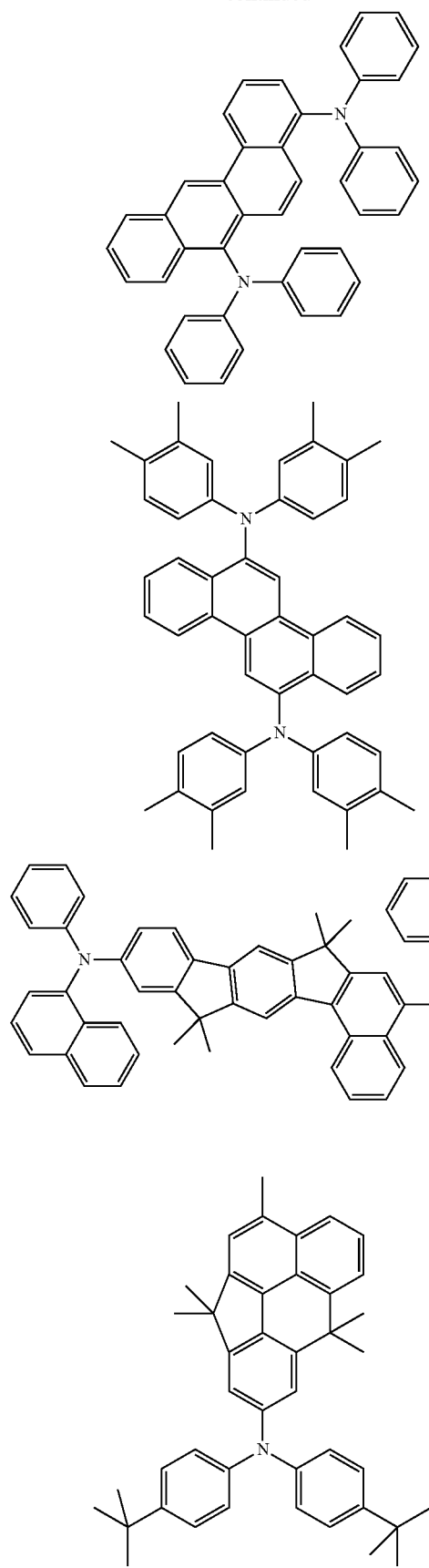
96
-continued
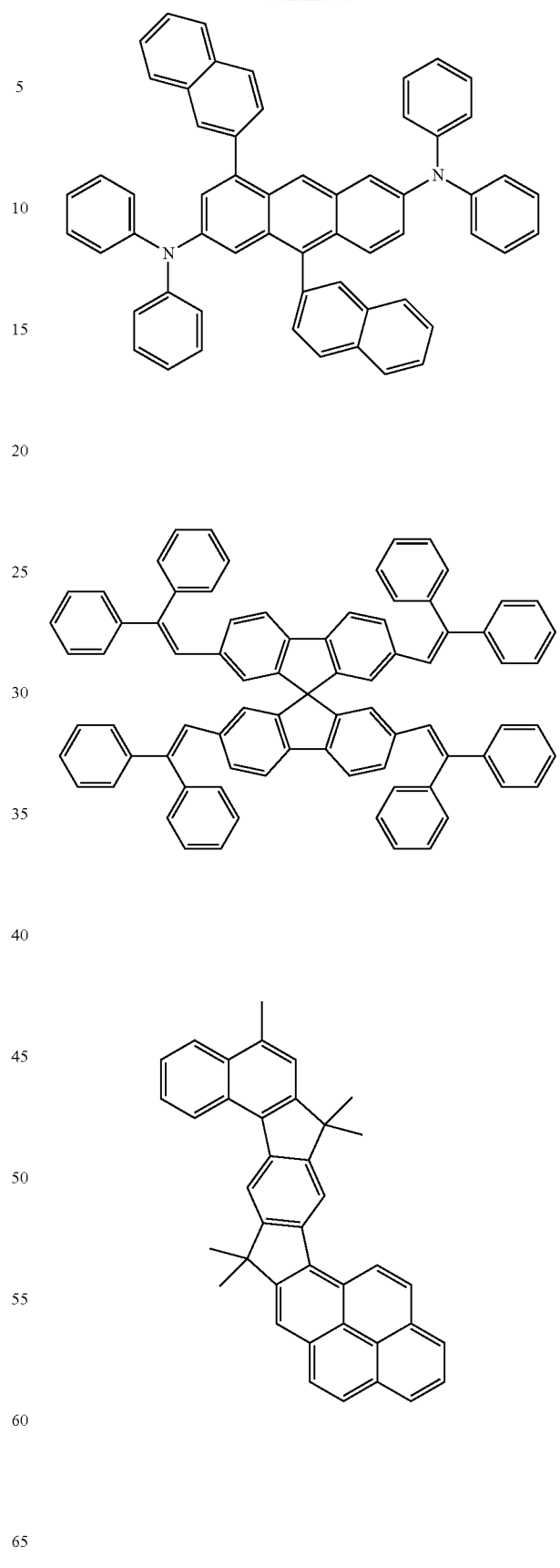

97
-continued
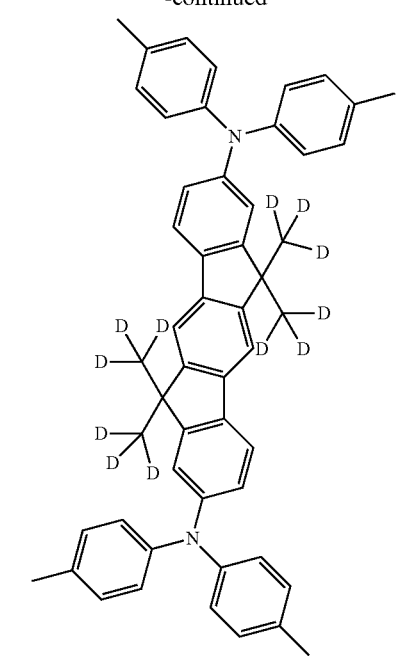
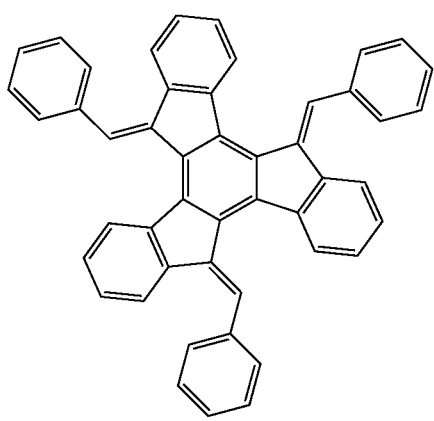
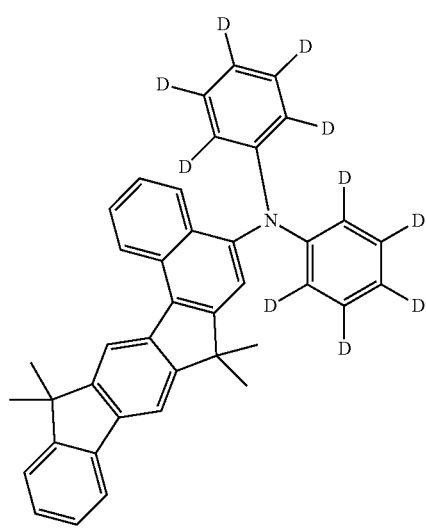
98
-continued
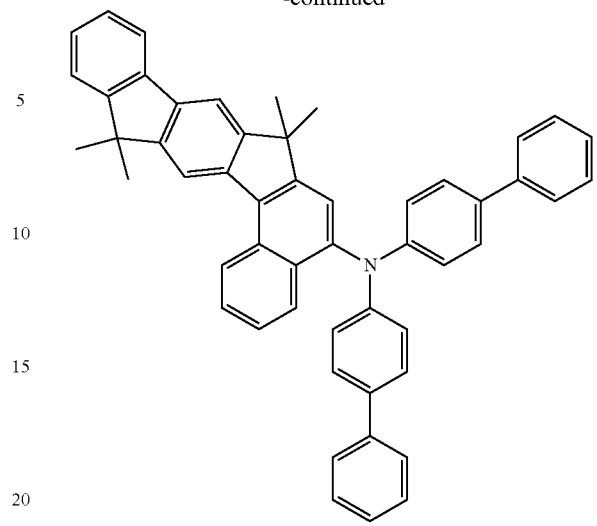
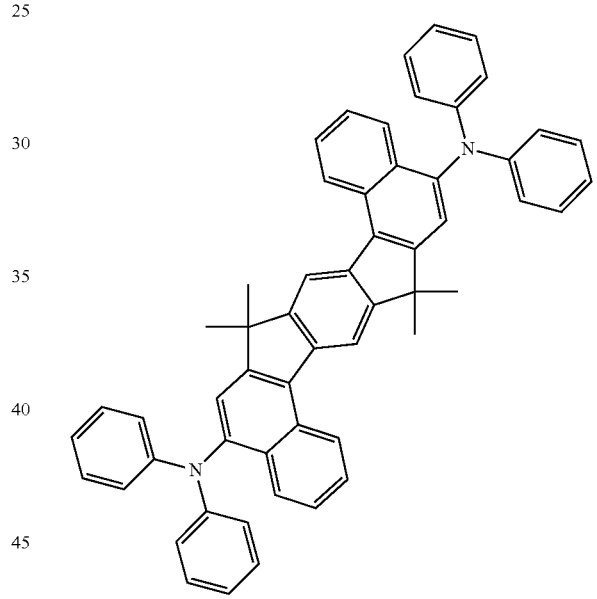

99
-continued
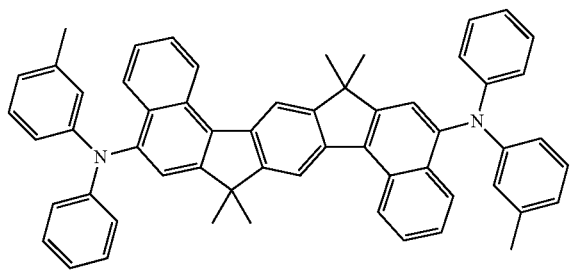
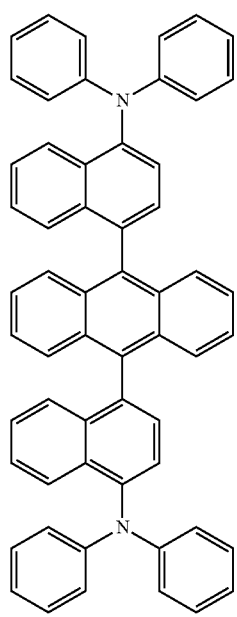
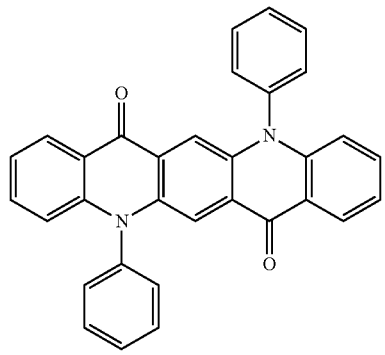
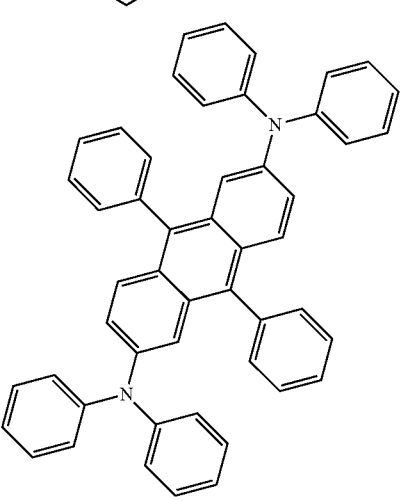
100
-continued
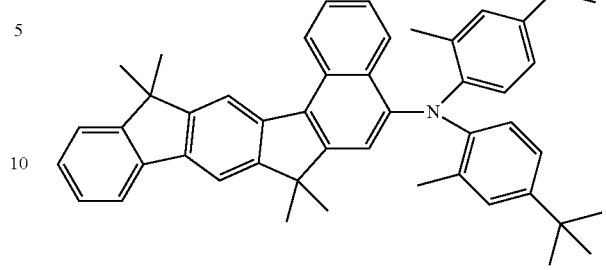
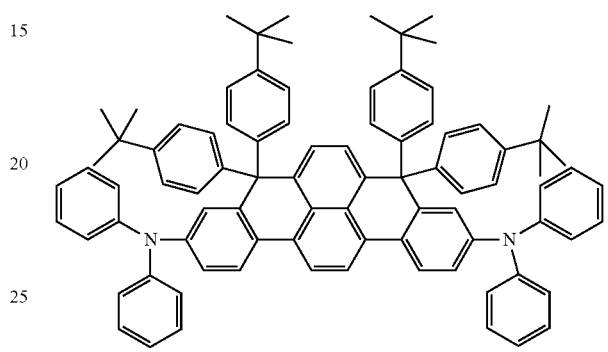
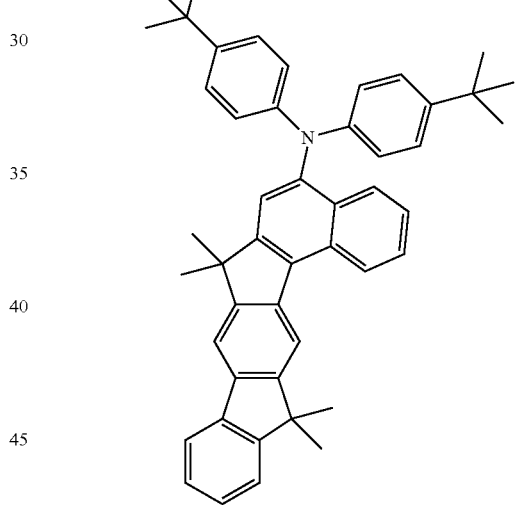
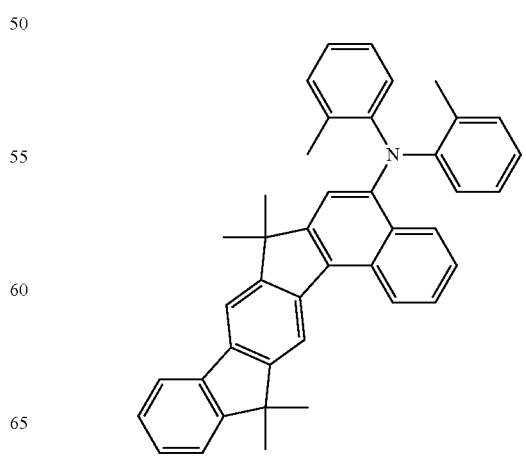

101
-continued
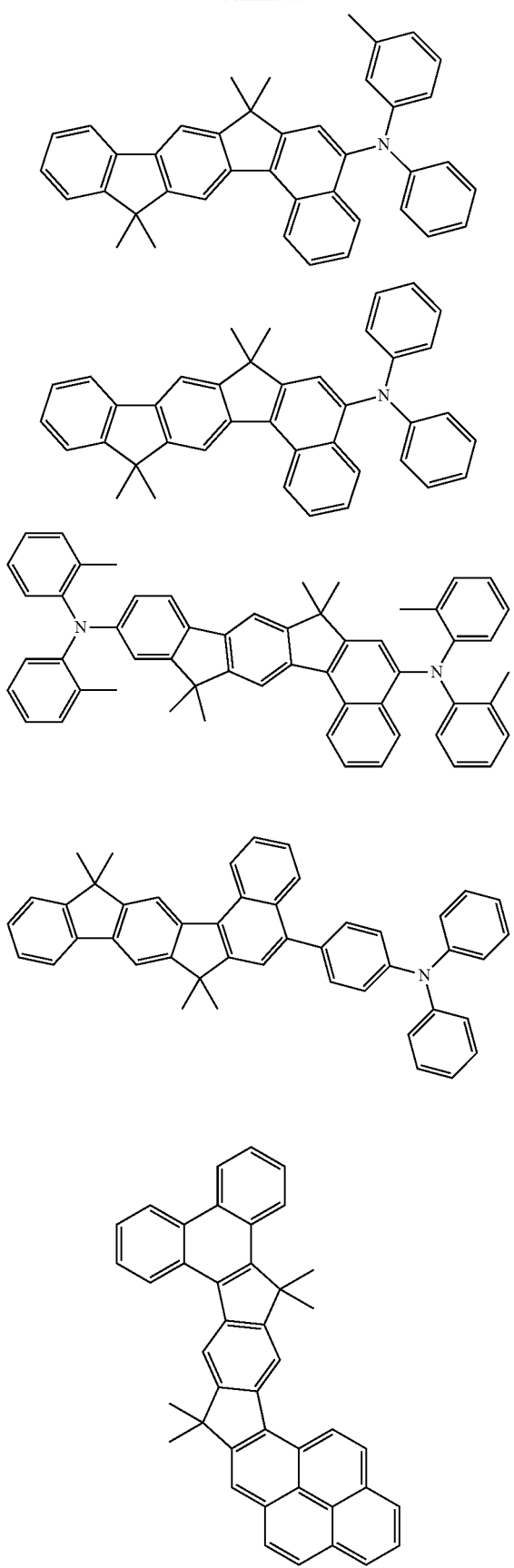
102
-continued
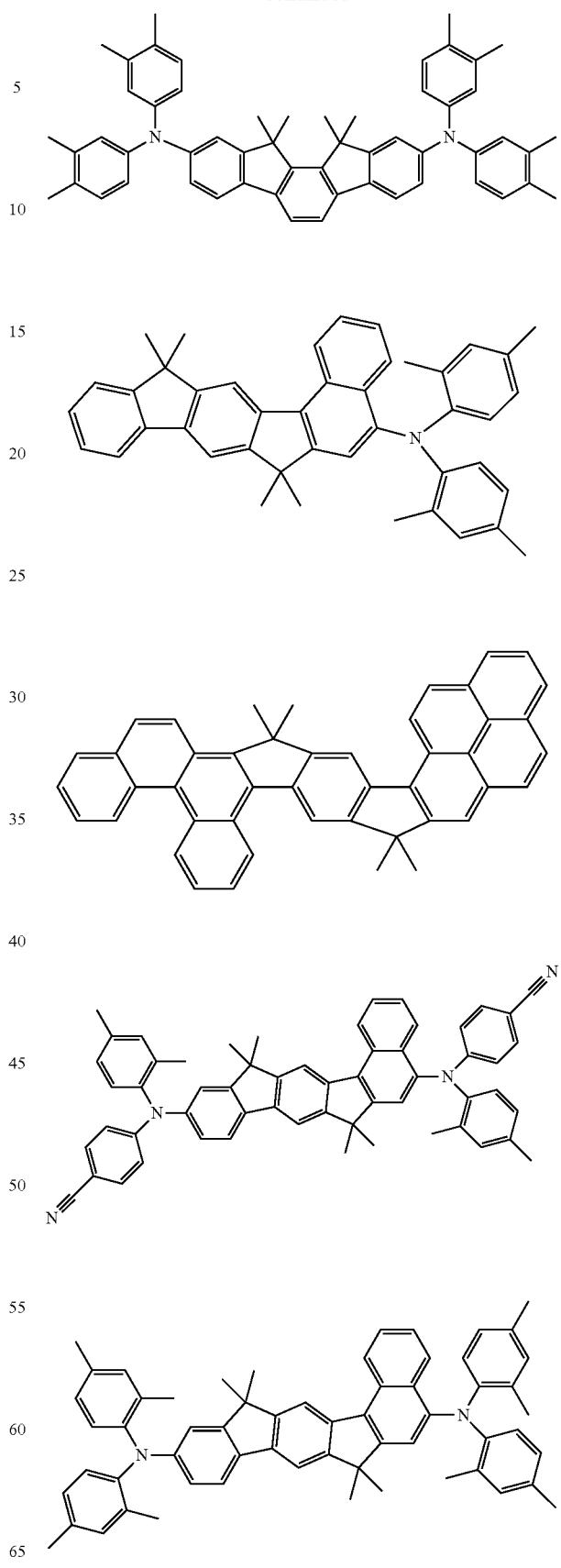

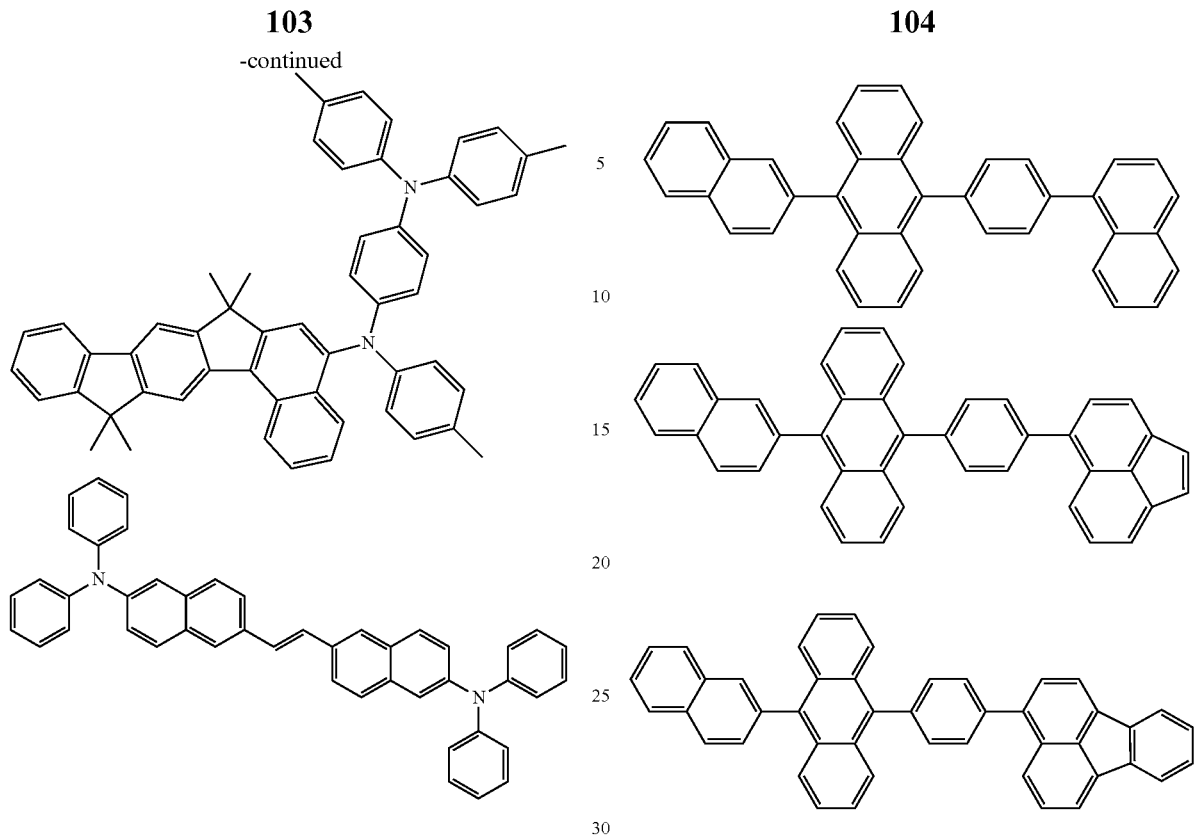

Suitable matrix materials, preferably for fluorescent dopants, are materials from various classes of substance. Preferred matrix materials are selected from the classes of the oligoarylenes (for example 2,2',7,7-tetraphenylspirobifluorene in accordance with EP 676461 or dinaphthylanthracene), in particular the oligoarylenes containing condensed aromatic groups, the oligoarylenevinylenes (for example DPVBi or spiro-DPVBi in accordance with EP 676461), the polypodal metal complexes (for example in accordance with WO 2004/081017), the hole-conducting compounds (for example in accordance with WO 2004/058911), the electron-conducting compounds, in particular ketones, phosphine oxides, sulfoxides, etc. (for example in accordance with WO 2005/084081 and WO 2005/084082), the atropisomers (for example in accordance with WO 2006/048268), the boronic acid derivatives (for example in accordance with WO 2006/117052) or the benzanthracenes (for example in accordance with WO 2008/145239). Suitable matrix materials are furthermore preferably the compounds according to the invention. Particularly preferred matrix materials are selected from the classes of the oligoarylenes, comprising naphthalene, anthracene, benzanthracene and/or pyrene or atropisomers of these compounds, the oligoarylenevinylenes, the ketones, the phosphine oxides and the sulfoxides. Very particularly preferred matrix materials are selected from the classes of the oligoarylenes, comprising anthracene, benzanthracene, benzophenanthrene and/or pyrene or atropisomers of these compounds. An oligoarylene in the sense of this invention is intended to be taken to mean a compound in which at least three aryl or arylene groups are bonded to one another.

Suitable matrix materials, preferably for fluorescent dopants, are, for example, the materials depicted in the following table, and derivatives of these materials, as disclosed in WO 2004/018587, WO 2008/006449, U.S. Pat. No. 5,935,721, US 2005/0181232, JP 2000/273056, EP 681019, US 2004/0247937 and US 2005/0211958.

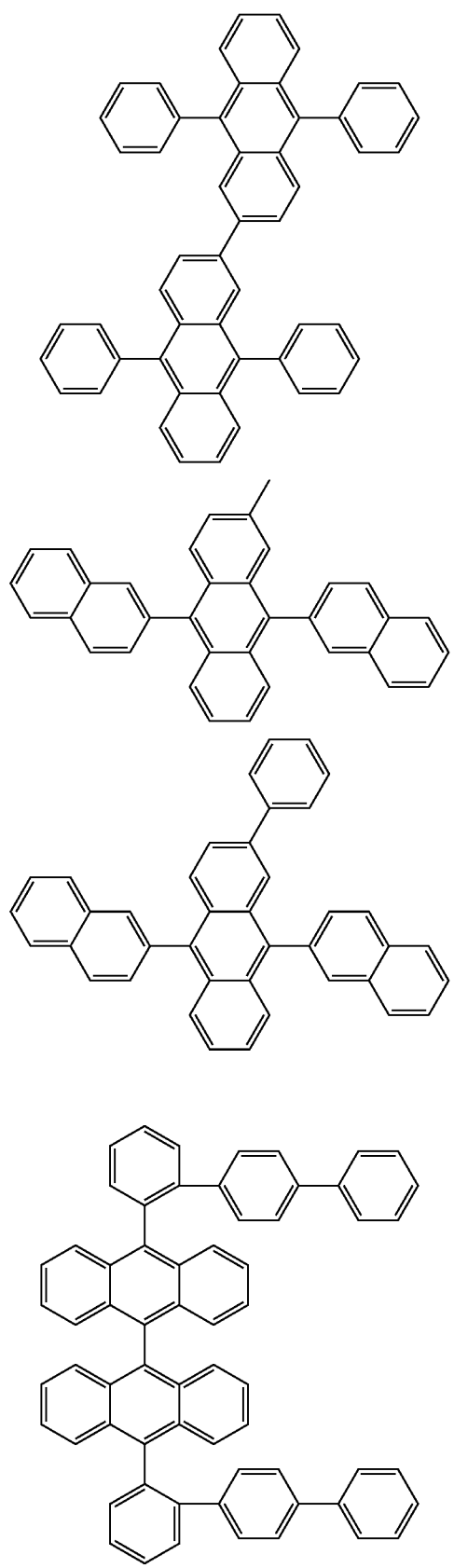
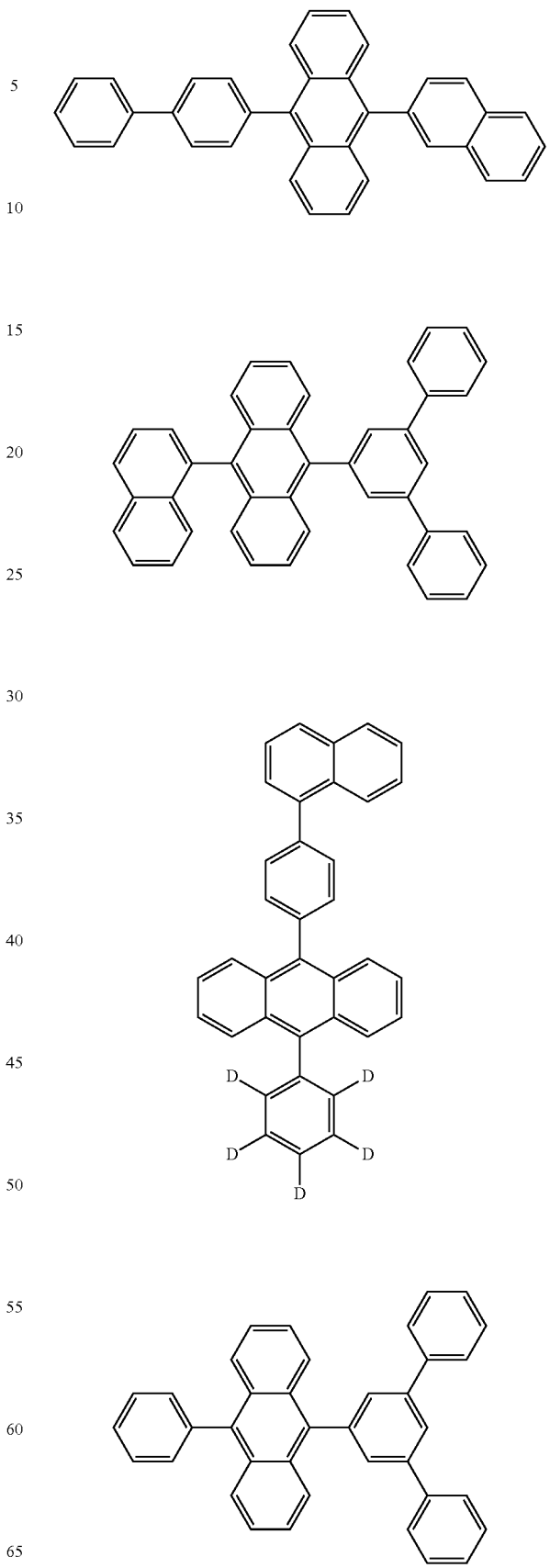

107
-continued
108
-continued
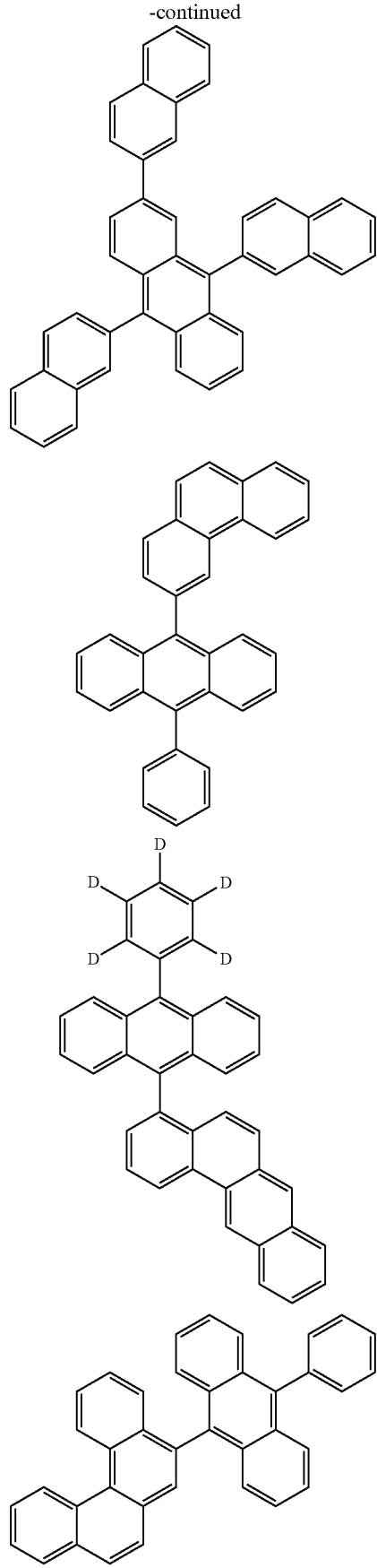
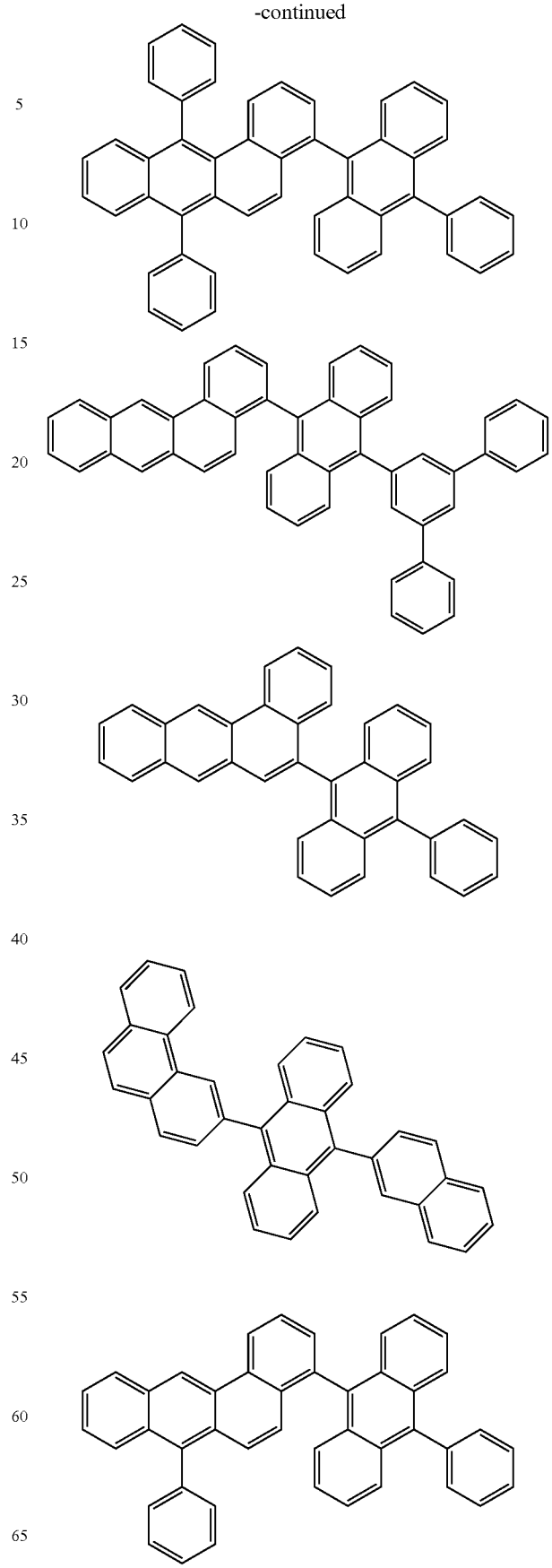

109
-continued
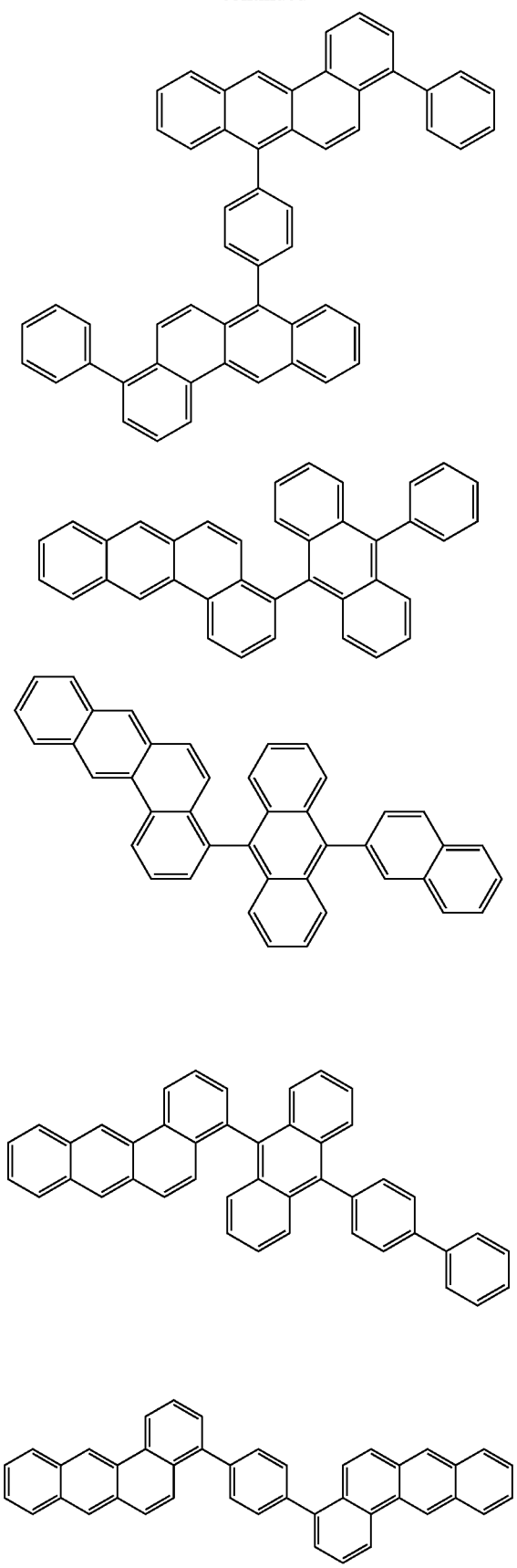
110
-continued
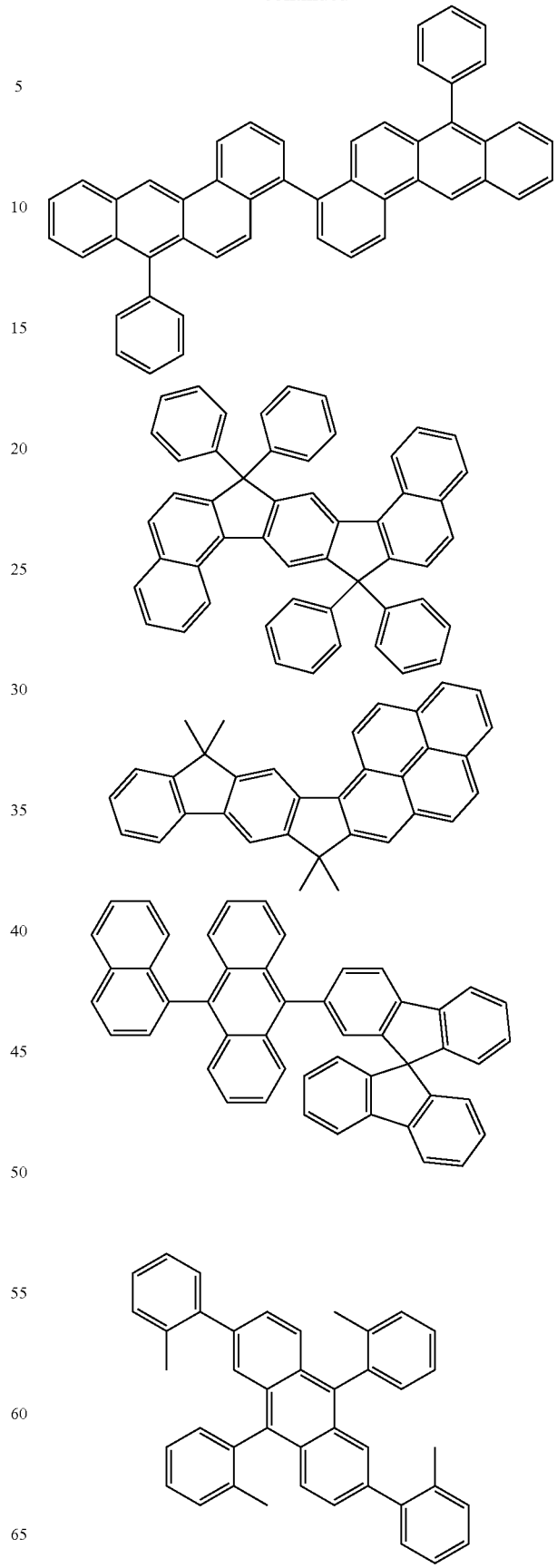

-continued

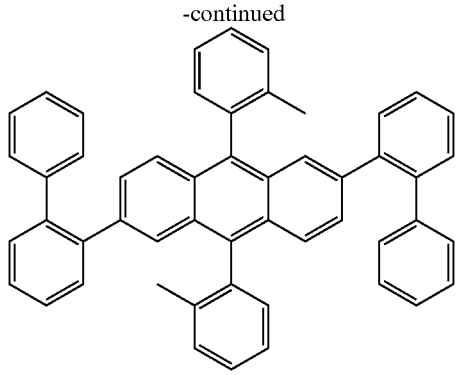

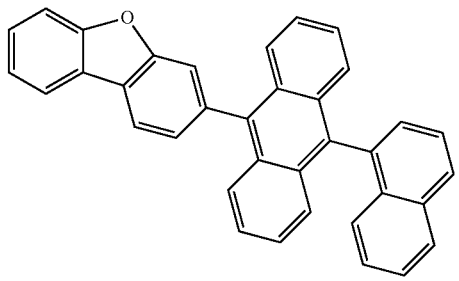

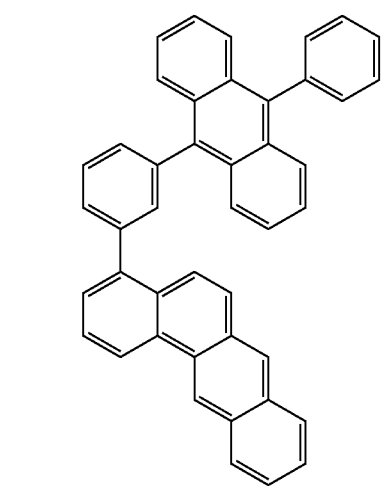

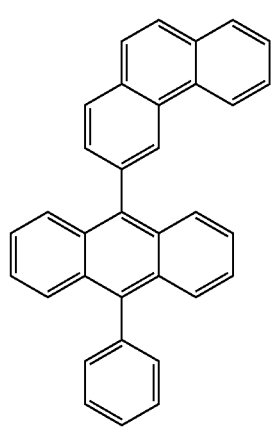

-continued

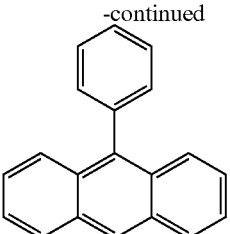

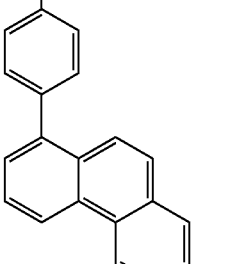

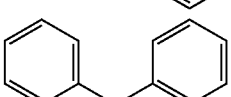

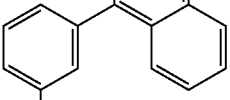

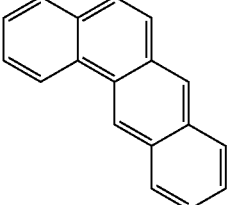

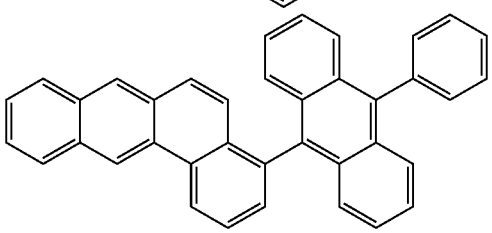

Suitable charge-transport materials, as can be used in the hole-injection or hole-transport layer or in the electron-transport layer of the organic electroluminescent device according to the invention, are, for example, the compounds disclosed in Y. Shirota et al., *Chem. Rev.* 2007, 107(4), 953-1010, or other materials as are employed in these layers in accordance with the prior art.

The cathode of the organic electroluminescent device preferably comprises metals having a low work function, metal alloys or multilayered structures comprising various metals, such as, for example, alkaline-earth metals, alkali metals, main-group metals or lanthanoids (for example Ca, Ba, Mg, Al, In, Mg, Yb, Sm, etc.). Also suitable are alloys comprising an alkali metal or alkaline-earth metal and silver, for example an alloy comprising magnesium and silver. In the case of multilayered structures, further metals which have a relatively high work function, such as, for example, Ag or Al, can also be used in addition to the said metals, in which case combinations of the metals, such as, for example, Ca/Ag, Ba/Ag or Mg/Ag, are generally used. It may also be preferred to introduce a thin interlayer of a material having a high dielectric constant between a metallic cathode and the organic semiconductor. Suitable for this purpose are, for example, alkali metal fluorides or alkaline-earth metal fluorides, but also the corresponding oxides or carbonates (for example LiF, $Li_2O$, $BaF_2$, MgO, NaF, CsF, $Cs_2CO_3$, etc.). Furthermore, lithium quinolinate (LiQ) can be used for this purpose. The layer thickness of this layer is preferably between 0.5 and 5 nm.

The anode preferably comprises materials having a high work function. The anode preferably has a work function of greater than 4.5 eV vs. vacuum. Suitable for this purpose are on the one hand metals having a high redox potential, such as, for example, Ag, Pt or Au. On the other hand, metal/metal oxide electrodes (for example $Al/Ni/NiO_x$, $Al/PtO_x$) may also be preferred. For some applications, at least one of the electrodes must be transparent or partially transparent in order to facilitate either irradiation of the organic material (organic solar cells) or the coupling-out of light (OLEDs, O-lasers). Preferred anode materials here are conductive mixed metal oxides. Particular preference is given to indium tin oxide (ITO) or indium zinc oxide (IZO). Preference is furthermore given to conductive, doped organic materials, in particular conductive, doped polymers.

The device is appropriately (depending on the application) structured, provided with contacts and finally sealed, since the lifetime of the devices according to the invention is shortened in the presence of water and/or air.

In a preferred embodiment, the organic electroluminescent device according to the invention is characterised in that one or more layers are coated by means of a sublimation process, in which the materials are applied by vapour deposition in vacuum sublimation units at an initial pressure of less than $10^{-5}$ mbar, preferably less than $10^{-6}$ mbar. However, it is also possible here for the initial pressure to be even lower, for example less than $10^{-7}$ mbar.

Preference is likewise given to an organic electroluminescent device, characterised in that one or more layers are coated by means of the OVPD (organic vapour phase deposition) process or with the aid of carrier-gas sublimation, in which the materials are applied at a pressure of between $10^{-5}$ mbar and 1 bar. A special case of this process is the OVJP (organic vapour jet printing) process, in which the materials are applied directly through a nozzle and are thus structured (for example M. S. Arnold et al., *Appl. Phys. Lett.* 2008, 92, 053301).

Preference is furthermore given to an organic electroluminescent device, characterised in that one or more layers are produced from solution, such as, for example, by spin coating, or by means of any desired printing process, such as, for example, screen printing, flexographic printing, nozzle printing or offset printing, but particularly preferably LITI (light induced thermal imaging, thermal transfer printing) or ink-jet printing. Soluble compounds of the formula (I), (II) or (III) are necessary for this purpose. High solubility can be achieved through suitable substitution of the compounds.

For the production of an organic electroluminescent device according to the invention, it is furthermore preferred to apply one or more layers from solution and one or more layers by a sublimation process.

The organic electroluminescent devices comprising one or more compounds according to the invention can be employed in displays, as light sources in lighting applications and as light sources in medical and/or cosmetic applications (for example light therapy).

On use of the compounds of the formula (I), (II) or (III) in an organic electroluminescent device, one or more of the advantages mentioned below can be achieved:

The compounds according to the invention are very highly suitable for use as matrix materials for phosphorescent dopants and for use as electron-transport materials. On use of the compounds according to the invention in these functions, good power efficiencies, low operating voltages and good lifetimes of the organic electroluminescent devices are obtained.

Furthermore, the compounds according to the invention are distinguished by high oxidation stability in solution, which has an advantageous effect during purification and handling of the compounds and on use thereof in electronic devices.

Furthermore, the compounds according to the invention are temperature-stable and can thus be sublimed substantially without decomposition. Purification of the compounds is thus simplified, and the compounds can be obtained in higher purity, which has a positive effect on the performance data of the electronic devices comprising the materials. In particular, devices having longer operating lifetimes can thus be produced.

The invention is explained in greater detail by the following working examples.

WORKING EXAMPLES

A) Synthesis Examples

The following syntheses are carried out, unless indicated otherwise, under a protective-gas atmosphere in dried solvents. Starting materials or reactants which can be employed are, for example, 3,4-dimethyl pyrrolo[3,4-b]indole-3,4 (2H)-dicarboxylate (*Science of Synthesis* 2002, 9, 441-552), 2-(3-bromophenyl)-4,6-diphenylpyrimidine, 4-(3-bromophenyl)-4,6-diphenylpyrimidine, 4-(3,5-dibromophenyl)-4,6-diphenylpyrimidine (WO 2005/085387) and 2-(3,5-dibromophenyl)-4,6-diphenylpyrimidine.

Example Compound 1 a) Diethyl 2-phenyl-2H-pyrrolo[3,4-b]indole-3,4-dicarboxylate

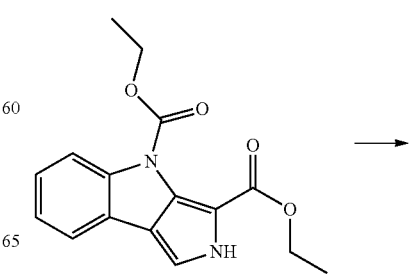

-continued

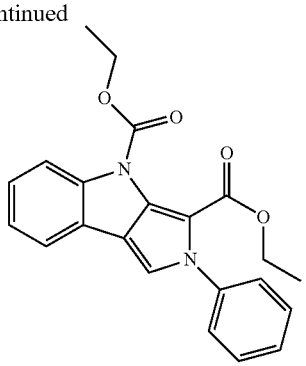

53 g (176 mmol) of diethyl pyrrolo[3,4-b]indole-3,4(2H)-dicarboxylate and 129 g (1059 mmol) of phenylboronic acid are dissolved in 2000 ml of dichloromethane and degassed. 71 ml of triarylamine and 40 g (356 mmol) of copper(II) acetate and 111 g of molecular sieve (0.4 NM) are added. The reaction mixture is subsequently stirred at room temperature for 80 h under protective-gas atmosphere. The cooled solution is diluted with toluene, washed a number of times with water, dried and evaporated. The product is purified by column chromatography on silica gel with toluene/heptane (1:2). Yield: 55.4 g (141 mmol), 80% of theory.

b) Ethyl 2-phenyl-2,4-dihydropyrrolo[3,4-b]indole-3-carboxylate

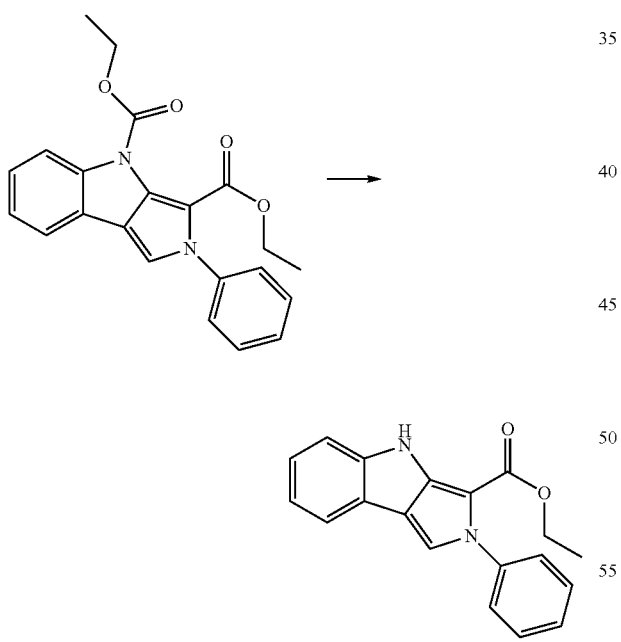

A solution of 41 g (300 mmol) of K$_2$CO$_3$ in 1500 ml of MeOH/H2O (3:1) is added to 37.6 g (100 mmol) of diethyl 2-phenyl-2H-pyrrolo[3,4-b]indole-3,4-dicarboxylate, and the mixture is heated under reflux for 2 h. After cooling, the mixture is extracted with dichloromethane and, after phase separation, dried and evaporated. The product is purified by column chromatography on silica gel with toluene/heptane (1:2). Yield: 19.7 g (65 mmol), 65% of theory.

c) 2-(2-Phenyl-2,4-dihydropyrrolo[3,4-b]indol-3-yl)propan-2-ol

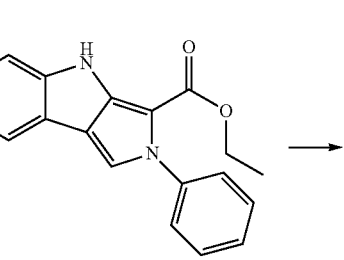

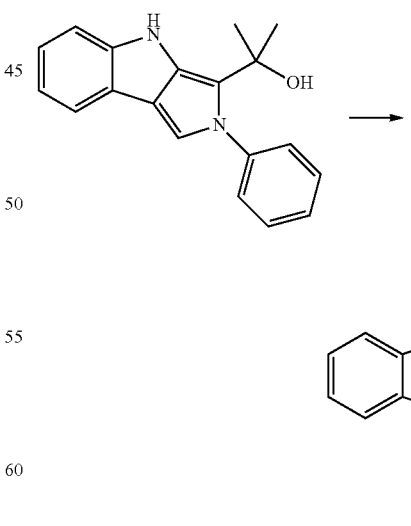

64.7 g (213 mmol) of ethyl 2-phenyl-2,4-dihydropyrrolo[3,4-b]indole-3-carboxylate are dissolved in 1500 ml of dried THF and degassed. The mixture is cooled to −78° C., and 569 ml (854 mmol) of methyllithium are added over the course of 40 min. The mixture is allowed to warm to −40° C. over the course of 1 h, and the reaction is monitored by TLC. When the reaction is complete, it is carefully quenched with MeOH at −30° C. The reaction solution is evaporated to ⅓ and mixed and washed with 1 l of methylene chloride. The organic phase is dried over MgSO$_4$ and evaporated. Yield: 55.5 g (191 mmol), 90% of theory, purity according to $^1$H-NMR about 94%.

d) Intermediate d)

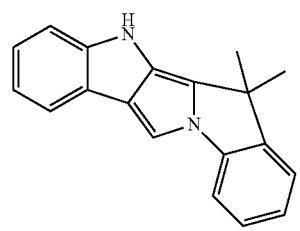

12.6 g (43.6 mmol) of 2-(2-phenyl-2,4-dihydropyrrolo[3,4-b]indol-3-yl)propan-2-ol are dissolved in 1200 ml of degassed toluene, and a suspension of 40 g of polyphos phoric acid and 28 ml of methanesulfonic acid is added, and the mixture is heated at 60° C. for 1 h. The batch is cooled, and water is added. A solid precipitates out, which is dissolved with methylene chloride/THF (1:1). The solution is carefully rendered alkaline using 20% NaOH, the phases are separated and dried over MgSO₄. The solid obtained is washed by stirring with heptane. Yield: 10.8 g (39 mmol), 92% of theory, purity according to ¹H-NMR about 98%.

e) Example Compound 1

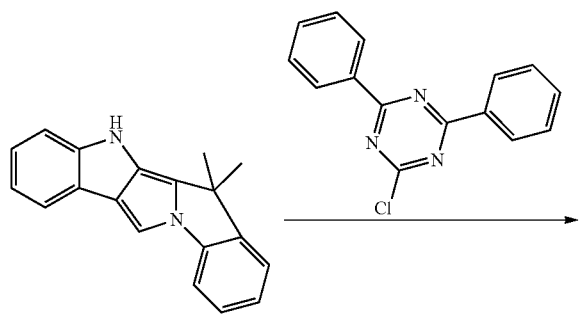

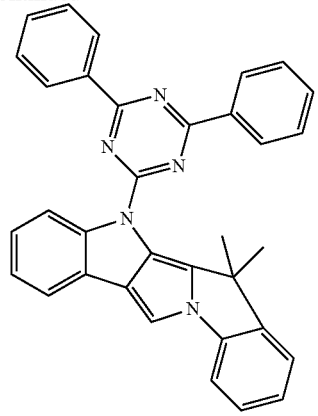

1

68 g (250 mmol) of intermediate d) are dissolved in 1000 ml of dimethylformamide under protective atmosphere, and 13.8 g of NaH 60% in mineral oil (345 mmol) are added. After 1 hour at room temperature, a solution of 73 g (270 mmol) of 2-chloro-4,6-diphenyl-1,3,5-triazine in 1000 ml of THF is added dropwise. The reaction mixture is subsequently stirred at room temperature for 12 h. After this time, the reaction mixture is poured onto ice and extracted three times with dichloromethane. The combined organic phases are dried over Na₂SO₄ and evaporated. The residue is extracted with hot toluene and recrystallised from toluene and finally sublimed in a high vacuum. The purity is 99.9%, yield 99 g (79%).

The following compounds are obtained by analogous synthetic procedures:

| Ex. | Starting material 1 | Starting material 2 | Product | Yield |
|---|---|---|---|---|
| 1b | | 804548-71-8 | | 65% |

-continued

| Ex. | Starting material 1 | Starting material 2 | Product | Yield |
|---|---|---|---|---|
| 1c | 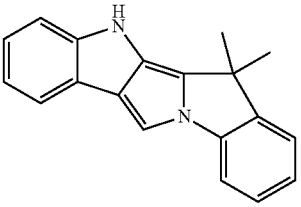 [SMILES: CC1(C)c2ccccc2-n2cc3c([nH]c4ccccc43)c21] | 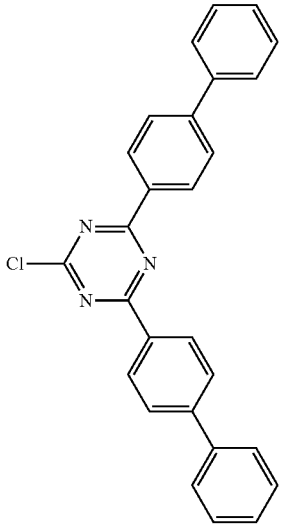 [SMILES: Clc1nc(-c2ccc(-c3ccccc3)cc2)nc(-c2ccc(-c3ccccc3)cc2)n1]<br>182918-13-4 | 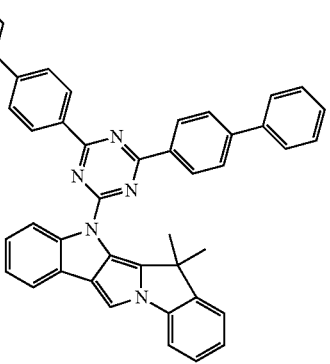 | 77% |
| 1d | 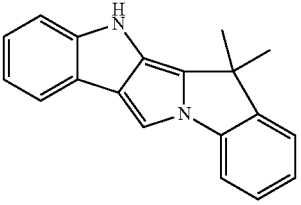 [SMILES: CC1(C)c2ccccc2-n2cc3c([nH]c4ccccc43)c21] | 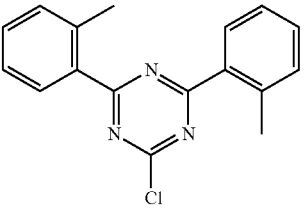 [SMILES: Cc1ccccc1-c1nc(Cl)nc(-c2ccccc2C)n1]<br>78941-34-1 | 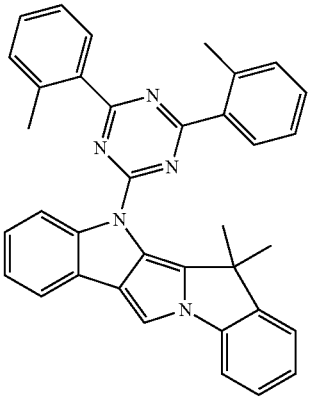 [SMILES: Cc1ccccc1-c1nc(-c2ccccc2C)nc(-n2c3ccccc3c3cn4c(c32)C(C)(C)c2ccccc2-4)n1] | 63% |

Synthesis of the intermediate
4-(2-bromophenyl)-2,6-diphenylpyrimidine

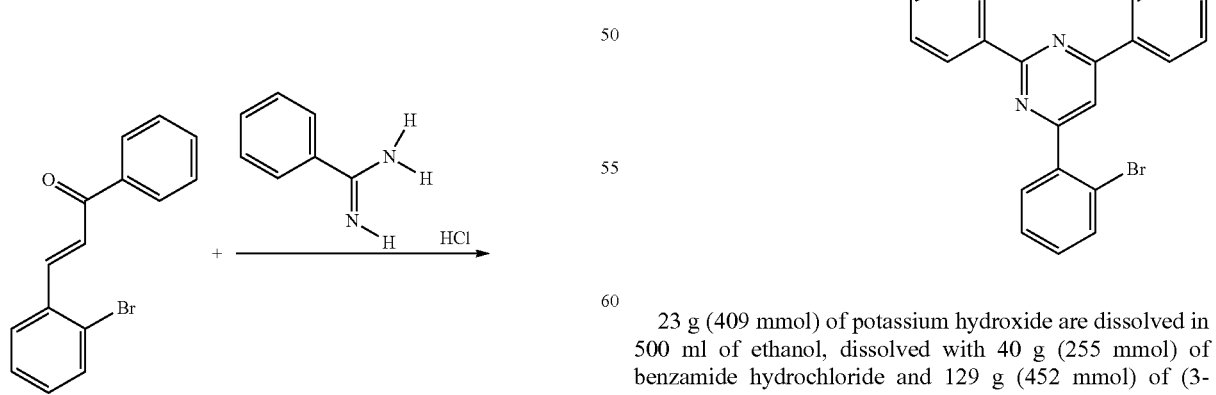

23 g (409 mmol) of potassium hydroxide are dissolved in 500 ml of ethanol, dissolved with 40 g (255 mmol) of benzamide hydrochloride and 129 g (452 mmol) of (3-(bromophenyl)-1-phenyl-2-propen-1-one at room temperature, 500 ml of ethanol are added, and the mixture is stirred under reflux for 3 h. After cooling to room temperature, the precipitated solid is filtered off with suction, washed with a little EtOH and dried, leaving 55 g (129 mmol), 50%, of the product 4-(2-bromophenyl)-2,6-diphenyl-pyrimidine in the form of colourless crystals.

Example Compound 2

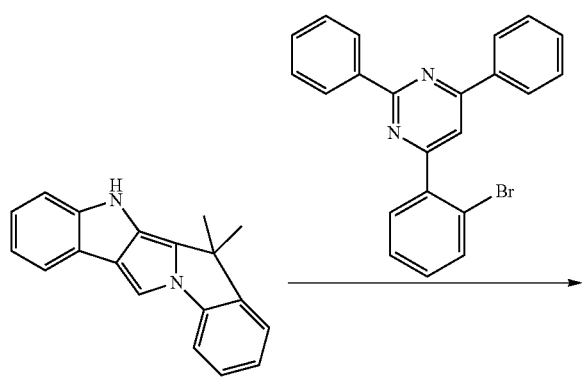

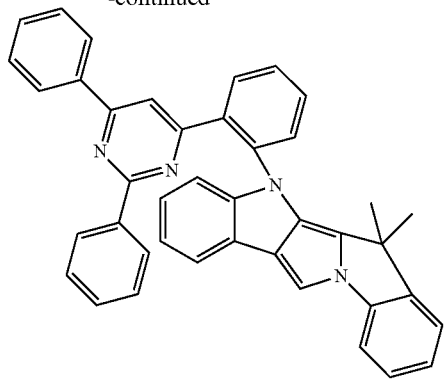

21 g (79.8 mmol) of 2,12-dimethyl-10-phenyl-10,12-dihydro-10-aza-indeno[2,1-b]fluorene, 34 g (87 mmol) of 4-(2-bromophenyl)-2,6-diphenylpyrimidine, 15.9 ml (15.9 mmol) of 1 mol/l tri-tert-butylphosphine and 1.79 g (7.9 mmol) of palladium acetate are suspended in 120 ml of p-xylene under protective gas. The reaction mixture is heated under reflux for 16 h. After cooling, the organic phase is separated off, washed three times with 200 ml of water and subsequently evaporated to dryness. The residue is extracted with hot toluene, recrystallised from toluene and finally sublimed in a high vacuum. The purity is 99.9%, yield 36 g (62 mmol), 81% of theory.

The following compounds are obtained by an analogous synthetic procedure:

| Ex. | Starting material 1 | Starting material 2 | Product | Yield |
|---|---|---|---|---|
| 2b |  |  864377-28-6 |  | 70% |

-continued
| Ex. | Starting material 1 | Starting material 2 | Product | Yield |
|---|---|---|---|---|
| 2c | 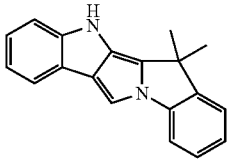 [SMILES: CC1(C)c2ccccc2-n2cc3c([nH]c4ccccc43)c21] | 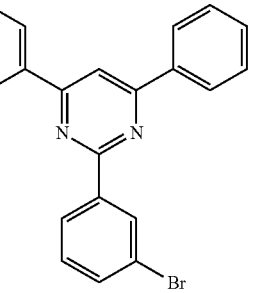 864377-22-0 | 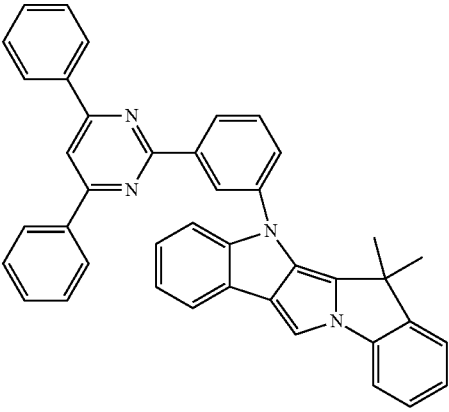 [SMILES: CC1(C)c2ccccc2-n2cc3c4ccccc4n(-c4cccc(-c5nc(-c6ccccc6)cc(-c6ccccc6)n5)c4)c3c21] | 76% |
| 2d | 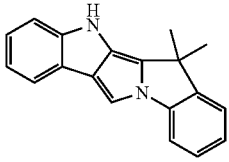 [SMILES: CC1(C)c2ccccc2-n2cc3c([nH]c4ccccc43)c21] | 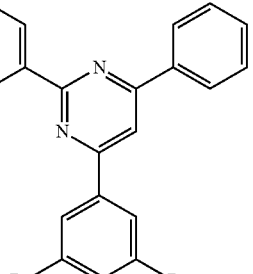 607740-08-9 | 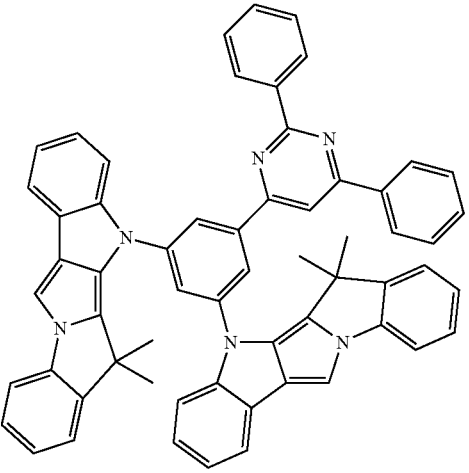 [SMILES: CC1(C)c2ccccc2-n2cc3c4ccccc4n(-c4cc(-c5cc(-c6ccccc6)nc(-c6ccccc6)n5)cc(-n5c6ccccc6c6cn7c(c65)C(C)(C)c5ccccc5-7)c4)c3c21] | 64% |
| 2e | 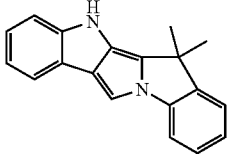 [SMILES: CC1(C)c2ccccc2-n2cc3c([nH]c4ccccc43)c21] | 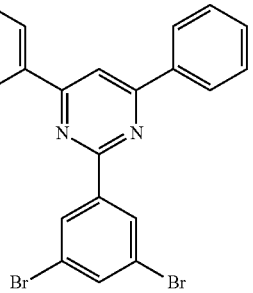 942132-67-4 | 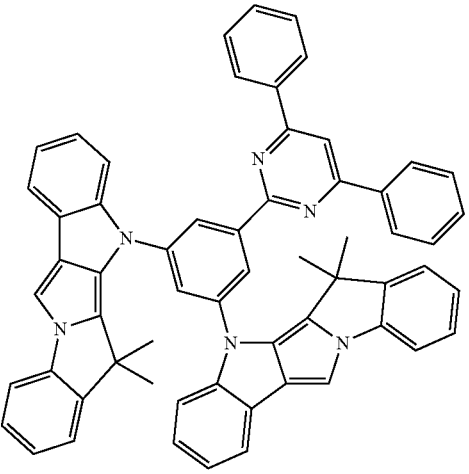 [SMILES: CC1(C)c2ccccc2-n2cc3c4ccccc4n(-c4cc(-c5nc(-c6ccccc6)cc(-c6ccccc6)n5)cc(-n5c6ccccc6c6cn7c(c65)C(C)(C)c5ccccc5-7)c4)c3c21] | 71% |

B. Device Examples

Production of OLEDs

OLEDs according to the invention and OLEDs in accordance with the prior art are produced by a general process in accordance with WO 2004/058911, which is adapted to the circumstances described here (layer-thickness variation, materials).

The data for various OLEDs are presented in Examples E1 to E8 below (see Tables 1 and 2). Glass plates coated with structured ITO (indium tin oxide) in a thickness of 150 nm are coated with 20 nm of PEDOT (poly(3,4-ethylenedioxy-2,5-thiophene), applied by spin coating from water; purchased from H. C. Starck, Goslar, Germany) for improved processing. These coated glass plates form the substrates to which the OLEDs are applied. The OLEDs basically have the following layer structure: substrate/hole-transport layer (HTL)/optional interlayer (IL)/electron-blocking layer (EBL)/emission layer (EML)/optional hole-blocking layer (HBL)/electron-transport layer (ETL)/optional electron-injection layer (EIL) and finally a cathode. The cathode is formed by an aluminium layer with a thickness of 100 nm. The precise structure of the OLEDs is shown in Table 1. The materials required for the production of the OLEDs are shown in Table 3.

All materials are applied by thermal vapour deposition in a vacuum chamber. The emission layer here always consists of at least one matrix material (host material) and an emitting dopant (emitter), to which the matrix material or materials is (are) admixed by co-evaporation in a certain proportion by volume. An expression such as H5:TER2 (88%:12%) here means that material H5 is present in the layer in a proportion by volume of 88% and TER2 is present in the layer in a proportion of 12%.

The OLEDs are characterised by standard methods. To this end, the electroluminescence spectra, the current efficiency (measured in cd/A), the power efficiency (measured in lm/W) and the external quantum efficiency (EQE, measured in percent) as a function of the luminous density, calculated from current/voltage/luminous density characteristic lines (IUL characteristic lines) assuming Lambert emission characteristics, and the lifetime are determined. The electroluminescence spectra are determined at a luminous density of 1000 cd/m$^2$, and the CIE 1931x and y colour coordinates are calculated therefrom. The expression U1000 in Table 2 denotes the voltage required for a luminous density of 1000 cd/m$^2$. CE1000 and PE1000 denote the current and power efficiency respectively which are achieved at 1000 cd/m$^2$. Finally, EQE1000 denotes the external quantum efficiency at an operating luminous density of 1000 cd/m$^2$.

The data for the various OLEDs are summarised in Table 2. The materials according to the invention give good efficiency and operating voltage on use as matrix materials for red- and green-phosphorescent emitters (Examples E1-E7 in Table 2). Furthermore, good performance data are obtained on use of material H3 as electron-transport material (Example E8).

TABLE 1

Structure of the OLEDs

| Ex. | HTL Thickness | IL Thickness | EBL Thickness | EML Thickness | HBL Thickness | ETL Thickness | EIL Thickness |
|---|---|---|---|---|---|---|---|
| E1 | SpA1 70 nm | HATCN 5 nm | BPA1 90 nm | H1:TEG1 (90%:10%) 30 nm | — | ST1:LiQ (50%:50%) 40 nm | — |
| E2 | SpA1 20 nm | — | NPB 20 nm | H2:TER1 (85%:15%) 30 nm | — | Alq$_3$ 20 nm | LiF 1 nm |
| E3 | SpA1 70 nm | HATCN 5 nm | BPA1 90 nm | H3:TEG1 (90%:10%) 30 nm | — | ST1:LiQ (50%:50%) 40 nm | — |
| E4 | SpA1 70 nm | HATCN 5 nm | BPA1 90 nm | H4:TEG1 (90%:10%) 30 nm | IC1 10 nm | ST1:LiQ (50%:50%) 40 nm | — |
| E5 | SpA1 70 nm | HATCN 5 nm | SpA2 90 nm | H5:TEG1 (90%:10%) 30 nm | IC1 10 nm | ST1:LiQ (50%:50%) 40 nm | — |
| E6 | SpA1 20 nm | — | NPB 20 nm | H5:TER2 (88%:12%) 30 nm | ST1 5 nm | ST1:LiQ (50%:50%) 20 nm | LiQ 1 nm |
| E7 | SpA1 70 nm | HATCN 5 nm | BPA1 90 nm | H6:TEG1 (90%:10%) 30 nm | IC1 10 nm | ST1:LiQ (50%:50%) 40 nm | — |
| E8 | SpA1 70 nm | HATCN 5 nm | BPA1 90 nm | IC1:TEG1 (90%:10%) 30 nm | — | H3 40 nm | LiQ 3 nm |

TABLE 2

Data for the OLEDs

| Ex. | U1000 (V) | CE1000 (cd/A) | PE1000 (lm/W) | EQE 1000 | CIE x/y at 1000 cd/m$^2$ |
|---|---|---|---|---|---|
| E1 | 3.6 | 47 | 41 | 13.1% | 0.36/0.60 |
| E2 | 5.2 | 5.8 | 3.5 | 9.6% | 0.69/0.31 |
| E3 | 3.8 | 38 | 31 | 10.4% | 0.36/0.60 |
| E4 | 3.9 | 42 | 34 | 11.7% | 0.37/0.60 |
| E5 | 3.4 | 52 | 49 | 14.5% | 0.36/0.60 |
| E6 | 5.4 | 10.7 | 6.2 | 9.9% | 0.66/0.33 |
| E7 | 3.6 | 43 | 38 | 11.9% | 0.36/0.61 |
| E8 | 3.8 | 48 | 40 | 13.4% | 0.36/0.60 |

TABLE 3
Structural formulae of the materials for the OLEDs
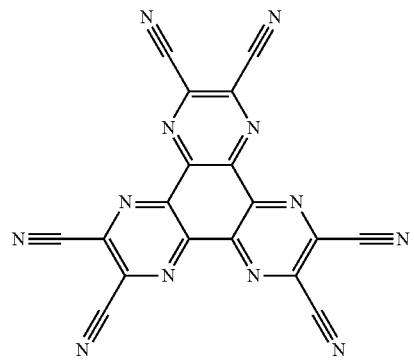 [SMILES: N#Cc1nc2c3nc(C#N)c(C#N)nc3c3nc(C#N)c(C#N)nc3c2nc1C#N]
HATCN
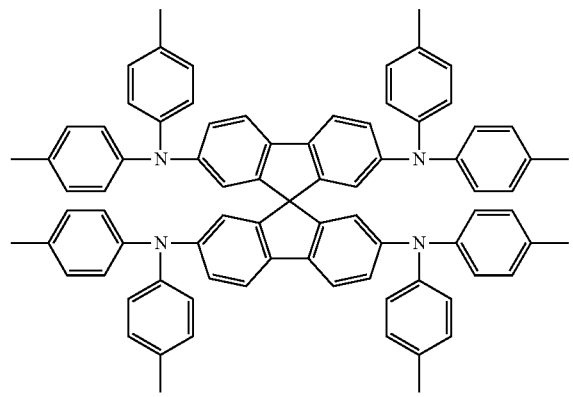
SpA1
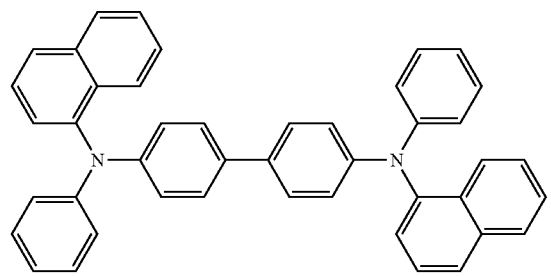 [SMILES: c1ccc(N(c2ccc(-c3ccc(N(c4ccccc4)c4cccc5ccccc45)cc3)cc2)c2cccc3ccccc23)cc1]
NPB
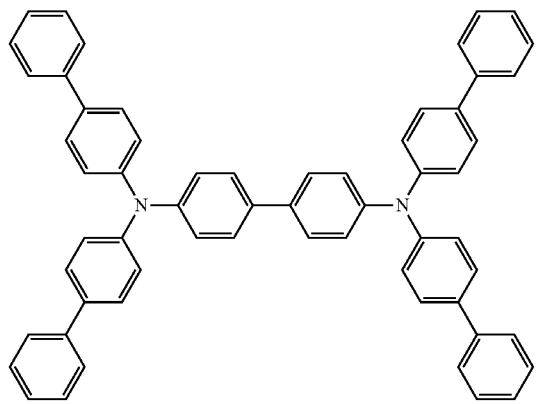 [SMILES: c1ccc(-c2ccc(N(c3ccc(-c4ccccc4)cc3)c3ccc(-c4ccc(N(c5ccc(-c6ccccc6)cc5)c5ccc(-c6ccccc6)cc5)cc4)cc3)cc2)cc1]
BPA1
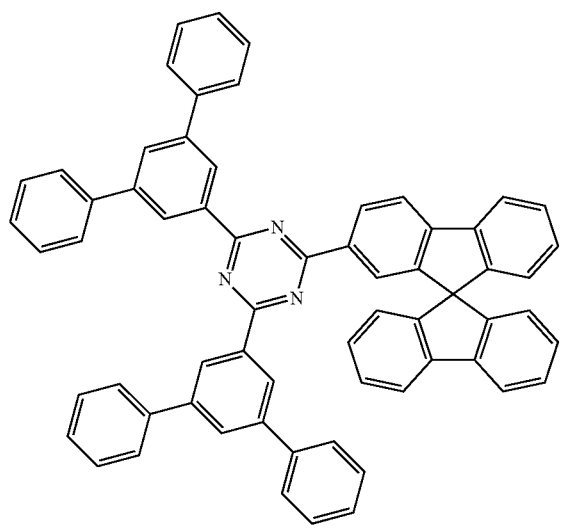 [SMILES: c1ccc(-c2cc(-c3ccccc3)cc(-c3nc(-c4cc(-c5ccccc5)cc(-c5ccccc5)c4)nc(-c4ccc5c(c4)C4(c6ccccc6-c6ccccc64)c4ccccc4-5)n3)c2)cc1]
ST1
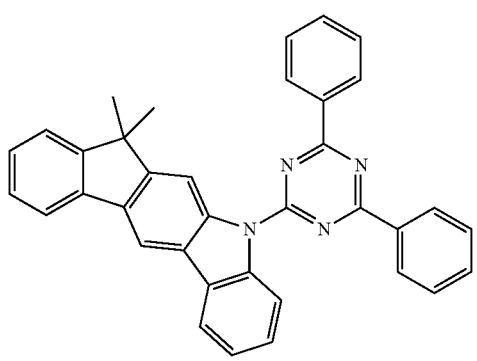 [SMILES: CC1(C)c2ccccc2-c2cc3c4ccccc4n(-c4nc(-c5ccccc5)nc(-c5ccccc5)n4)c3cc21]
IC1

TABLE 3-continued
Structural formulae of the materials for the OLEDs
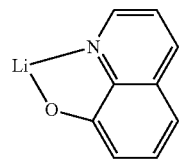
LiQ
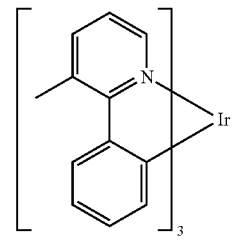
TEG1
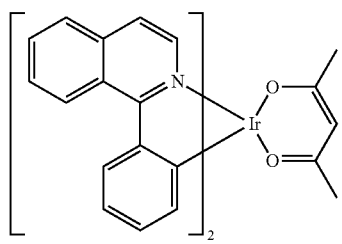
TER1
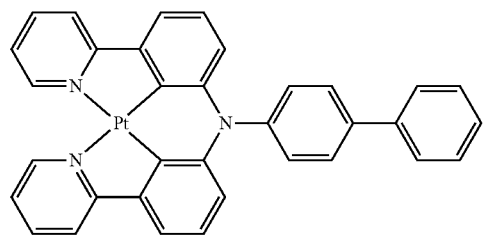
TER2
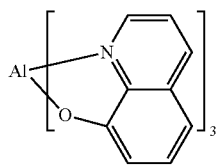
Alq$_3$
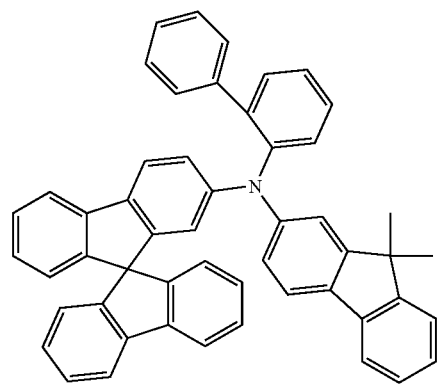 [SMILES: CC1(C)c2ccccc2-c2ccc(N(c3ccc4c(c3)C3(c5ccccc5-c5ccccc53)c3ccccc3-4)c3ccccc3-c3ccccc3)cc21]
SpA2
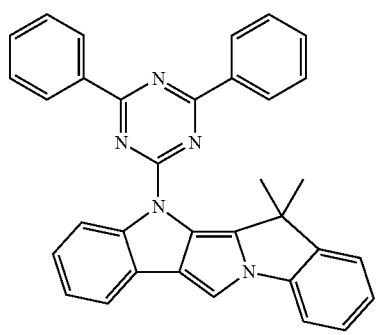 [SMILES: CC1(C)c2ccccc2-n2cc3c4ccccc4n(-c4nc(-c5ccccc5)nc(-c5ccccc5)n4)c3c21]
H1
(Example compound 1)
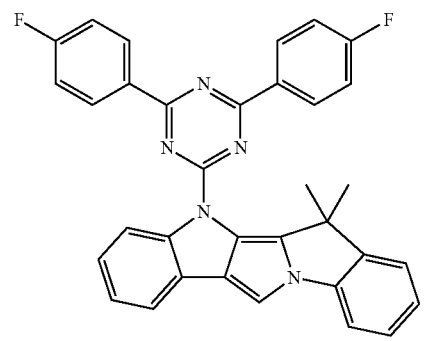 [SMILES: CC1(C)c2ccccc2-n2cc3c4ccccc4n(-c4nc(-c5ccc(F)cc5)nc(-c5ccc(F)cc5)n4)c3c21]
H2
(Example compound 1b)

TABLE 3-continued

Structural formulae of the materials for the OLEDs

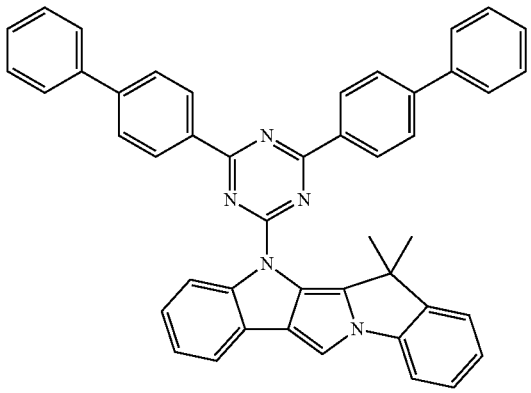 [SMILES: CC1(C)c2ccccc2-n2cc3c4ccccc4n(-c4nc(-c5ccc(-c6ccccc6)cc5)nc(-c5ccc(-c6ccccc6)cc5)n4)c3c21]

H3
(Example compound 1c)

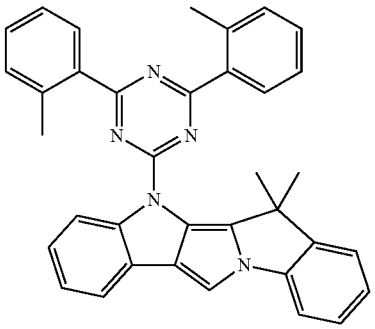 [SMILES: Cc1ccccc1-c1nc(-c2ccccc2C)nc(-n2c3ccccc3c3cn4c(c32)C(C)(C)c2ccccc2-4)n1]

H4
(Example compound 1d)

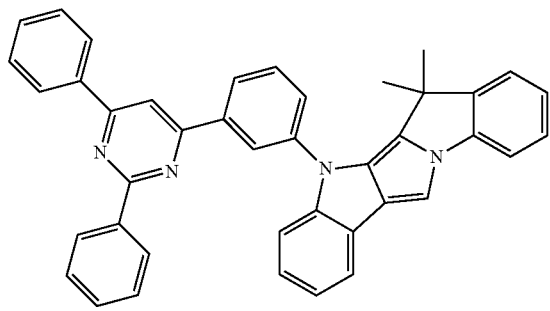 [SMILES: CC1(C)c2ccccc2-n2cc3c4ccccc4n(-c4cccc(-c5cc(-c6ccccc6)nc(-c6ccccc6)n5)c4)c3c21]

H5
(Example compound 2b)

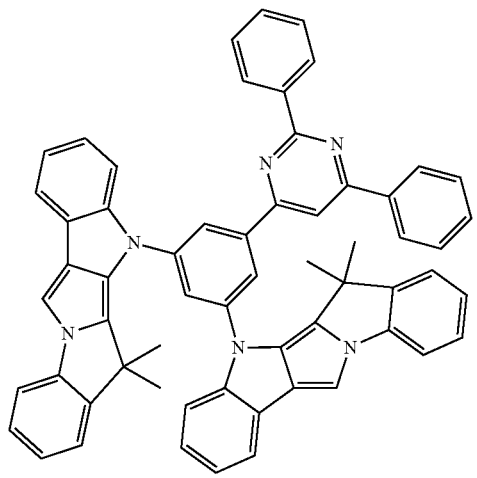 [SMILES: CC1(C)c2ccccc2-n2cc3c4ccccc4n(-c4cc(-c5cc(-c6ccccc6)nc(-c6ccccc6)n5)cc(-n5c6ccccc6c6cn7c(c65)C(C)(C)c5ccccc5-7)c4)c3c21]

H6
(Example compound 2d)

The invention claimed is:

1. A compound of a formula (I), (II) or (III)

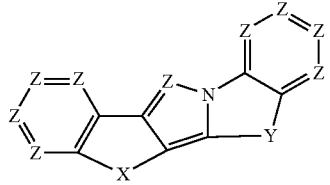

formula (I)

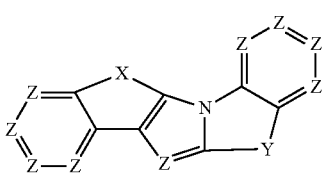

formula (II)

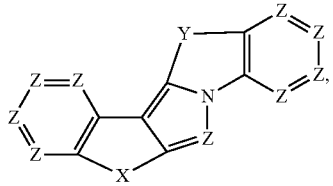

formula (III)

where the following applies to the symbols occurring:

Z is on each occurrence, identically or differently, $CR^2$ or N;

X and Y are on each occurrence, identically or differently, a divalent group selected from the group consisting of $BR^2$, $C(R^2)_2$, $C=NR^2$, $C=C(R^2)_2$, $C=S$, $Si(R^2)_2$, $NR^1$, $PR^2$, $P(=O)R^2$, O, S, $S=O$ and $S(=O)_2$;

$R^1$ is on each occurrence, identically or differently, an aromatic having 6 to 60 aromatic ring atoms or a heteroaromatic ring system having 5 to 60 aromatic ring atoms, which is optionally substituted by one or more radicals $R^3$ and which is optionally linked to a substituent $R^2$ on the skeleton or an atom of the skeleton;

$R^2$ is on each occurrence, identically or differently, H, D, F, Cl, Br, I, $B(OR^3)_2$, CHO, $C(=O)R^3$, $CR^3=C(R^3)_2$, CN, $C(=O)OR^3$, $C(=O)N(R^3)_2$, $Si(R^3)_3$, $N(R^3)_2$, $N(Ar^1)_2$, $NO_2$, $P(=O)(R^3)_2$, $OSO_2R^3$, $OR^3$, $S(=O)R^3$, $S(=O)_2R^3$, a straight-chain alkyl, alkoxy or thioalkyl group having 1 to 20 C atoms or a branched or cyclic alkyl, alkoxy or thioalkyl group having 3 to 20 C atoms or an alkenyl or alkynyl group having 2 to 20 C atoms, where the above-mentioned groups may each be substituted by one or more radicals $R^3$ and where one or more adjacent or non-adjacent $CH_2$ groups in the above-mentioned groups is optionally replaced by $—R^3C=CR^3—$, $Si(R^3)_2$, $Ge(R^3)_2$, $Sn(R^3)_2$, C=O, C=S, C=Se, $C=NR^3$, $—C(=O)O—$, $—C(=O)NR^3—$, $NR^3$, $P(=O)(R^3)$, $—O—$, $—S—$, SO or $SO_2$ and where one or more H atoms in the above-mentioned groups is optionally replaced by D, F, Cl, Br, I, CN or $NO_2$, or an aromatic having 6 to 60 aromatic ring atoms or a heteroaromatic ring system having 5 to 60 aromatic ring atoms, which may in each case be substituted by one or more radicals $R^3$, or an aryloxy having 6 to 60 aromatic ring atoms or a heteroaryloxy group having 5 to 60 aromatic ring atoms, which is optionally substituted by one or more radicals $R^3$, where two or more radicals $R^2$ is optionally linked to one another and may form a ring or a ring system;

$R^3$ is on each occurrence, identically or differently, H, D, F, Cl, Br, I, $B(OR^4)_2$, CHO, $C(=O)R^4$, $CR^4=C(R^4)_2$, CN, $C(=O)OR^4$, $C(=O)N(R^4)_2$, $Si(R^4)_3$, $N(R^4)_2$, $NO_2$, $P(=O)(R^4)_2$, $OSO_2R^4$, $OR^4$, $S(=O)R^4$, $S(=O)_2R^4$, a straight-chain alkyl, alkoxy or thioalkyl group having 1 to 20 C atoms or a branched or cyclic alkyl, alkoxy or thioalkyl group having 3 to 20 C atoms or an alkenyl or alkynyl group having 2 to 20 C atoms, where the above-mentioned groups may each be substituted by one or more radicals $R^4$ and where one or more adjacent or non-adjacent $CH_2$ groups in the above-mentioned groups is optionally replaced by $—R^4C=CR^4—$, $—C≡C—$, $Si(R^4)_2$, $Ge(R^4)_2$, $Sn(R^4)_2$, C=O, C=S, C=Se, $C=NR^4$, $—C(=O)O—$, $—C(=O)NR^4—$, $NR^4$, $P(=O)(R^4)$, $—O—$, $—S—$, SO or $SO_2$ and where one or more H atoms in the above-mentioned groups is optionally replaced by D, F, Cl, Br, I, CN or $NO_2$, or an aromatic having 6 to 60 aromatic ring atoms or a heteroaromatic ring system having 5 to 60 aromatic ring atoms, which may in each case be substituted by one or more radicals $R^4$, or an aryloxy having 6 to 60 aromatic ring atoms or a heteroaryloxy group having 5 to 60 aromatic ring atoms, which is optionally substituted by one or more radicals $R^4$, where two or more radicals $R^3$ is optionally linked to one another and may form a ring or a ring system;

$R^4$ is, identically or differently on each occurrence, H, D, F or an aliphatic, aromatic and/or heteroaromatic organic radical having 1 to 20 C atoms, in which, in addition, one or more H atoms is optionally replaced by D or F; two or more substituents $R^4$ here may also be linked to one another and form a ring or a ring system; and $Ar^1$ is on each occurrence, identically or differently, an aromatic having 6 to 60 aromatic ring atoms or a heteroaromatic ring system having 5 to 30 aromatic ring atoms, which is optionally substituted by one or more radicals $R^3$.

2. The compound according to claim 1, wherein there are 0, 1 or 2 groups Z per aromatic six-membered ring of a compound of the formula (I), (II) or (III) are equal to N, and the remaining groups Z are equal to $CR^2$.

3. The compound according to claim 1, wherein X is C=O, $NR^1$, O, S, S=O or $S(=O)_2$.

4. The compound according to claim 1, wherein Y is $C(R^2)_2$, $NR^1$, O or S.

5. The compound according to claim 1, wherein $R^2$ is selected on each occurrence, identically or differently, from H, D, F, CN, $Si(R^3)_3$, $N(R^3)_2$ or a straight-chain alkyl or alkoxy group having 1 to 20 C atoms or a branched or cyclic alkyl or alkoxy group having 3 to 20 C atoms, where the above-mentioned groups may each be substituted by one or more radicals $R^3$ and where one or more adjacent or non-adjacent $CH_2$ groups in the above-mentioned groups is optionally replaced by $—C≡C—$, $—R^3C=CR^3—$, $Si(R^3)_2$, C=O, $C=NR^3$, $—NR^3—$, $—O—$, $—S—$, $—C(=O)O—$ or $—C(=O)NR^3—$, or an aromatic having 6 to 60 aromatic ring atoms or a heteroaromatic ring system having 5 to 20 aromatic ring atoms, which may in each case be substituted by one or more radicals $R^3$, where two or more radicals $R^2$ is optionally linked to one another and may form a ring or a ring system.

6. The compound according to claim 1, wherein at least one group $R^1$ or $R^2$ is present which is selected from
heteroaryl groups having 1 to 20 C atoms, which may optionally be bonded via one or more divalent aryl groups bonded in between and which is optionally substituted by one or more radicals $R^3$,
aromatic having 6 to 60 aromatic ring atoms or a heteroaromatic ring systems having 5 to 20 aromatic ring atoms, which is optionally substituted by one or more radicals $R^3$, and
arylamine groups, which is optionally substituted by one or more radicals $R^3$.

7. The compound according to claim 6, wherein the heteroaryl groups are selected from the group consisting of pyridine, pyrimidine, pyridazine, pyrazine, triazine and benzimidazole, each of which is optionally substituted by one or more radicals $R^3$, and the aromatic or heteroaromatic ring systems are selected from the group consisting of naphthyl, anthracenyl, phenanthrenyl, benzanthracenyl, pyrenyl, biphenyl, terphenyl and quaterphenyl, each of which is optionally substituted by one or more radicals $R^3$.

8. A process for the preparation of the compound according to claim 1, comprising at least the following steps:
(a) a coupling reaction between the pyrrole nitrogen atom and an aryl or heteroaryl group; and
(b) a ring-closure reaction between the pyrrole ring and the aryl or heteroaryl group coupled in step (a).

9. An oligomer, polymer or dendrimer comprising one or more compounds according to claim 1, where the bond(s) to the polymer, oligomer or dendrimer is optionally localised at any positions in formula (I), (II) or (III) that are substituted by $R^1$ or $R^2$.

10. A formulation comprising at least one compound according to claim 1 and at least one solvent.

11. A formulation comprising at least one polymer, oligomer or dendrimer according to claim 9 and at least one solvent.

12. An electronic device comprising the compound according to claim 1.

13. An electronic device comprising the polymer according to claim 9.

14. An organic electroluminescent device comprising the compound according to claim 1.

15. An organic electroluminescent device comprising the polymer according to claim 9.

16. The electronic device as claimed in claim 12, wherein the device is an organic integrated circuit, an organic field-effect transistor, an organic thin-film transistor, an organic light-emitting transistor, an organic solar cell, an organic optical detector, an organic photoreceptor, an organic field-quench device, a light-emitting electrochemical cell, an organic laser diode or an organic electroluminescent device.

17. An organic electroluminescent device which comprises the compound according to claim 1 is employed as hole-transport material in a hole-transport layer or hole-injection layer and/or is employed as matrix material in an emitting layer and/or is employed as electron-transport material in an electron-transport layer.

18. An organic electroluminescent device which comprises the polymer, oligomer or dendrimer according to claim 9 is employed as hole-transport material in a hole-transport layer or hole-injection layer and/or is employed as matrix material in an emitting layer and/or is employed as electron-transport material in an electron-transport layer.

* * * * *